United States Patent
Nicol et al.

(10) Patent No.: US 11,898,141 B2
(45) Date of Patent: Feb. 13, 2024

(54) HIGH-THROUGHPUT ASSEMBLY OF GENETIC ELEMENTS

(71) Applicants: THE BROAD INSTITUTE, INC., Cambridge, MA (US); MASSACHUSETTS INSTITUTE OF TECHNOLOGY, Cambridge, MA (US)

(72) Inventors: Robert Nicol, Cambridge, MA (US); Lauren Andrews, Cambridge, MA (US); Tarjei Mikkelsen, Cambridge, MA (US); Christopher Voigt, Belmont, MA (US)

(73) Assignees: The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/313,863

(22) PCT Filed: May 27, 2015

(86) PCT No.: PCT/US2015/032760
§ 371 (c)(1),
(2) Date: Nov. 23, 2016

(87) PCT Pub. No.: WO2015/184016
PCT Pub. Date: Dec. 3, 2015

(65) Prior Publication Data
US 2017/0267997 A1    Sep. 21, 2017

Related U.S. Application Data

(60) Provisional application No. 62/003,331, filed on May 27, 2014.

(51) Int. Cl.
| | | |
|---|---|---|
| *C12N 15/10* | (2006.01) | |
| *C12N 15/66* | (2006.01) | |
| *C40B 40/06* | (2006.01) | |
| *G16B 20/00* | (2019.01) | |
| *G16B 30/00* | (2019.01) | |
| *G16B 20/20* | (2019.01) | |
| *G16B 30/20* | (2019.01) | |

(52) U.S. Cl.
CPC ..... *C12N 15/1065* (2013.01); *C12N 15/1082* (2013.01); *C12N 15/1093* (2013.01); *C12N 15/66* (2013.01); *C40B 40/06* (2013.01); *G16B 20/00* (2019.02); *G16B 20/20* (2019.02); *G16B 30/00* (2019.02); *G16B 30/20* (2019.02)

(58) Field of Classification Search
CPC ............ C12N 15/1093; C12N 15/1031; C12N 15/66; C12N 15/1065; C40B 40/06; C12Q 1/6869–1/6874; C12Q 2563/179; C12Q 2525/155; C12Q 2525/131; C12Q 2521/501; C12Q 2521/313
See application file for complete search history.

(56) References Cited

U.S. PATENT DOCUMENTS

| | | | |
|---|---|---|---|
| 2003/0148335 A1* | 8/2003 | Shen ............... | C12Q 2563/179 435/6.16 |
| 2007/0269870 A1 | 11/2007 | Church et al. | |
| 2010/0124768 A1* | 5/2010 | Serber ............... | C12N 15/1093 435/91.5 |
| 2013/0298265 A1 | 11/2013 | Cunnac et al. | |
| 2014/0121116 A1 | 5/2014 | Richards et al. | |
| 2017/0233727 A1* | 8/2017 | Zhou ................. | C12N 15/1093 506/4 |

FOREIGN PATENT DOCUMENTS

| | | |
|---|---|---|
| WO | 2008000090 A1 | 1/2008 |
| WO | 2008054543 A2 | 5/2008 |

OTHER PUBLICATIONS

Merryman et al. Methods and application for assembling large DNA constructs. Metabolic Engineering, vol. 14, pp. 196-204, Mar. 2012. (Year: 2012).*
Sarrion-Perdigones et al. GoldenBraid 2.0: A comprehensive DNA assembly framework for plant synthetic biology. Plant Physiology, vol. 162, pp. 1618-1631, Jul. 2013, published online May 13, 2013, including Supplementary Figures 1-8, printed as 8 pages and Supplementary Table, printed as 2 pages. (Year: 2013).*
Schwartz et al. Accurate gene synthesis with tag-directed retrieval of sequence-verified DNA molecules. Nature Methods, vol. 9, No. 9, pp. 913-915, Aug. 12, 2012, including pp. 1/2-2/2 of Online Methods, and pp. 1/45-45-45 of Supplementary Information. (Year: 2012).*
Kim et al. 'Shotgun DNA synthesis' for the high-throughput construction of large DNA molecules. Nucleic Acids Research, vol. 40, No. 18, e140, Jun. 16, 2012, printed as pp. 1/8, including pp. 1/30 of Supplementary Data. (Year: 2012).*

(Continued)

*Primary Examiner* — Jennifer Dunston
(74) *Attorney, Agent, or Firm* — F. Brent Nix, Esq.; Johnson, Marcou, Isaacs & Nix, LLC

(57) ABSTRACT

Disclosed is a method of generating a set of sequence-verified nucleic acid elements for the combinatorial construction of genetic elements. The method includes: providing a plurality of nucleic acid parts; assembling nucleic acid parts to form a one or more nucleic acid elements, wherein the nucleic acid elements include at least two sequences selected from the plurality of parts; and determining the sequence of the nucleic acid elements. Further disclosed is a pool of higher-order nucleic acid constructs or amplification products thereof, comprising one or more nucleic acid elements as well as kits including a pool of sequence-verified nucleic acid elements of claims and/or a pool of higher-order nucleic acid constructs; and a plurality of primers for retrieving one or more sequence-verified nucleic acid elements and/or higher-order nucleic acid constructs.

10 Claims, 52 Drawing Sheets

(56) References Cited

OTHER PUBLICATIONS

Chen et al. Generation and analysis of barcode-tagged insertion mutant library in the fission yeast Schizosaccharomyces pombe. BMC Genomics, vol. 13, 161, May 3, 2012, printed as pp. Jan. 18, 18/18. (Year: 2012).*

Nelson et al. Chapter 27. Overlap extension PCR: An efficient method for transgene construction. Virginie Orgogozo and Matthew V Rockman (Eds.), Molecular Methods for Evolutionary Genetics, Methods in Molecular Biology, vol. 772, pp. 549-470, 2011. (Year: 2011).*

Extended European Search Report issued in European Application No. 15798953.4 dated Nov. 24, 2017, Nov. 24, 2017, 1-8.

Hiatt, et al., "Parallel, Tag-directed Assembly of Locally Derived Short Sequence Reads", Nature Methods, vol. 7, No. 2, Feb. 2010, p. 119 XP055005905, Jan. 17, 2010, 1-7.

Sleight, et al., "Randomized BioBrick Assembly: A Novel DNA Assembly Method for Randomizing and Optimizing Genetic Circuits and Metabolic Pathways", ACS Synthetic Biology, vol. 2, No. 9; pp. 506-518; XP055400088, Jul. 10, 2013, 1-13.

Smanski, et al., "Functional Optimization of Gene Clusters by Cominational Design and Assembly", Nature Biotechnology, Advance Online Publication; XP055157548, Nov. 24, 2014, 1-12.

Woodruff, et al., "Registry in a Tube: Mutliplexed Pools of Retrievable Parts for Genetic Design Space Exploration", Nucleic Acids Research, vol. 45, No. 3; pp. 1553-1565, XP055422597, Dec. 21, 2016, 1-13.

International Search Report and Written Opinion for PCT/US2015/032760, dated Dec. 29, 2015, 12 pages.

International Preliminary Report on Patentability for PCT International Patent Application No. PCT/US2015/032760, dated Dec. 8, 2016, 8 pages.

Young, "Communication pursuant to Article 94(3) Epc," dated Nov. 5, 2018, 5 pages, For Application No. EP 15798 953.4-1118.

"EP Application No. 15798953.4, filed May 27, 2015", Communication pursuant to Article 94(3) EPC, dated Sep. 19, 2019.

Ellis, et al., "DNA Assembly for Synthetic Biology: From Parts to Pathways and Beyond", Integr. Biol., 2011, 3, 109-118, 10 pages.

Engler, et al., "A One Pot, One Step, Precision Cloning Method with High Throughput Capability", (PLoS ONE 3(11): e3647, 2008, 7 pages.

Kosuri, et al., "A Scalable Gene Synthesis Platform Using High-Fidelity DNA Microchips", Nat Biotechnol. Dec. 2010 ; 28(12): 1295-1299. doi:10.1038/nbt.1716., 13 pages.

Nielsen, et al., "Advances in genetic circuit design: novel biochemistries, deep part mining, and precision gene expression", Current Opinion in Chemical Biology 2013, 17:878-892, 15 pages.

Sarrion-Perdigones, et al., "GoldenBraid: An Iterative Cloning System for Standardized Assembly of Reusable Genetic Modules", PLoS ONE 6(7): e21622, 2011, 11 pages.

Weber, et al., "A Modular Cloning System for Standardized Assembly of Multigene Constructs", PLoS ONE 6(2): e16765, 2011, 11 pages.

"Summons to attend oral proceedings pursuant to Rule 115(1) EPC", Jun. 16, 2020, 7 pages.

\* cited by examiner

FIGURE 15
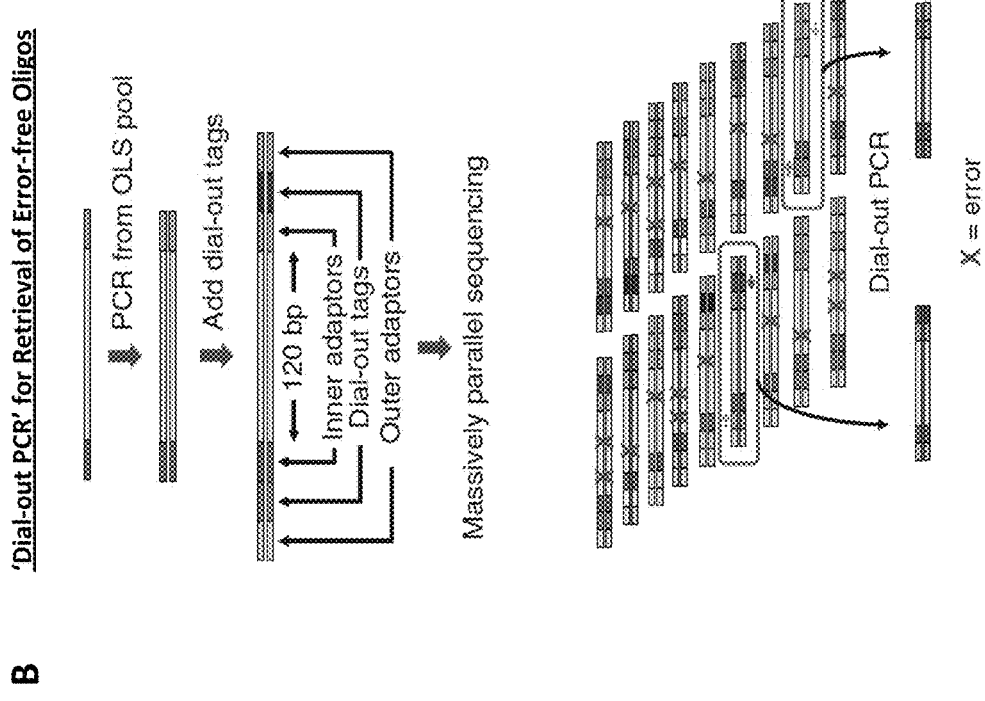
B 'Dial-out PCR' for Retrieval of Error-free Oligos
Schwartz, et al. *Nat Meth.* (2012) Prior Art
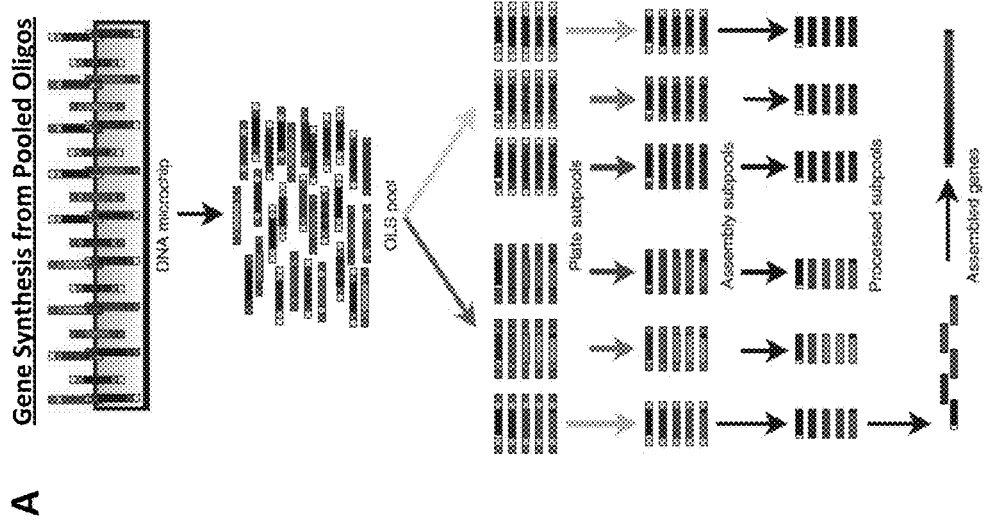
A Gene Synthesis from Pooled Oligos
Kosuri, et al. *Nat Biotech.* (2010) Prior Art

FIGURE 18

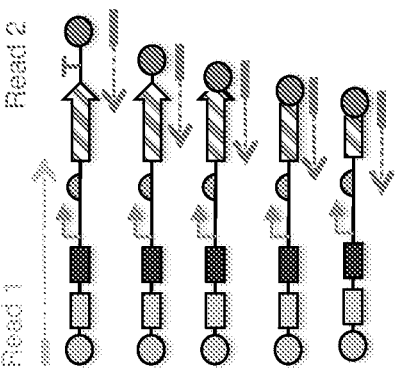

For each tagged cistron:

1. Multiplex 'Jumping' Libraries
   - Any length designs
   - In development
   - Universal and NGS compatible 2. Primer Walking Amplification
   - ≤2kb designs
   - Requires fixed positions/linkers
   - Relatively easy for cistrons
   - Not universally applicable 3. Single-Molecule Long Reads (SMRT)
   - ≤5-8kb designs
   - Universal if 2° structure ok
   - Will test on cistron pools

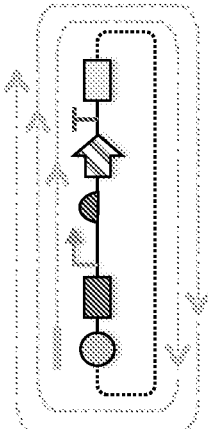

RCA PacBio Sequencing

FIGURE 29

1. Whole *nif* cluster 16 unique cistrons, 21 kb

2. Max scar set with short parts 31 unique parts, 1 kb

3. Reaction conditions combinatorial optimization

FIGURE 31
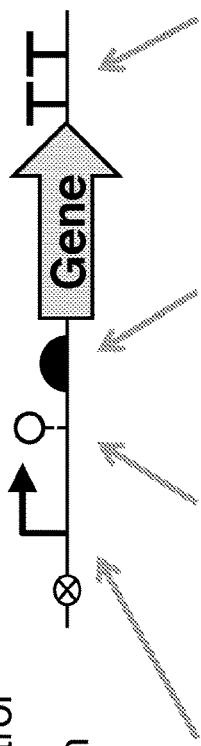
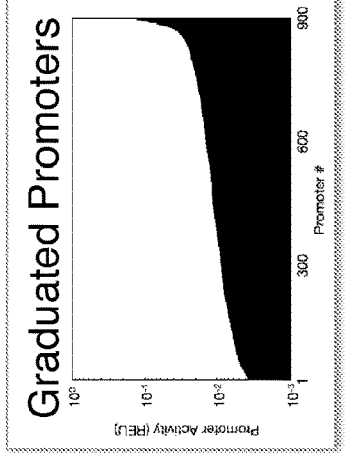
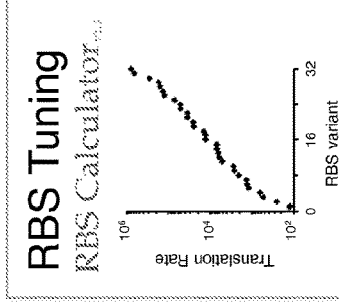
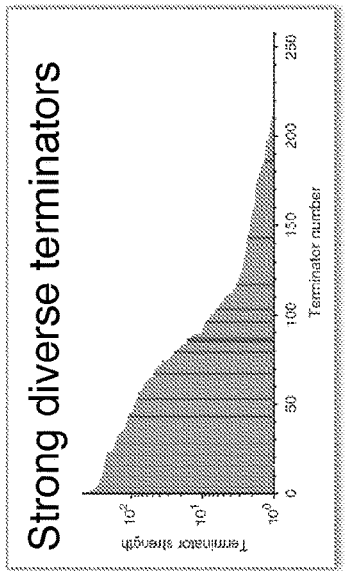

FIGURE 33
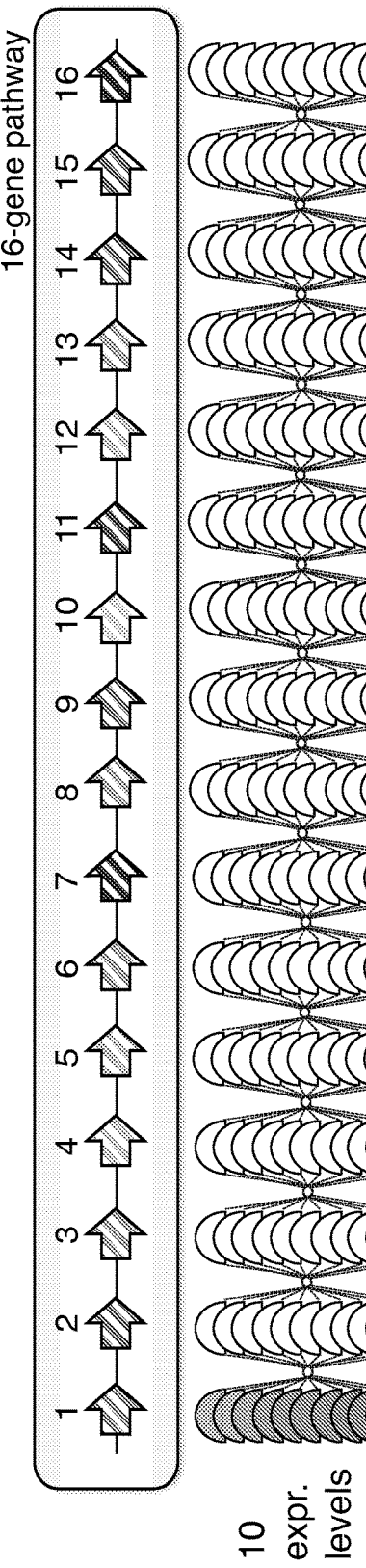
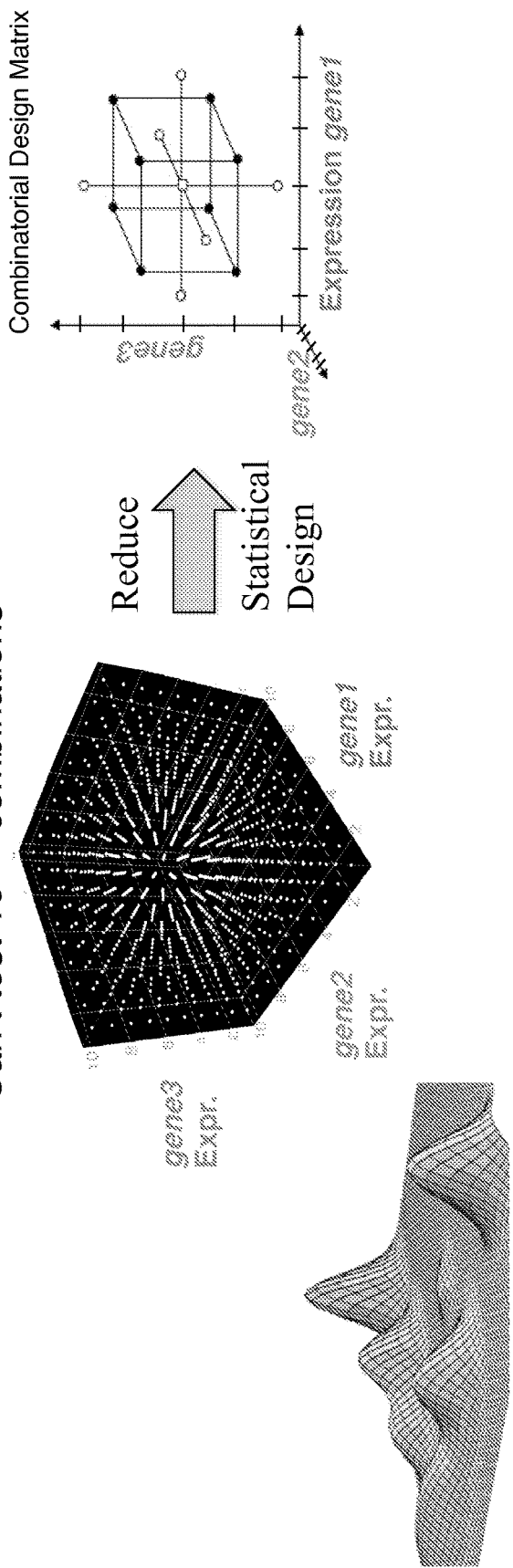

Rapid iterative permuting of multi-gene pathway

192 Systematically permuted *nif* clusters (4.5 Mb)

FIGURE 43
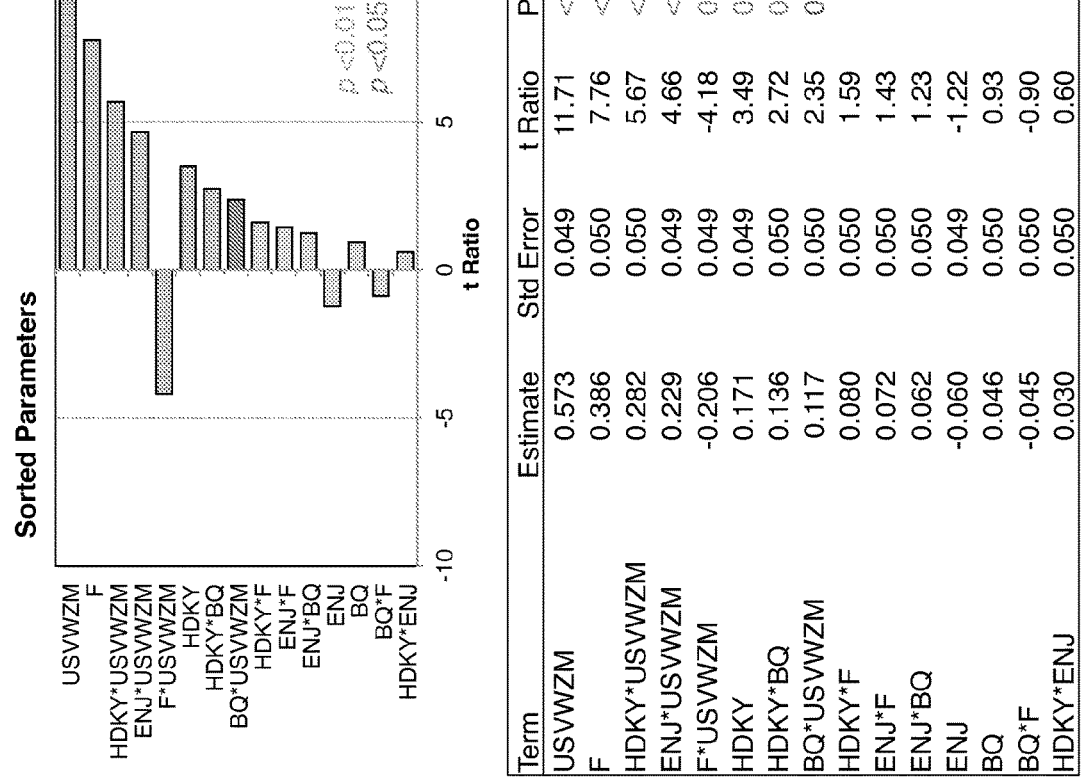
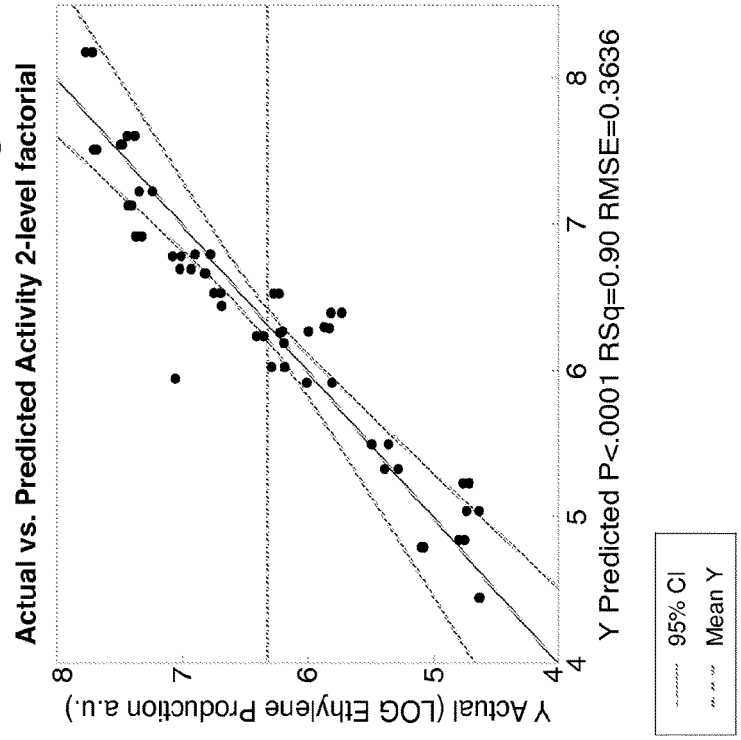

Mapped cluster activity to genetic designs

Multidimensional response surface resolved by DOE

HIGH-THROUGHPUT ASSEMBLY OF GENETIC ELEMENTS

CROSS REFERENCE TO RELATED APPLICATION

This application is the U.S. National Stage of International Application No. PCT/US2015/032760, filed May 27, 2015, which claims the benefit of U.S. Provisional Application No. 62/003,331, filed May 27, 2014, all of which are herein incorporated by reference in their entirety.

STATEMENT OF GOVERNMENT SUPPORT

This invention was made with government support under Contract No. HR0011-12-C-0067 and Contract No. HR0011-13-1-0001 awarded by the Defense Advanced Research Projects Agency. The government has certain rights in the invention.

FIELD

The present disclosure relates to methods for high-throughput assembly and sequence verification of nucleic acid constructs.

BACKGROUND

The field of synthetic biology applies the principles of engineering and rational design to the design and construction of biological systems. DNA-encoded functional units, such as genes or regulatory elements, can be abstracted into interchangeable "parts," which can be assembled in new combinations to produce new genetic designs. For example, BioBricks™ are modular segments of DNA flanked by standardized sequences, enabling assembly of BioBrick™ concatemers by standard restriction digest/ligation methods.

The cost and turnaround time of DNA assembly remains comparatively high, limiting the rate at which genetic designs can be constructed and optimized. Furthermore, the assembly of large constructs of DNA (for example, 1000+ base pairs) remains an error prone process. Thus, there is a need in the art for high-throughput methods that combine efficient and inexpensive DNA assembly with sequence verification, thus permitting rapid, inexpensive prototyping and iteration of genetic designs.

SUMMARY OF THE DISCLOSURE

Disclosed are methods for generating a set of nucleic acid elements for the combinatorial construction of a genetic design. Embodiments of the disclosed method include: providing a plurality of nucleic acid parts, comprising one or more categories of nucleic acid parts; assembling the nucleic acid parts to form one or more nucleic acid elements, wherein the nucleic acid elements comprise at least two sequences selected from the plurality of nucleic acid parts; and assembling onto the nucleic acid elements or parts a 3' and/or a 5' flanking nucleic acid sequence that orders assembly of higher-order nucleic acid constructs, facilities retrieval and/or identification of the nucleic acid element. In some embodiments, the nucleic acid parts further comprise one or more nucleic acid assembly sequences that order assembly. In some embodiments, the nucleic acid assembly sequence comprises one or more restriction sites and, prior to assembly, they are cleaved to produce sticky ends to facilitate assembly. In some embodiments, the 3' and/or 5' flanking sequences comprise one or more restriction sites and, prior to assembly, they are cleaved with restriction enzymes to produce sticky or blunt ends to facilitate assembly. In some embodiments, the one or more restriction sites comprise at least one Type IIs restriction site. In some embodiments, cleavage of the Type IIs restriction site results in cohesive end overhangs at the 5' and 3' ends of the nucleic acid sequences such that the sequences are assembled into a continuous DNA fragment with the designed order and orientation of its components. In some embodiments, the nucleic acid parts further comprise one or more nucleic acid barcodes. In some embodiments, the 3' and/or 5' flanking sequences comprise one or more nucleic acid barcodes.

In certain embodiments, the method includes: providing a plurality of nucleic acid parts, including one or more of: a set of nucleic acid sequences comprising different promoters; a set of nucleic acid sequences comprising a set of different ribosomal binding sites; a set of nucleic acid sequences encoding a polypeptide; and/or a set of nucleic acid sequences comprising a set of different transcription terminators; assembling nucleic acid parts to form one or more nucleic acid elements, wherein the nucleic acid elements include at least two sequences selected from the plurality of parts; and determining the sequence of the nucleic acid elements (for example via nucleic acid sequencing, nucleic acid amplification, nucleic acid hybridization, or a combination thereof). In certain embodiments, two or more of the assembled nucleic acid parts in the nucleic acid element are not from the same set. In certain embodiments, two or more of the assembled nucleic acid parts in the nucleic acid element are from the same set. In some embodiments, the parts, such as the parts in the pools have variations in sequence, for example variable polypeptide or CDS sequences within a pool, for example different orthologs and homologs of a known or predicted enzyme or other function. Alternatively, different synthetic or refactored coding sequences could be varied within the assembled pools (same polypeptide but different DNA sequences due to codon redundancy). In certain embodiments, the nucleic acid element includes a functional cistron or a subunit thereof. In certain embodiments, the nucleic acid element includes a nucleic acid sequence encoding a protein. In certain embodiments, the method further includes assembling a nucleic acid barcode to the 5' and/or 3' end of the nucleic acid element. In certain embodiments, the barcodes include a sequencing adaptor. In certain embodiments, the method further includes pooling the plurality of plasmids. In certain embodiments, the barcodes include a sequencing adaptor. In certain embodiments, the barcode furthers includes universal priming sites. In certain embodiments, the barcodes further include sequence specific priming sites to facilitate retrieval. In certain embodiments, each of the barcodes further includes a unique molecular identifier. In certain embodiments, each of the barcodes includes one or more indexes, one or more sequences that enable capture and/or amplification, and/or one or more sequences that enable library construction. In certain embodiments, one or more of the set of nucleic acid sequences comprising the set of different promoters; the set of nucleic acid sequences comprising the set of different ribosomal binding sites; the set of nucleic acid sequences encoding the set of different gene products, such as polypeptides, for example proteins or fragments thereof; and the set of nucleic acid sequences comprising the set of different transcription terminators are sequence variants. In certain embodiments, one or more of the set of nucleic acid sequences comprising the set of different promoters; the set of nucleic acid sequences comprising the set of different ribosomal binding sites; the set of nucleic acid sequences encoding the set of different gene products, such as polypeptides, for example proteins or fragments thereof; and the set of nucleic acid sequences comprising the set of different transcription terminators includes at least one Type IIs restriction site and, prior to assembly, they are cleaved at the Type IIs restriction site to produce sticky ends to facilitate further assembly. In certain embodiments, the method further includes amplifying the nucleic acid elements to form a mixture of amplified nucleic acid elements, for example via polymerase chain reaction (PCR). In some examples, the method further includes inserting the nucleic acid elements into nucleic acid vectors, thereby generating a plurality of plasmids containing the nucleic acid elements. In certain embodiments, the method further includes pooling the plurality of plasmids. In certain embodiments, the method further includes determining the sequence of the nucleic acid elements via nucleic acid sequencing, nucleic acid amplification, nucleic acid hybridization, or a combination thereof. In certain embodiments, the method further includes retrieving one or more of the sequence-verified nucleic acid elements, for example from a pool of such elements.

Also disclosed is a method of generating a pool of higher-order nucleic acid constructs. The method including: retrieving two or more nucleic acid elements from the sequence-verified pool of nucleic acid elements; assembling the two or more nucleic acid elements to form one or more higher-order nucleic acid constructs; and determining the sequence of the higher-order nucleic acid constructs, thereby generating a sequence-verified pool of higher-order nucleic acid constructs. In certain embodiments, the method further includes assembling a nucleic acid barcode to the 5' and/or 3' end of the higher-order nucleic acid construct. In certain embodiments, the method further includes determining the sequence of the higher-order nucleic acid constructs via nucleic acid sequencing, nucleic acid amplification, nucleic acid hybridization, or a combination thereof. In certain embodiments, the method further includes amplifying the higher-order nucleic acid constructs to form a mixture of amplified, higher-order nucleic acid constructs. In certain embodiments, the higher-order nucleic acid construct includes two or more nucleic acid sequences encoding a protein. In certain embodiments, the method further includes inserting the higher-order nucleic acid constructs into a nucleic acid vectors, thereby generating a plurality of plasmids containing the higher-order nucleic acid constructs.

Disclosed is a set of nucleic acid elements for the combinatorial construction of genetic elements or amplification products thereof. In some embodiments the elements include one or more nucleic acid elements assembled from: a set of nucleic acid sequences comprising different promoters; a set of nucleic acid sequences comprising a set of different ribosomal binding sites; a set of nucleic acid sequences encoding a polypeptide; and/or a set of nucleic acid sequences comprising a set of different transcription terminators, wherein sequence of the nucleic acid element is determined after assembly. In some embodiments, the sequence is verified prior to assembly. In some embodiments, the sequence is verified after assembly. In certain embodiments, the nucleic acid elements include at least three sequences selected from the set of a promoters, ribosomal binding sites, coding sequences, and transcription terminators. In certain embodiments, the nucleic acid elements include at least four sequences selected from the set of promoters, ribosomal binding sites, coding sequences and transcription terminators. In certain embodiments, two or more of the assembled nucleic acid parts in the nucleic acid element are not from the same set. In certain embodiments, two or more of the assembled nucleic acid parts in the nucleic acid element are from the same set. In certain embodiments, the nucleic acid element includes a functional cistron or a subunit thereof. In certain embodiments, the nucleic acid element includes a nucleic acid encoding a protein. In certain embodiments, the sequence-verified nucleic acid elements further include a nucleic acid barcode to the 5' and/or 3' end of the nucleic acid element. In certain embodiments, one or more of the set of nucleic acid sequences comprising the set of different promoters; the set of nucleic acid sequences comprising the set of different ribosomal binding sites; the set of nucleic acid sequences encoding the set of different gene products, such as polypeptides, for example proteins or fragments thereof; and the set of nucleic acid sequences comprising the set of different transcription terminators are sequence variants. Also disclosed are a set of plasmids including the set of sequence-verified nucleic acid elements.

Further disclosed is a method of optimizing a combination of nucleic acid elements for the production of an optimum desired phenotype, the method including: retrieving a plurality of sequence-verified nucleic acid elements and/or higher-order nucleic acid constructs; assembling the retrieved sequences to construct a biological pathway assembly; testing each of the assembled biological pathway assemblies for the desired phenotype; determining which characteristic or characteristics of the assembled biological pathway contributes to the desired phenotype by comparing multiple assemblies; and based on the determination, retrieving a plurality of different sequence-verified nucleic acid elements and/or higher-order nucleic acid constructs. In one embodiment, the method further includes assembling the retrieved sequences to construct a biological pathway assembly; testing each of the of the assembled biological pathway assemblies for the desired phenotype; and repeating until a biological pathway assembly is identified that produces said optimum desired phenotype.

Further disclosed is a pool of higher-order nucleic acid constructs or amplification products thereof, including one or more nucleic acid elements. In certain embodiments, the higher-order nucleic acid constructs further include a nucleic acid barcode on the 5' and/or 3' end.

Further disclosed is a kit including a pool of sequence-verified nucleic acid elements and/or a pool of higher-order nucleic acid constructs; and a plurality of primers for retrieving one or more sequence-verified nucleic acid elements and/or higher-order nucleic acid constructs.

Further disclosed are one or more electronic files including sequence information for a pool of sequence-verified nucleic acid elements and/or a pool of higher-order nucleic acid constructs.

Further disclosed is a software package that can implement a desired design as a set of oligos for automated retrieval. The software may be guided by design of experiments algorithms (DOE), metabolic flux or protein engineering models, or genetic circuit design packages. The software may also be guided by combinatorial design algorithms.

BRIEF DESCRIPTION OF THE DRAWINGS

FIGS. 15A and 15B are flowcharts illustrating methods of tag-directed retrieval of sequence verified DNA molecules in the prior art, including (A) gene synthesis from pooled oligos (Kosuri et al., Nat. Biotechnol. 28(12): 1295-1299, 2010) and (B) dial-out PCR (Schwartz et al., Nat. Meth. 9: 913-915, 2012).

FIGS. 18A-18D are a series of graphs showing mutation frequency in PCR retrieval and means for compensating.

FIGS. 17A and 17B show mutation frequencies depending on length of construct retrieved (A) or polymerase fidelity (B). FIG. 17C shows the number of copies of template cistron retreated after a certain number of PCR cycles. FIG. 17D shows the potential sequencing capacity of the MiSeq and HiSeq platforms.

FIG. 18 is a diagram describing alternative sequencing strategies for fully sequencing cistrons and larger genetic designs.

FIG. 29 is a diagram illustrating the implementation of unique parts to determine failure modes by sequencing and possible future RSM reaction optimization.

FIG. 31 is a schematic showing how gene expression elements can be tuned by refactoring for precision gene expression.

FIG. 33 is a schematic showing the optimization of hierarchical gene expression using energy landscapes to define optima in an orthogonal array of genes.

FIG. 43 shows that multivariate modeling can be used to optimize the gene cluster design.

(FIG. 47A) Each modular DNA unit ranging from approximately 100-10,000 bp is assigned a unique DNA hash, which contains a unique identifying DNA sequence. (FIG. 47B) Each module can be a composition of discrete DNA parts or shorter DNA modules, such as a combinatorial library of transcriptional units. The DNA hash can include flanking DNA sequences used to PCR amplify a unique internal identifying DNA sequence. (FIG. 47C) The genetic composition of a large multi-modular DNA construct can be determined by sequencing the short concatenation of module hashes as opposed to the entire construct. The identifying DNA hash for each module position within a design is amplified and concatenated together into a single DNA fragment. As shown, concatenation for individual designs can be achieved by emulsion overlap extension PCR, wherein each droplet contains ≤1 DNA construct (template). In this way, identification of all parts in a large multi-module construct for millions of designs can be achieved using next-generation ("next-gen") sequencing ("NGS").

DETAILED DESCRIPTION

I. Terms

Figure 1:
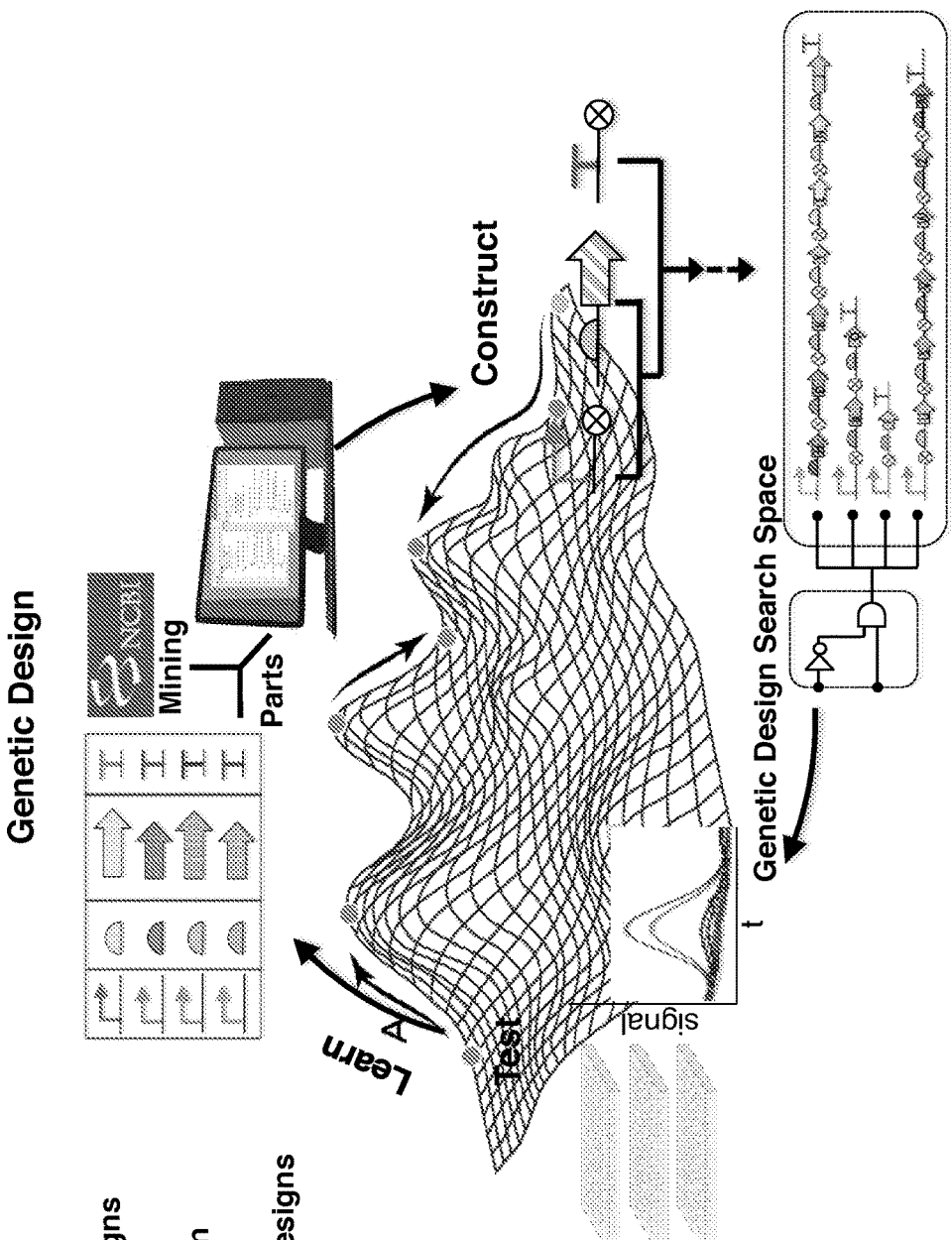
FIG. 1 is a diagram showing exemplary methods that enable the engineering of complex genetic systems on a realizable timeframe, such as through rapid, targeted combinatorial searches of relevant design space.

Unless otherwise noted, technical terms are used according to conventional usage. Definitions of common terms in molecular biology can be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710); and other similar references.

As used herein, the singular forms "a," "an," and "the," refer to both the singular as well as plural, unless the context clearly indicates otherwise. For example, the term "a nucleic acid part" includes single or plural a nucleic acid part and can be considered equivalent to the phrase "at least one a nucleic acid part."

As used herein, the term "comprises" means "includes." Thus, "a nucleic acid part" means "including a nucleic acid part" without excluding other elements.

Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments of the disclosure, the following explanations of terms are provided:

Amplification: To increase the number of copies of a nucleic acid molecule. The resulting amplification products are typically called "amplicons." Amplification of a nucleic acid molecule (such as a DNA or RNA molecule) refers to use of a technique that increases the number of copies of a nucleic acid molecule (including fragments).

An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing. An additional example of amplification is the propagation of cells harboring a vector containing an origin of replication, such as a plasmid.

Other examples of in vitro amplification techniques include quantitative real-time PCR; reverse transcriptase PCR (RT-PCR); real-time PCR (rt PCR); real-time reverse transcriptase PCR (rt RT-PCR); nested PCR; strand displacement amplification (see U.S. Pat. No. 5,744,311); transcription-free isothermal amplification (see U.S. Pat. No. 6,033,881, repair chain reaction amplification (see WO 90/01069); ligase chain reaction amplification (see European patent publication EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134) amongst others.

Antibody: A polypeptide including at least a light chain and/or heavy chain immunoglobulin variable region (or fragment thereof) which specifically recognizes and binds an epitope of an antigen, such as a protein, or a fragment thereof. Antibodies can include one or more of a heavy and a light chain, each of which has a variable region, termed the variable heavy (VH) region and the variable light (VL) region. The term also includes recombinant forms such as chimeric antibodies (for example, humanized murine antibodies), heteroconjugate antibodies (such as, bispecific antibodies). An antibody or fragment thereof may be multispecific, for example, bispecific. Antibodies include all known forms of antibodies and other protein scaffolds with antibody-like properties. For example, the antibody can be a monoclonal antibody, a polyclonal antibody, human antibody, a humanized antibody, a bispecific antibody, a monovalent antibody, a chimeric antibody, a single chain antibody (scab), a nanobody, a diabody, an immunoconjugate, or a protein scaffold with antibody-like properties, such as fibronectin or ankyrin repeats. The antibody can have any of the following isotypes: IgG (for example, IgG1, IgG2, IgG3, and IgG4), IgM, IgA (for example, IgA1, IgA2, and IgAsec), IgD, or IgE.

In most mammals, including humans, whole antibodies have at least two heavy (H) chains and two light (L) chains connected by disulfide bonds. Each heavy chain includes a heavy chain variable region ($V_H$) and a heavy chain constant region ($C_H$). However, single chain $V_{HH}$ variants, such as found in camelids, and fragments thereof, are also included. The heavy chain constant region includes three domains, $C_H1$, $C_H2$, and $C_H3$ and a hinge region between $C_H1$ and $C_H2$. Each light chain includes a light chain variable region ($V_L$) and a light chain constant region. The light chain constant region includes the domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen.

Included are intact immunoglobulins and the variants and binding portions of them well known in the art, such as Fab fragments, Fab' fragments, F(ab)'$_2$ fragments, single chain Fv proteins ("scFv"), and disulfide stabilized Fv proteins ("dsFv") Fd, Feb, or SMIP. An antibody fragment may be, for example, a diabody, triabody, affibody, nanobody, aptamer, domain antibody, linear antibody, single-chain antibody, or multispecific antibodies formed from antibody fragments. Examples of antibody fragments include: (i) a Fab fragment: a monovalent fragment consisting of $V_L$, $V_H$, $C_L$, and $C_H1$ domains; (ii) a F(ab')$_2$ fragment: a bivalent fragment including two Fab fragments linked by a disulfide bridge at the hinge region; (iii) a Fd fragment: a fragment consisting of $V_H$ and $C_H1$ domains; (iv) a Fv fragment: a fragment consisting of the $V_L$ and $V_H$ domains of a single arm of an antibody; (v) a dAb fragment: a fragment including $V_H$ and $V_L$ domains; (vi) a dAb fragment: a fragment consisting of a $V_H$ domain or a $V_{HH}$ domain (such a Nanobody™); (vii) a dAb fragment: a fragment consisting of a $V_H$ or a $V_L$ domain; (viii) an isolated complementarity determining region (CDR); and (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, for example, by a synthetic linker that enables them to be made as a single protein chain in which the $V_L$ and $V_H$ regions pair to form monovalent molecules (known as single chain Fv (scFv)). Antibody fragments may be obtained using conventional techniques known to those of skill in the art, and may, in some instances, be used in the same manner as intact antibodies. Antigen-binding fragments may be produced by recombinant DNA techniques or by enzymatic or chemical cleavage of intact immunoglobulins. An antibody fragment may further include any of the antibody fragments described above with the addition of additional C-terminal amino acids, N-terminal amino acids, or amino acids separating individual fragments.

An antibody may be referred to as chimeric if it includes one or more variable regions or constant regions derived from a first species and one or more variable regions or constant regions derived from a second species. Chimeric antibodies may be constructed, for example, by genetic engineering. A chimeric antibody may include immunoglobulin gene segments belonging to different species (for example, from a mouse and a human).

A human antibody refers to a specific binding agent having variable regions in which both the framework and CDR regions are derived from human immunoglobulin sequences. Furthermore, if the antibody contains a constant region, the constant region also is derived from a human immunoglobulin sequence. A human antibody may include amino acid residues not identified in a human immunoglobulin sequence, such as one or more sequence variations, for example, mutations. A variation or additional amino acid may be introduced, for example, by human manipulation. A human antibody of the present disclosure is not chimeric.

Antibodies may be humanized, meaning that an antibody that includes one or more complementarity determining regions (for example, at least one CDR) substantially derived from a non-human immunoglobulin or antibody is manipulated to include at least one immunoglobulin domain having a variable region that includes a variable framework region substantially derived from a human immunoglobulin or antibody or includes framework region residues of non-human origin that includes residues that have been replaced by less immunogenic residues more common in comparable human framework regions.

Genetic part: Any unit of DNA with a proscribed beginning and end and nucleotide sequence.

Assembly, concatemerization, or DNA assembly: The process of constructing a DNA concatemer by joining one or more DNA parts to each other, according to the methods of the disclosure. Examples of DNA assembly include ligation of DNA parts and ligation-independent methods, such as in vitro recombination, overlap extension PCR, round-the-horn PCR mutagenesis, ligation-independent cloning, and homologous recombination. The assembly may be constructed in stepwise fashion by adding one part to a growing concatemer per reaction, or may be assembled in a single reaction using "one-pot" assembly methods as described herein. DNA assemblies constructed according to the methods of the disclosure can be used as parts in further assembly reactions. Exemplary assemblies include higher-order parts, cistrons (for example, cistrons encoding antibodies or other polypeptides), cistron concatemers, and cistron clusters.

Category of part: A group of parts that share a defined structure and/or function. For example, coding DNA sequences ("CDSs") are a category of parts defined as DNA sequences that encode a polypeptide or a non-coding RNA. A category of parts may be designed such that variants thereof are flanked by one or two characteristic scar sequences, such that they ligate specifically with other pre-defined categories of parts (for example, a different category of parts or the same category of parts). A given DNA part may belong to more than one category of part. For example, a cistron concatemer, defined as any concatemer of more than one cistron, may also be an operon (in which the cistrons are transcribed together in a single transcript) or cistron cluster (in which the complete set of cistrons encodes a set of polypeptides that, together, perform a desired function, for example, biosynthesis pathway components).

Cistron: a series of genetic elements (for example, one of more of the following: promoters, 5' untranslated regions, ribosomal binding sites, coding regions, introns, exons, 3' untranslated regions, terminators, scars, enhancers, silencers, and/or any combination thereof) present on a single DNA strand. A cistron will generally be a gene containing a plurality of the genetic elements listed above, ordered in such a way that when it is transcribed into RNA, the resultant transcriptional product has a biological function or activity, such as an mRNA that can be translated into a polypeptide (for example, a protein, domain, antibody, or fragment thereof) or splice variants thereof, or a non-coding RNA (ncRNA) that can be processed into, for example, snoRNAs, microRNAs, siRNAs, snRNAs, exRNAs, piR-NAs, and long ncRNAs, a ribosomal RNA (rRNA), a transfer RNA (tRNA), or incorporated into a ribozyme or other ribonucleoprotein. An operon can comprise a plurality of genes or cistrons and further comprise one or more parts or elements. The genetic elements in a cistron may be directly contiguous with each other or may be separated by stretches of DNA.

Concatemer: A polynucleotide construct including two or more pieces of nucleic acid, such as DNA, attached to each other. The pieces of nucleic acid can be arranged, for example, in a pre-specified order or in a random order. The two or more pieces of nucleic acid may be immediately adjacent to each other or separated by, for example, spacers or scars. The two or more pieces of nucleic acid in a concatemer may be, for example, identical parts or belong to the same category of nucleic acid parts. Alternatively, the two or more pieces of nucleic acid may be, for example, different nucleic acid parts or belong to different categories of nucleic acid parts. The two or more pieces of nucleic acid may also belong to different orders of parts, such that one is a higher-order part relative to another. For example, a cistron can be attached to a cistron cluster, a promoter can be attached to a cistron, or a terminator can be attached to a concatemer of cistron components. Alternatively, the two or more nucleic acid pieces may belong to the same order of parts (for example, a promoter attached to an RBS, an RBS attached to a CDS, a CDS attached to a terminator, or a cistron attached to another cistron).

Covalently linked: Refers to a covalent linkage between atoms by the formation of a covalent bond characterized by the sharing of pairs of electrons between atoms. In one example, a covalent link is a bond between an oxygen and a phosphorous, such as phosphodiester bonds in the backbone of a nucleic acid strand.

Detectable label: A compound or composition that is conjugated directly or indirectly to another molecule to facilitate detection of that molecule. Specific, non-limiting examples of labels include fluorescent tags, enzymatic linkages, and radioactive isotopes. In some examples, a label is attached to a nucleic acid to facilitate detection of the nucleic acid specifically binds. In specific examples, a detectable label includes a nucleic acid barcode, such as described herein.

DNA sequencing: The process of determining the nucleotide order of a given DNA molecule. Generally, the sequencing can be performed using automated Sanger sequencing (AB13730x1 genome analyzer), pyrosequencing on a solid support (454 sequencing, Roche), sequencing-by-synthesis with reversible terminations (ILLUMINA® Genome Analyzer), sequencing-by-ligation (ABI SOLiD®) or sequencing-by-synthesis with virtual terminators (HELISCOPE®). In some embodiments, the identity of a nucleic acid is determined by DNA or RNA sequencing. Generally, the sequencing can be performed using automated Sanger sequencing (AB13730x1 genome analyzer), pyrosequencing on a solid support (454 sequencing, Roche), sequencing-by-synthesis with reversible terminations (ILLUMINA® Genome Analyzer), sequencing-by-ligation (ABI SOLiD®) or sequencing-by-synthesis with virtual terminators (HELISCOPE®); Moleculo sequencing (see Voskoboynik et al. eLife 2013 2:e00569 and U.S. patent application Ser. No. 13/608,778, filed Sep. 10, 2012); DNA nanoball sequencing; Single molecule real time (SMRT) sequencing; Nanopore DNA sequencing; Sequencing by hybridization; Sequencing with mass spectrometry; and Microfluidic Sanger sequencing.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, in traditional Watson-Crick pairing, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or it's analog) and the DNA or RNA target. The oligonucleotide or oligonucleotide analog need not be 100% complementary to its target sequence to be specifically hybridizable. An oligonucleotide or analog is specifically hybridizable when there is a sufficient degree of complementarity to avoid non-specific binding of the oligonucleotide or analog to non-target sequences under conditions where specific binding is desired. Such binding is referred to as specific hybridization.

Isolated: An "isolated" biological component (such a nucleic acid) has been substantially separated or purified away from other biological components in the cell of the organism in which the component naturally occurs, for example, extra-chromatin DNA and RNA, proteins and organelles. The term also embraces nucleic acids prepared by recombinant expression in a host cell as well as chemically synthesized nucleic acids. It is understood that the term "isolated" does not imply that the biological component is free of trace contamination, and can include nucleic acid molecules that are at least 50% isolated, such as at least 75%, 80%, 90%, 95%, 98%, 99%, or even 100% isolated.

Nucleic acid (molecule or sequence): A deoxyribonucleotide or ribonucleotide polymer including without limitation, cDNA, mRNA, ncRNA, genomic DNA, and synthetic (such as chemically synthesized) DNA or RNA or hybrids thereof. The nucleic acid can be double-stranded (ds) or single-stranded (ss). Where single-stranded, the nucleic acid can be the sense strand or the antisense strand. Nucleic acids can include natural nucleotides (such as A, T/U, C, and G), and can also include analogs of natural nucleotides, such as labeled nucleotides. The major building blocks for polymeric nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major building blocks for polymeric nucleotides of RNA are adenosine 5'-triphosphate (ATP or A), guanosine 5'-triphosphate (GTP or G), cytidine 5'-triphosphate (CTP or C) and uridine 5'-triphosphate (UTP or U). Inosine (I) may also be incorporated into synthesized DNA or RNA.

In some examples, nucleotides include those nucleotides containing modified bases, modified sugar moieties, and modified phosphate backbones, for example as described in U.S. Pat. No. 5,866,336 to Nazarenko et al. Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methyl cytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl) uracil, 2,6-diaminopurine and biotinylated analogs, amongst others. Examples of modified sugar moieties which may be used to modify nucleotides at any position on its structure include, but are not limited to arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

Nucleic acid barcode, barcode, unique molecular identifier, or UMI: A short sequence of nucleotides (for example, DNA, RNA, or combinations thereof) that is used as an identifier for an associated molecule, such as a nucleic acid. A nucleic acid barcode or UMI can have a length of at least, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 nucleotides, and can be in single- or double-stranded form. One or more nucleic acid barcodes and/or UMIs can be attached, or "tagged," to a target molecule and/or target nucleic acid, such as the nucleic acids described herein. This attachment can be direct (for example, covalent or noncovalent binding of the barcode to the target molecule) or indirect (for example, via an additional molecule, for example, a specific binding agent, such as a nucleic acid molecule). Target nucleic acids can be labeled with multiple nucleic acid barcodes in combinatorial fashion, such as a nucleic acid barcode concatemer. DNA sequences can be tagged in this manner at 5' and/or 3' ends. Tagging of DNA sequences with multiple barcodes (for example, one 5' barcode and one 3' barcode) in combinatorial fashion can greatly expand the number of unique identifiers possible within a particular barcode pool. Barcodes can be used as parts in the assembly methods of the present disclosure, or can be produced as scars after Type IIs restriction digest and subsequent ligation.

Nucleic acid element: A nucleic acid construct or concatemer made from two or more nucleic acid parts, for example an assembly, such as an ordered assembly, of two or more nucleic acid parts.

Nucleic Acid Part, Nucleic Acid Expression Part, Part, or DNA part: A sequence of nucleic acids, such as RNA or DNA, that can be concatemerized with other nucleic acid parts to form a desired assembly. Exemplary parts include: barcodes, restriction sites (for example, Type IIs restriction enzyme sites), scars/cohesive ends, promoters, spacers, ribosomal binding sites (RBS), polypeptide-encoding sequences (coding region or CDS), cis-acting regulatory elements (for example, enhancers, silencers, or insulators), splice sites, 5' untranslated regions (UTRs), 3' UTRs, DNA sequences encoding one or more non-coding RNAs (for example, tRNAs, rRNAs, snoRNAs, microRNAs, siRNAs, snRNAs, exRNAs, piRNAs, or ncRNAs), genes, cistrons, cistron concatemers, cistron clusters, operons, DNA assemblies, or any combination thereof.

Order: The complexity of the parts used in, for example, an assembly method of the present disclosure. "First-order parts" are parts constructed by traditional DNA cloning or synthesis techniques (for example, de novo synthesis, polymerase chain reaction, restriction digest, or any other common method of producing DNA fragments as known in the art). Examples of first-order parts may include barcodes, restriction sites (for example, Type IIs restriction enzyme sites), scars/cohesive ends, promoters or promoter fragments (including but not limited to naturally occurring or genetically engineered promoters, including but not limited to a transcription start site, transcription factor binding site, enhancer element and/or repressor element), spacers, ribosomal binding sites (RBS), polypeptide-encoding sequences (coding region or CDS), cis-acting regulatory elements (for example, enhancers, silencers, or insulators), splice sites, 5' untranslated regions (UTRs), 3' UTRs, DNA sequences encoding one or more non-coding RNAs (ncRNAs), for example, tRNAs, rRNAs, snoRNAs, microRNAs, siRNAs, snRNAs, exRNAs and/or piRNAs. A DNA assembly built from first-order parts using, for example, the methods of the present disclosure is a first order assembly. Exemplary first-order assemblies include CDSs, cistrons, antibody-encoding sequences, or fragments thereof. A part that is itself constructed of, for example, first-order parts is a "second-order part," and is "higher-order" relative to a first-order part. A higher-order part can be constructed from parts of any lower order (for example, a third-order part can be constructed from any combination of first- or second-order parts). Thus, nth-order parts are those constructed from, for example, any number of and/or combination of (n-x)th order parts, in which x can be 1 or greater (for example, 1, 2, 3, 4, 5, 6, 7, 8, 9, or 10).

Primers: Short nucleic acid molecules, such as a DNA oligonucleotide, for example sequences of at least 6 or more nucleotides, or at least 15 nucleotides, wherein one skilled in the art will understand that the primer length depends upon the complexity of the nucleotide target population that it will probe as well as upon hybridization conditions, and which can be annealed to a complementary nucleic acid molecule by nucleic acid hybridization to form a hybrid between the primer and the nucleic acid strand. A primer can be extended along the nucleic acid molecule by a polymerase enzyme. Therefore, primers can be used to amplify a nucleic acid molecule, wherein the sequence of the primer is specific for the nucleic acid molecule, for example so that the primer will hybridize to the nucleic acid molecule under very high stringency hybridization conditions. The specificity of a primer increases with its length. Thus, for example, a primer that includes 30 consecutive nucleotides will anneal to a sequence with a higher specificity than a corresponding primer of only 15 nucleotides. Thus, to obtain greater specificity, probes and primers can be selected that include at least 6, 15, 20, 25, 30, 35, 40, 45, 50 or more consecutive nucleotides.

In particular examples, a primer is at least 6 nucleotides in length, such as at least 6 contiguous nucleotides complementary to a nucleic acid molecule. Particular lengths of primers that can be used to practice the methods of the present disclosure, include primers having at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, or more contiguous nucleotides complementary to the target nucleic acid molecule to be amplified, such as a primer of 6-60 nucleotides, 15-50 nucleotides, or 15-30 nucleotides.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction. PCR primer pairs can be derived from a known sequence, for example, by using computer programs intended for that purpose such as Primer (Version 0.5, © 1991, Whitehead Institute for Biomedical Research, Cambridge, MA).

Methods for preparing and using primers are described in, for example, Sambrook et al. (1989) *Molecular Cloning: A Laboratory Manual*, Cold Spring Harbor, New York; Ausubel et al. (1987) *Current Protocols in Molecular Biology*, Greene Publ. Assoc. & Wiley-Intersciences. In one example, a primer includes a label.

Restriction site: A DNA sequence that includes both the recognition site and cleavage site for a restriction enzyme (for example, a Type IIs restriction enzyme). The cleavage site may be located within the recognition site or may be separated from the recognition site by one or more nucleotides. The cleavage site may be cut at the same position on both strands, thus yielding a "blunt end" with no overhanging single-stranded regions, or may be cut at different positions on each strand, thus yielding "sticky ends" with overhangs.

Recognition site: The sequence of nucleotides recognized by a restriction enzyme (for example, a Type IIs restriction enzyme). Recognition sites for restriction enzymes may contain the cleavage site for the enzyme or may be separated from the cleavage site by one or more nucleotides. In either case, the recognition site dictates the location of enzymatic cleavage by the restriction enzyme.

Retrieval, Retrieve, or Retrieving: refer to the process of isolating one or more desired DNA concatemers from a mixture or pool of DNA concatemers. Exemplary retrieval methods include polymerase chain reaction (PCR), gene synthesis from pooled oligos, or dial-out PCR. The DNA concatemers to be retrieved may be, for example, assembled from DNA parts according to the methods of the disclosure.

Generally, the DNA concatemers will be tagged with one or more DNA barcodes (for example, two DNA barcodes), the sequences of which can be used to design primers suitable for PCR retrieval and amplification.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Homologs or orthologs of nucleic acid or amino acid sequences possess a relatively high degree of sequence identity/similarity when aligned using standard methods. Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, CABIOS 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations. The NCBI Basic Local Alignment Search Tool (BLAST) (Altschul et al., *J. Mol. Biol.* 215: 403-10, 1990) is available from several sources, including the National Center for Biological Information (NCBI, National Library of Medicine, Building 38A, Room 8N805, Bethesda, MD 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (i.e., 15÷20*100=75).

Type IIs restriction enzyme: A restriction enzyme that cuts DNA at a site separated from its recognition site by a defined distance, for example, 1, 2, 3, 4, 5, 6, 7, 8, 9, or 10 nucleotides. Generally, for a Type IIs restriction enzyme, each of the nucleotides present between the recognition site and the cleavage site, and within the cleavage site itself, may be any nucleotide. A Type IIs restriction enzyme may cleave both DNA strands at a position equidistant from the recognition site, leaving a blunt end. Alternatively, a Type IIs restriction enzyme may cleave each DNA strand at a different position relative to the recognition site, leaving a "sticky end" containing a single-stranded overhang sequence, for example, an overhang sequence having a length of 1, 2, 3, 4, 5, 6, 7, 8, 9, or 10 nucleotides. Preferably, the overhang sequence is 4 nucleotides in length, for example, a 4 nucleotide overhang. Blunt ends or sticky ends left after Type IIs restriction digest can be ligated with complementary DNA ends (for example, the other end cleaved off in the digestion reaction, or another end generated by a similar digestion reaction). The sequence of nucleotides present in the overhang sequence can be used for ordered assembly of parts according to the methods of the present disclosure. Exemplary Type IIs restriction enzymes include BbsI, BsaI, and MlyI.

Variant, Variant of a part, or Variant of parts: is meant members of a category of parts that differ, for example, in sequence, length, or any other aspect of nucleic acid structure. Variants of a given part may be interchangeable in a given location within a DNA assembly. Variants of a given part may also be flanked by one or two characteristic scar sequences, such that a plurality of variants of the part (for example, all variants of the part) ligate specifically with members of other pre-defined categories of parts. Variants of an individual part can have, for example, 70, 80, 90, 95, 99, or more sequence identity.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999. In addition, the materials, methods, and examples are illustrative only and not intended to be limiting.

II. Introduction

The present disclosure provides methods for engineering complex genetic systems in a realizable time frame. Disclosed herein are methods for streamlined DNA assembly as well as sequence verification and retrieval thereof. Specifically, the disclosure features efficient and high-throughput assembly of many genetic designs from modular "parts," which can be tagged with unique barcodes and sequence verified using, for example, next-generation sequencing technologies. In some embodiments, the sequence is verified prior to assembly. In some embodiments, the sequence is verified after assembly. Desired sequence-verified permutations can be subsequently retrieved by, for example by using tag-directed PCR retrieval techniques. Thus, the present disclosure allows for large libraries of high-fidelity permuted designs to be assembled, verified, tested, and retrieved in short order, permitting rapid and inexpensive iterative search of a genetic design space of interest.

The present disclosure provides methods to modularize and optimize multi-gene pathways and/or biological systems in iterative fashion, thus increasing the size and complexity of genetic systems that can be engineered. Engineering and optimizing the performance of series of multiple genetic elements and/or large multi-gene systems requires combinatorially tuning a desired biological output (for example, gene expression, gene activity, rate of biosynthesis, biological pathway activity, and reduction in minimal required parts) through many design iterations.

Engineering genetic systems (for example, multiple genes, pathways, or proteins), can involve chemically ligating a specified set of members, such as designed DNA parts, to construct whole complex designs. Making large sets of combinations with multiple parts in each design can be a laborious and expensive process using traditional techniques. Thus, the number of specified designs that can be constructed is limited. Large, diverse libraries can be constructed in multiplex (for example, all in one solution), but individually testing a specified design in the library requires individually reconstructing that design.

The new high-throughput DNA assembly strategies disclosed herein leverage next-generation sequencing (NGS) to speed this process and enable statistical combinatorial design for targeted searches through the high-dimensional space of possible genetic designs. By assembling and sequencing designs in multiplex, this approach enables a whole new scale of genetic design (for example, an increase in library size of at least 100-fold to 1000-fold). Thus, the methods disclosed herein can be used, for example, to make large sets of any DNA composites either all combinations from set of parts with designed pairings or many entirely distinct designs with little homology at the assembly junctions using different cloning methods. In certain embodiments, there may be a set of specified permutations for each design, or permutations may be generated randomly. Design permutations can, for example, involve varying parts and/or the sequences of such parts, such as cistron components, cistrons, or concatemers thereof, to produce constructs in combinatorial fashion, which can in turn be experimentally tested. The constructs can, for example, exhibit high fidelity and can be sequence-verified by methods disclosed herein. Once a set of designs have been tested, the results can be used to navigate the genetic design search space and determine whether the experiments, points, and/or designs should be revised or redesigned for iterative improvement in the next design cycle. For example, many permutations of a particular category of parts can be iteratively inserted into a desired framework, sequence-verified, and tested in succession, with the selection of future permutations based on the performance of previously-tested permutations. The methods of the disclosure permit the use of large libraries of permuted designs (for example, at least 500 to 1000 designs per design cycle). This strategy can be applied to any combinatorial search (for example, searching a system of at least 2, 3, 4, 5, 6, 7, 8, 9, 10, 11, 12, 13, 14, 15, or 16 dimensions).

The methods described herein provides the capability to efficiently create any assembly from the full combinatorial space described by the product of every potential permutation of 1 through m genetic parts into a set of modules and further assembling every combination of these modules from 1 through n into an assembly as described by the multiplicative product below:

Library=k=1ni=1mPartik
where Library is the total library size, Part is the individual part type, m is the set of parts in a given module, n is the set of modules.

Furthermore the method enables the high throughput retrieval of any part in this library via a minimal set of steps where each assembly using traditional pairwise methods would have required
inn−1i
steps, this novel method enables a reduction in steps, all compatible with robotic automation of only n−1 steps.

III. Description of Several Exemplary Embodiments

A. High-Throughput DNA Assembly for Combinatorial Design

Disclosed are methods for generating a set of nucleic acid elements for the combinatorial construction of a genetic design. Embodiments of the disclosed method include: providing a plurality of nucleic acid parts, comprising one or more categories of nucleic acid parts; assembling the nucleic acid parts to form one or more nucleic acid elements, wherein the nucleic acid elements comprise at least two sequences selected from the plurality of nucleic acid parts; and assembling onto the nucleic acid elements or parts a 3' and/or a 5' flanking nucleic acid sequence that orders assembly of higher-order nucleic acid constructs, facilities retrieval and/or identification of the nucleic acid element. In certain embodiments, the disclosed methods involve providing a plurality of nucleic acid parts that include one or more of: a set of nucleic acid sequences comprising different promoters; a set of nucleic acid sequences comprising a set of different ribosomal binding sites; a set of nucleic acid sequences encoding a polypeptide; and/or a set of nucleic acid sequences comprising a set of different transcription terminators.

In some embodiments, a plurality of nucleic acid parts includes one or more of mammalian, insectoid, fungal, or bacterial expression elements. In one embodiment, a plurality of nucleic acid parts includes one or more of 5' UTR processing ribozyme (insulator) parts, natural repressors, phage polymerases, natural activators, sigma factors, programmable repressors, programmable activators, orthogonal ribosomes, antisense sRNA repressors, activating riboregulators, sRNA regulators converted to affect transcription, antisense RNA transcriptional attenuators, dCas9 repression, and dCas9 activation barcodes, restriction sites (for example, Type IIs restriction enzyme sites), scars/cohesive ends, promoters, spacers, ribosomal binding sites (RBSs), polypeptide-encoding sequences (coding region or CDS), cis-acting regulatory elements (for example, enhancers, silencers, or insulators), splice sites, 5' untranslated regions (UTRs), 3' UTRs, DNA sequences encoding one or more non-coding RNAs (for example, tRNAs, rRNAs, snoRNAs, microRNAs, siRNAs, snRNAs, exRNAs, piRNAs, or ncRNAs), genes, cistrons, cistron concatemers, cistron clusters, operons, DNA assemblies and those described in Nielsen et al., Current Opinion in Chemical Biology 2013, 17:878-892.

The nucleic acid parts are assembled, for example using the exemplary techniques described herein, to form one or more nucleic acid elements. These nucleic acid elements include at least two sequences selected from the plurality of nucleic acid parts. Subsequently, the sequence of the sequence of the nucleic acid elements are determined, for example by sequencing (such as NGS), amplification, hybridization or any combination thereof, thereby providing a set of sequence-verified nucleic acid elements. In certain embodiments, a nucleic acid barcode is assembled onto the 5' and/or 3' end of the nucleic acid element, for example to facilitate retrieval of the nucleic acid element from a pool of such elements, such as retrieval by amplification (for example PCR) and/or nucleic acid isolation. As disclosed herein, the assembly can be sequential or concurrent. Exemplary methods of each are given below. The assembly is typically via ligation, such as with a ligase, although chemical joining of the nucleic acids is contemplated (for example chemical joining followed by amplification such the amplification products appear identical to the amplification products of ligated nucleic acids). Methods of chemical joining and ligation are well known in the art. In some embodiments, the assembly comprises Golden Gate Assembly and/or assembly using Type IIs restriction enzymes, Gibson Assembly, restriction ligation, ligation cycling reaction, ligation independent cloning, Gateway cloning, homologous recombination, and/or iterative capped assembly.

A variety of methods can be used for nucleic acid assembly according to the methods of the present disclosure. In certain embodiments, scarless stitching methodologies are used to assemble concatemers of nucleic acids, such as DNA, parts. Scarless stitching allows for the ligation of two DNA sequences without the production of a polynucleotide "scar," an intervening sequence having, for example, a defined sequence and length (for example, a 4 nucleotide scar). As scar sequences can interfere with the activity and/or expression of the assembled design, scarless stitching is well-suited for use in assembly according to the methods of the present disclosure. Sequential rounds of scarless stitching can be used to add additional parts, such as nucleic acid parts to a growing concatemer, or to ligate two concatemers. For example, sequential rounds of scarless stitching can be used to assemble concatemers of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 40, 50, 75, or 100 parts, such as nucleic acid parts, for example nucleic acid parts. Scarless stitching methods known in the art can be used to directionally order the assembly of parts (for example, assembling parts AB and CD only in the order ABCD, and not in the orders ABDC, BACD, or DCAB). Alternatively, scarless stitching can be un-ordered (for example, ordered randomly). In certain embodiments, the parts used to construct concatemers that are of the same order. In other embodiments, the parts used to construct concatemers that are of different order (for example, some parts are higher-level relative to other parts).

One method of cloning that is useful in the disclosed method is the Golden Gate cloning method devised by Engler et al. (PLoS ONE 3(11): e3647, 2008; incorporated by reference herein in its entirety). Golden Gate cloning utilizes Type IIs restriction enzymes, which cleave DNA outside of the confines of their recognition sites. For example, BsaI binds to double-stranded DNA at the recognition sequence GGTCTC, but cleaves the DNA molecule at a four base pair (bp) region separated from the recognition sequence by one nucleotide. Thus, the complete site of action for BsaI has the sequence GGTCTC plus NWXYZ, wherein NWXYZ can be any set of five contiguous nucleotides. The enzymatic cleavage product includes one section of DNA containing the BsaI recognition sequence and the reverse complement of WXYZ left as an overhang, and a second section of DNA containing the WXYZ overhang. Notably, this second section of DNA no longer contains a BsaI recognition site. One can design a construct in which a part, such as a nucleic acid part, for example a nucleic acid part is flanked by two restriction sites, such as Type IIs restriction sites, such that cleavage will result in the removal of the recognition sites from both ends of the resultant fragment. The cohesive ends containing the Type IIs recognition site are cleaved off in this scenario. If the nucleic acid part is ligated with a similarly-constructed fragment based on overhang complementarity, the enzyme recognition site will be eliminated and the construct will no longer be cleavable by the enzyme. Thus, constructs can be designed such that only a desired ligation (for example, ligation between two parts or ligation between a part and a desired backbone or vector) results in elimination of the enzyme recognition site on both sides of the ligation junction. Undesired ligations (for example, ligation between a nucleic acid part and a cohesive end or ligation between two cohesive ends) will recreate the entirety of the Type IIs restriction site, including the recognition site, and are thus reversible reactions. Thus, the reaction can be funneled towards the desired product. Because the overhang sequences can be made of any combination of four nucleotides, the ligation junction can have any sequence desired. For example, using the first or last four nucleotides of the 3' or 5' fragment, respectively, can be used to produce a scarless junction. Alternatively, overhang sequences can be designed to intentionally introduce a 4-nucleotide scar, for example, a scar having a predefined sequence. Additional methods for assembly that can be used according to the methods of the present disclosure include, for example, BioBrick™ assembly, BglBrick assembly, overlap extension polymerase chain reaction (OE-PCR), Gibson isothermal assembly, transformation-associated recombination, pairwise selection, InFusion™, sequence- and ligation-independent cloning (SLIC), uracil-specific excision reagent (USER) cloning, *Bacillus* Domino recombination, (Ellis et al., Integr. Biol. 3: 109-118, 10 2011), Golden Braid cloning (Sarrion-Perdigones et al., PLoS ONE 6(7): e21622, 2011), and ligation based methods or homologous recombination-based methods known in the art (Merryman and Gibson, Metabol. Eng. 14: 196-204, 2012).

Figure 23:
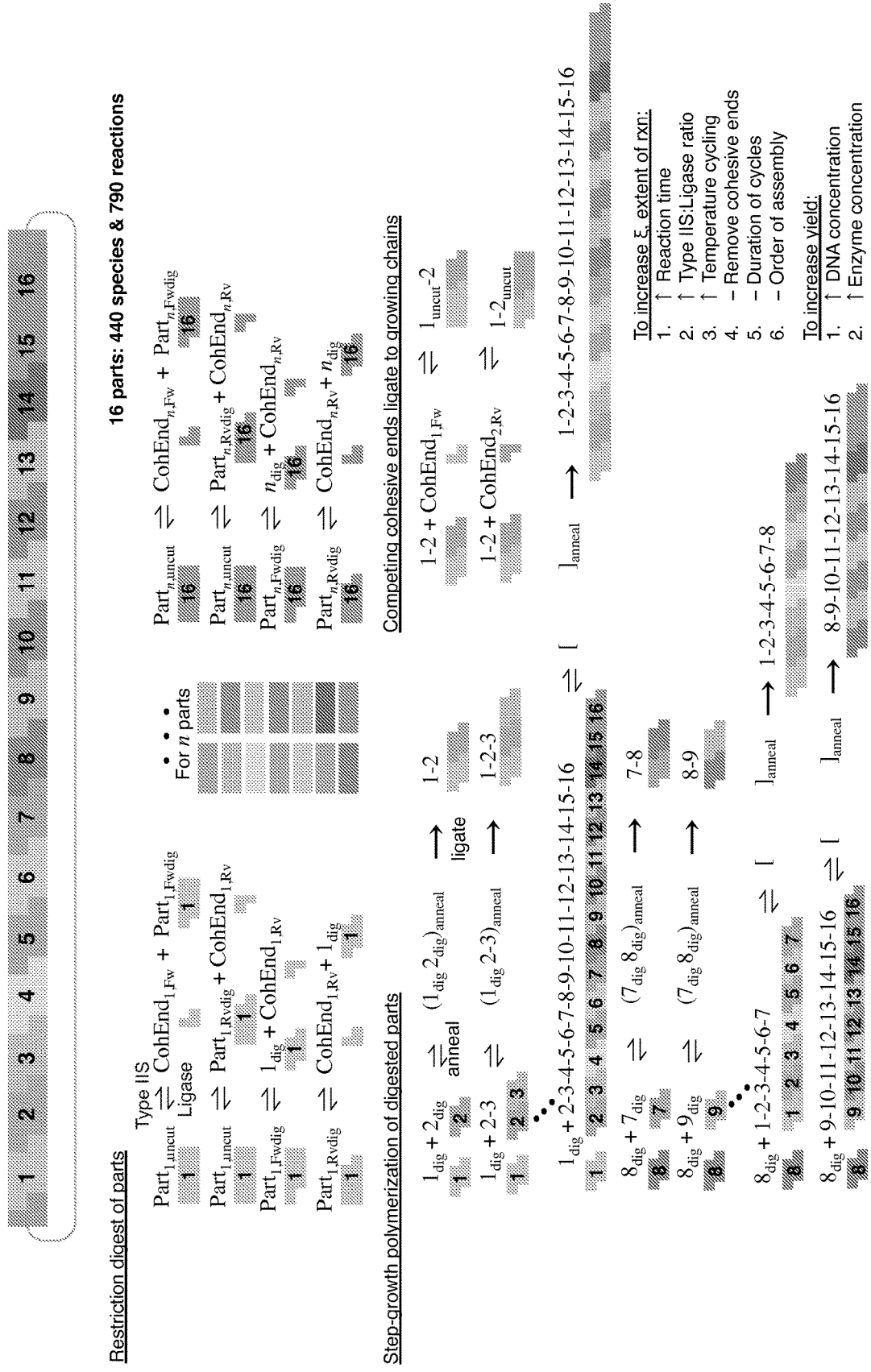
FIG. 23 is a diagram illustrating the many possible reactions occurring in a single massively one-pot restriction-ligation reaction, including restriction digest of parts, step-growth polymerization of digested parts, and ligation of competing cohesive ends to growing chains.

In certain embodiments, the present disclosure provides a refinement of the Golden Gate cloning method, in which multiple parts (for example, at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 40, 50, 75, 100, 150, 200, 250, or 256 nucleic acid parts) are digested and ligated into concatemers in a single reaction ("one-pot" assembly, illustrated in FIG. 23). The 4-bp overhang scar sequences that are produced after Type IIs restriction digest can be used as codes to direct a desired ligation between two nucleic acid parts, one having a particular 4-bp scar overhang, and the other having the reverse complement overhang. Placing Type IIs restriction sites on both 5' and 3' ends of a given part, such as a nucleic acid part allow it to be assembled to two other parts simultaneously. In certain embodiments, the one-pot reaction mixture contains: a plurality of nucleic acid, each with one or two Type IIs restriction sites flanking the nucleic acid part; one or more Type IIs restriction enzymes capable of cleaving the Type IIs restriction sites, and a ligase suitable for attaching nucleic acid parts after overhang annealing. The reaction may involve restriction digest of nucleic acid parts to produce parts containing overhangs and complementary cohesive end fragments, step-growth polymerization of digested nucleic acid parts, and competing cohesive end ligation to growing chains of nucleic acid parts. Importantly, only the concatemerization/polymerization of two nucleic acid parts, a nucleic acid part and a growing chain, or two growing chains, are irreversible due to the loss of the Type IIs recognition site. In some embodiments, one or more of the set of nucleic acid sequences comprising the set of different promoters; the set of nucleic acid sequences comprising the set of different ribosomal binding sites; the set of nucleic acid sequences encoding the set of different gene products, such as polypeptides, for example proteins or fragments thereof; and the set of nucleic acid sequences comprising the set of different transcription terminators includes at least one Type IIs restriction site and, prior to assembly, they are cleaved at the Type IIs restriction site to produce sticky ends to facilitate assembly. In some embodiments, cleavage of the Type IIs restriction site results in cohesive end overhangs at the 5' and 3' ends of the nucleic acid sequences comprising the set of different promoters; the set of nucleic acid sequences comprising the set of different ribosomal binding sites; the set of nucleic acid sequences encoding the set of different gene products, such as polypeptides, for example proteins or fragments thereof; and the set of nucleic acid sequences comprising the set of different transcription terminators such that the sequences are assembled in the corrected read order.

The extent of reaction can be increased by, for example, increasing reaction time, increasing the ratio of Type IIs enzyme to ligase, increasing the number of temperature cycles, removing cohesive ends, modulating the duration of the cycles, or modulating the order of part assembly. Reaction yield can be raised by, for example, increasing DNA concentration or increasing enzyme concentration. Golden Gate overhang sequences can further be used to specify the order in which multiple nucleic acid parts are assembled in a one-pot assembly reaction (for example, assembling parts AB, CD, and EF in the order ABCDEF). This is accomplished by employing multiple unique 4-bp overhang scar sequences. Each unique overhang sequence will only ligate with another overhang sequence of suitable sequence complementarity. Because restriction digest and ligation freely occur in the same reaction in one-pot assembly, the multiple parts can be cleaved (to produce overhangs), annealed together, and ligated in a desired order, all within a single one-pot reaction. Thus, n distinct overhang sequences can be used to simultaneously assemble n+1 distinct DNA fragments in a specified order, as demonstrated in Example 2 (see FIG. 21). For example, one-pot assembly can be used to assemble concatemers of a pre-specified order of nucleic acid parts, including at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 40, 50, 75, 100, 150, 200, 250, or 256 parts. In certain embodiments, the nucleic acid parts used to construct a concatemer are of the same order. In other embodiments, the nucleic acid parts used to construct a concatemer are of different order (for example, some nucleic acid parts are higher-level relative to other nucleic acid parts). The present disclosure further features optimized design rules for 4-bp scar sequences and improved reaction conditions that permit consistent assembly of full-length products in an ordered fashion. Exemplary design rules and reaction conditions are described in Examples 2 and 3.

In some embodiments, the nucleic acid elements include at least three sequences selected from the set of a promoters, ribosomal binding sites, coding sequences, and transcription terminators. In some embodiments, the nucleic acid elements include at least four sequences selected from the set of a promoters, ribosomal binding sites, coding sequences, and transcription terminators. In specific embodiments two or more of the assembled nucleic acid parts in the nucleic acid element are not from the same set. In some embodiments, two or more of the assembled nucleic acid parts in the nucleic acid element are from the same set. In certain embodiments, the nucleic acid element includes a functional cistron or a subunit thereof. In some embodiments, one or more of the set of nucleic acid sequences comprising the set of different promoters; the set of nucleic acid sequences comprising the set of different ribosomal binding sites; the set of nucleic acid sequences encoding the set of different gene products, such as polypeptides, for example proteins or fragments thereof; and the set of nucleic acid sequences comprising the set of different transcription terminators are sequence variants.

Nucleic acid parts that can be used in the assembly methods of the present disclosure can include any sequence of DNA, ranging in size and scale from individual components of a cistron to clusters of cistrons. Parts can range in size from less than 50 bp to greater than 8 kilobases (kb). Exemplary nucleic acid parts may have a length of about 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1 kb, 2 kb, 3 kb, 4 kb, 5 kb, 6 kb, 7 kb, 8 kb, 9 kb, or 10 kb, or a length in a range specified by any combination of the prior-listed lengths (for example, ranges between adjacent listed lengths).

Figure 11:
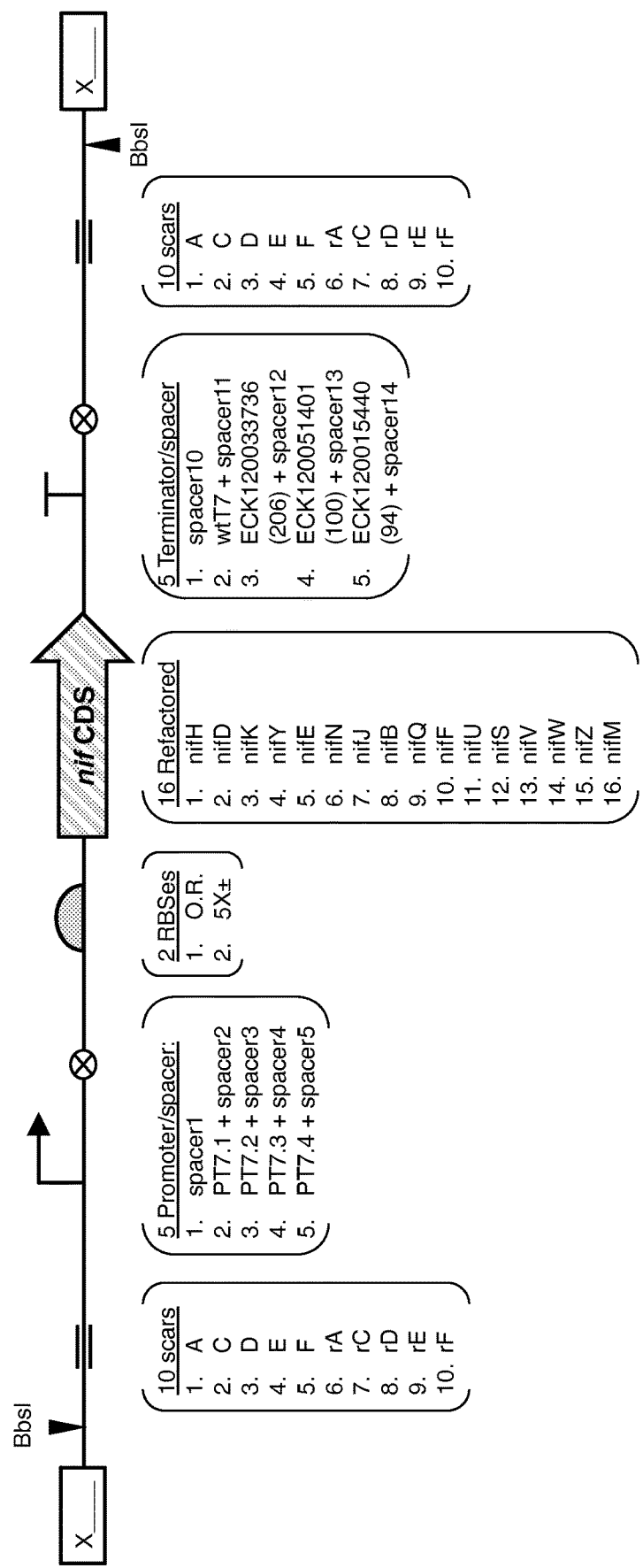
FIG. 11 is a diagram showing an assembled nif cistron and listing the set of genetic parts that can be placed at each location within the cistron.

A cistron requires certain components to be suitable for expressing a gene product in vitro or in vivo. Non-limiting examples of cistron components that can be used as nucleic acid parts in the present disclosure include one or more of any combination of the following: barcodes, restriction sites (for example, Type IIs restriction enzyme sites), scars/cohesive ends, promoters, spacers, ribosomal binding sites (RBS), and/or sequences encoding a polypeptide of interest (coding region or CDS), for example, an entire polypeptide of interest or a subset (for example, a domain). FIG. 11 depicts an exemplary cistron containing, in order from 5' to 3' end: a 5' barcode sequence, a BbsI recognition site, a scar sequence, a promoter/spacer, an RBS, a CDS, a terminator/spacer, a second scar sequence, a second BbsI recognition site, and a 3' barcode sequence. Such nucleic acid parts may be initially designed by, for example, mining a database such as NCBI to identify known parts for each desired category of nucleic acid parts, such as those listed above. The components of a cistron can vary depending on the system or organism in which it will be expressed. For example, the RBS can be a 5' cap, a Shine-Dalgarno sequence, or an internal ribosomal entry site (IRES). The CDS can include exons and/or introns, although generally it will contain coding sequences.

In some embodiments, the CDS encodes a protein (for example, an antibody). The antibody can be, for example, in any of the following forms: IgG, IgM, IgA, IgD, IgE, Fab, Fab', F(ab')2, Fd, Fv, scFv, or SMIP and/or as defined above. The antibody can be, for example, a mouse, rat, rabbit, goat, bovine, canine, chicken, donkey, feline, guinea pig, hamster, horse, monkey, sheep, or pig antibody. In certain embodiments, the antibody is, for example, a human antibody, a chimeric antibody, or a humanized antibody. Exemplary antibody components or antibody fragments that can be used as parts in the methods of the present disclosure include Fab fragments, Fc fragments, F(ab')2 fragments, Fab' fragments, Fv fragments, IgG fragments, variable domains, constant domains, heavy chains, light chains, framework sequences, antigen-binding sites, and complementarity-determining regions.

In certain embodiments, the CDS encodes a fragment of a protein, for example, a protein domain, antibody component, antibody fragment, or polypeptide. In certain embodiments, at least one of the parts encodes an antibody variable domain. In certain embodiments, at least one of the parts encodes an antibody constant domain. In certain embodiments, at least one of the nucleic acid parts encodes a protein from a biological pathway. In certain embodiments, the set of parts encodes multiple proteins from a biological pathway. In certain embodiments, the set of parts encodes all of the proteins from a biological pathway. In certain embodiments, the biological pathway includes a metabolic pathway. In certain embodiments, the metabolic pathway includes a synthetic pathway or a catabolic pathway. In certain embodiments, the biological pathway includes a genetic pathway. In certain embodiments, the biological pathway includes a signal transduction pathway; for example, synthetic genetic circuits.

Additional components that can be used as parts in methods of the present disclosure include, for example, cis-acting regulatory elements (for example, enhancers, silencers, or insulators), splice sites, 5' untranslated regions (UTRs), 3' UTRs, and/or sequences encoding one or more non-coding RNAs (ncRNAs) for example tRNAs, rRNAs, snoRNAs, microRNAs, siRNAs, snRNAs, exRNAs, and/or piRNAs. 5' UTR processing ribozyme (insulator) parts, natural repressors, phage polymerases, natural activators, sigma factors, programmable repressors, programmable activators, orthogonal ribosomes, antisense sRNA repressors, activating riboregulators, sRNA regulators converted to affect transcription, antisense RNA transcriptional attenuators, dCas9 repression, and dCas9 activation barcodes, restriction sites (for example, Type IIs restriction enzyme sites), scars/cohesive ends, promoters, spacers, ribosomal binding sites (RBS), polypeptide-encoding sequences (coding region or CDS), genes, cistrons, cistron concatemers, cistron clusters, operons, DNA assemblies and those described in Nielsen et al., Current Opinion in Chemical Biology 2013, 17:878-892.

Parts may contain epigenetic modifications (for example, DNA methylation), non-DNA nucleotides (for example, uracil), and/or nucleotide analogues. In certain embodiments, parts assembled by methods of the present disclosure can contain a single, for example, promoter, but multiple RBSs and/or encoding regions. Assembly of parts may be performed in sequential fashion, in which one nucleic acid part is added to a growing concatemer at a time, or by one-pot assembly. Alternatively, concatemers of parts (for example, a promoter and RBS) may be assembled to form a subassembly and then subsequently attached to additional parts and/or subassemblies. Parts may be assembled in a specified order or in an un-ordered (for example, randomly ordered) fashion.

In some embodiments, the methods further include amplifying the nucleic acid elements to form a mixture of amplified sets of nucleic acid elements, for example amplifying the nucleic acid elements by polymerase chain reaction (PCR). In some embodiments, the nucleic acid elements are inserted into nucleic acid vectors, for example to generate a plurality of plasmids containing the nucleic acid elements. These nucleic acid vectors can also be amplified, for example by propagation in a suitable host cell, for example under selective pressure. Examples of plasmid propagation are well known in the art and include propagation in bacterial cells such as but not limited to E. coli. Isolation of such plasmids is equally known the art. In some embodiments, the plurality of plasmids are pooled.

Particular sequence-verified nucleic acid elements assembled according to methods of the present disclosure can be readily retrieved from a pool of assembled nucleic acid elements, for example, using PCR. Thus, in certain embodiments, the disclosed methods include retrieving one or more of the sequence-verified, for example by nucleic acid amplification and/or isolation. For example, barcoded assembled nucleic acid elements can be retrieved from, for example from a pool, by using a unique set of primers that specifically hybridize the barcodes on the 5' and 3' ends of the bar coded nucleic acid elements. In some examples, multiple assembled nucleic acid elements are retrieved using primers that specifically hybridize to the barcodes. Because each assembly is flanked by a pair of unique barcodes, a given assembly may be retrieved by performing PCR using primers targeting the barcodes. Additional methods for tag-directed retrieval of sequence-verified assemblies include gene synthesis from pooled oligos (FIG. 15A; Kosuri et al., Nat. Biotechnol. 28(12): 1295-1299, 2010; US Patent Publication No. US 20140045728 A1) and dial-out PCR (FIG. 15B; Schwartz et al., Nat. Meth. 9: 913-915, 2012; US Patent Publication No. US 20120283110 A1).

Aspects of the present disclosure also concern the construction of higher-order nucleic acid constructs. Higher-order nucleic acid constructs are assemblies built from a plurality of nucleic acid elements, for example, using methods of the present disclosure. Thus, disclosed herein are methods of assembling higher-order nucleic acid constructs. The methods include retrieving two or more nucleic acid elements from the sequence-verified pool of nucleic acid elements, assembling the two or more nucleic acid elements to form one or more higher-order nucleic acid constructs, and determining the sequence of the higher-order nucleic acid constructs thereby generating a sequence-verified pool of higher-order nucleic acid constructs. Higher-order nucleic acid construct can include concatemers of multiple cistron components, cistrons, or cistron concatemers, and can include concatemers of multiple operon components, operons, operon concatemers, and can include concatemers of concatemers. One higher-order nucleic acid construct may be higher in order relative to a second higher-order nucleic acid construct if the first higher-order nucleic acid construct is, for example, an assembly of parts belonging to the same category of nucleic acid parts as the second part or an assembly of such assemblies of parts. Such higher-order nucleic acid construct can also be used in the assembly methods described herein to construct higher-order assemblies. In certain embodiments, a higher-order nucleic acid construct includes two or more nucleic acid sequences encoding a protein. In specific examples, the protein includes an antibody or an antibody fragment, such as a humanized antibody or antibody fragment. In some examples the antibody or antibody fragment is of isotype IgG, IgA, IgM, IgE, or IgD, and/or the fragment selected includes a Fab, Fab', F(ab')2, Fd, Fv, scFv, or SMIP or as provided above in the definition of an antibody.

Exemplary higher-order assemblies include cistrons, cistron concatemers, and cistron clusters as well as operons, operon concatemers and operon clusters. In certain embodiments, the higher-order assembly is an antibody (for example, a chimeric antibody or humanized antibody) or antibody fragment.

Higher-order nucleic acid constructs can be ligated with other higher-order nucleic acid construct or with lower-order parts such as those described above. Assembly of higher-order nucleic acid construct into higher-order assemblies may be performed sequentially, for example, by adding one higher-order nucleic acid construct onto a growing concatemer per reaction. Alternatively, multiple higher-order nucleic acid construct (for example, more than three higher-order nucleic acid constructs) may be assembled into a concatemer in a single reaction. In a further embodiment, parts can be added to a higher-order assembly in iterative fashion.

In certain embodiments, a plurality of cistrons can be assembled into a cistron concatemer. A cistron concatemer includes at least two cistrons (for example, at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 cistrons), and may contain all of the cistrons in a biological pathway (for example, a metabolic pathway, such as a synthetic pathway or a catabolic pathway, genetic pathway, or a signal transduction pathway, such as those described herein). The cistrons in a cistron concatemer assembled using methods of the present disclosure can be arranged in a specified order, for example, by using a unique scar sequence for each cistron junction, such that a given cistron can only ligate with one specific cistron at each end. Alternatively, the cistrons in a cistron concatemer can be arranged in an un-ordered (for example, randomly ordered) fashion. In certain embodiments, the higher-order nucleic acid construct includes two or more nucleic acid sequences encoding two or more proteins from a biological pathway.

Figure 21:
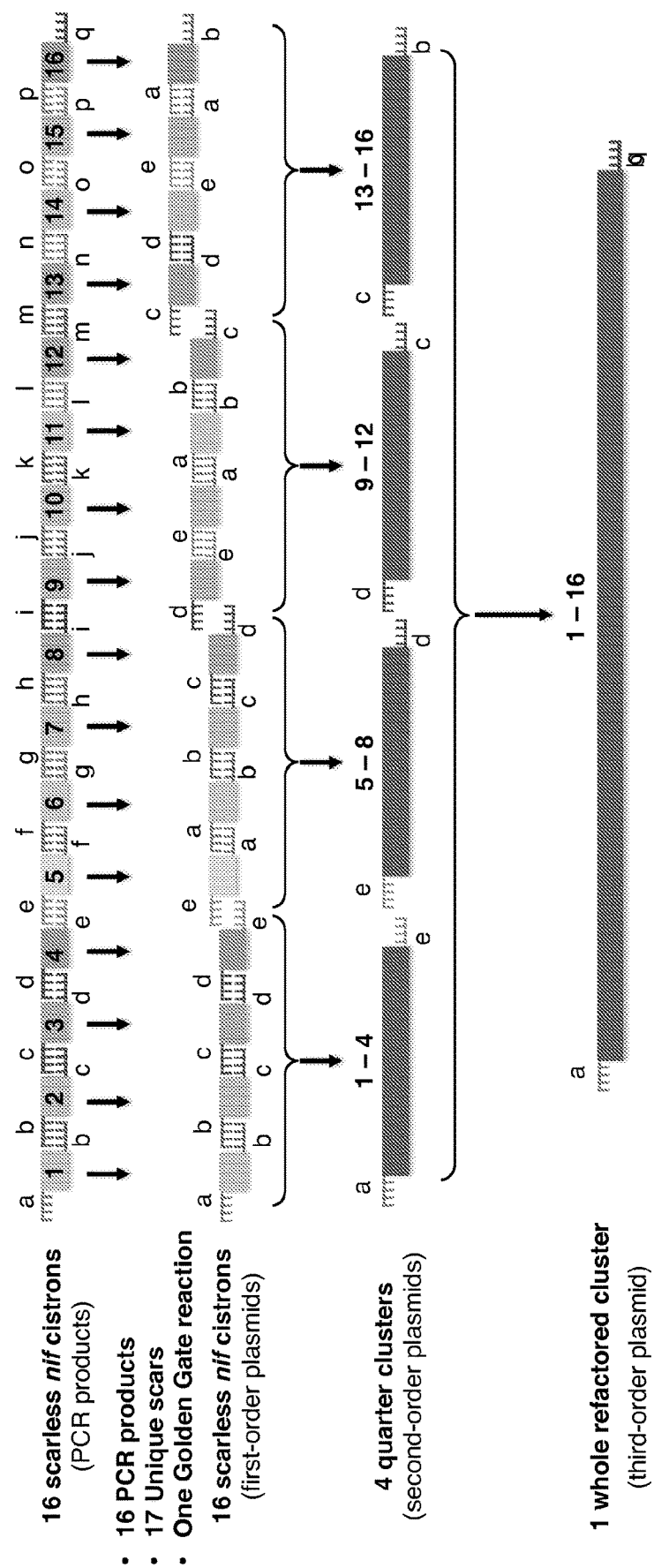
FIG. 21 is a flowchart illustrating how massively one-pot assembly can be used to reduce the steps in hierarchical cluster assembly into a series of single assembly reactions. In the example shown here, the assembly reactions produce, in turn, 16 scarless nif cistrons, four quarter clusters (1-4, 5-8, 912, and 13-16), and one whole refactored cluster (1-16).

In certain embodiments, cistron concatemers are used as higher-order nucleic acid constructs for further assembly. For example, as shown in FIG. 21, groups of cistrons can be assembled into first-order cistron concatemers by Golden Gate cloning. The first-order cistrons can be amplified, purified, excised from their plasmid backbones, and further assembled by Golden Gate cloning into second-order "quarter clusters," which are in turn ultimately assembled by Golden Gate cloning into a third-order whole cluster. It is contemplated that whole clusters can be used as higher-order nucleic acid constructs in further assembly reactions, as well.

In certain embodiments, a nucleic acid barcode is assembled to the 5' and/or 3' end of the higher-order nucleic acid construct. In some embodiments, the higher-order nucleic acid constructs are amplified, for example by PCR to form a mixture of amplified, higher-order nucleic acid constructs. In certain embodiments, the higher-order nucleic acid constructs are inserted into a nucleic acid vectors, thereby generating a plurality of plasmids containing the higher-order nucleic acid constructs.

Nucleic acid barcodes are frequently used to tag DNA, RNA, or other molecules in an identifiable way. Barcodes can be any nucleic acid sequence that may be used to identify a particular tagged molecule. Barcoding methods have been used extensively to allow parallel, multiplexing experimentation of different types of genetic alterations (see, for example, Craig et al., Nat. Methods 5: 887-893, 2008; Gerrits et al., Blood 115: 2610-2618, 2010; and Berns et al., Nature 428: 431-437, 2004). In the methods of the present disclosure, DNA barcodes are used to uniquely tag genetic designs. In some embodiments, two barcodes are attached to a DNA assembly, one at the 5' end and one at the 3' end. The use of two barcodes on the same molecule greatly increases the number of unique identifiers that can be generated using a particular barcode pool. Barcodes that can be used according to the methods of the disclosure can have a length of at least, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 bp. In some embodiments, the barcodes are chip-synthesized and reused, such that the retrieval primers can be reused across multiple libraries. Barcodes can be added to an assembled pool of genetic designs by, for example, multiplex Gibson assembly. In one embodiment, plasmids containing assembled designs are purified and emulsion multiplex PCR is performed to add desired cohesive ends and flanking adaptors to each assembly. The resultant pool of assemblies is ligated to backbone vectors containing a pair of N20 barcodes and an ampicillin resistance (AmpR) cassette, such that the barcodes flank a single assembly after ligation, with each assembly receiving a unique combination of barcodes. In certain embodiments, the barcodes can be used to retrieve a desired individual assembly from a pool. For example, two flanking barcode sequences can be used to design primers for PCR retrieval of the assembly. The primer can include a variant region corresponding to the barcodes and an invariant region that is, for example, common to the assembled parts.

DNA sequences (for example, constructs assembled according to the methods of the disclosure) can be amplified, for example, at various steps in the methods of the disclosure (for example, after assembly, after barcode tagging, prior to sequencing adaptor ligation, after sequencing adaptor ligation, or after retrieval). Methods for DNA amplification are well-understood in the art. For example, DNA sequences can be amplified by polymerase chain reaction (PCR). PCR primers can be designed based on, for example, barcode or scar sequences. PCR may be preceded by a restriction digest step that excises the target DNA from a vector. Alternatively, DNA can be amplified by, for example, transformation of cells (for example, bacteria or yeast) with, for example, a self-replicating vector (for example, a plasmid, bacterial artificial chromosome, yeast artificial chromosome, fosmid, or virus) containing the target DNA, followed by clonal expansion of the cells in a suitable growth medium. The amplified vectors can be readily purified from the cells using standard preparation techniques in the art.

The present disclosure provides methods for assembling genetic designs such that the resultant assemblies can be readily sequence verified, for example, in multiplex. In some embodiments, genetic designs assembled according to the methods of the disclosure are flanked by a pair of barcode sequences. The assembly and barcodes are, in turn, flanked by restriction sites (for example, NotI sites), thus allowing the excision of assembly and flanking barcode pair by a restriction digest. For assemblies short enough in length that sequencing from both ends would permit resolution of the entire assembly sequence (for example, assembly sequences shorter than about 0.5-1 kb), next-generation sequencing (NGS) adaptors are attached and NGS is performed. Particular sequence-verified genetic designs assembled according to methods of the present disclosure can be readily retrieved from a pool of assembled constructs, for example, by hierarchical retrieval. For example, the assembly pool can be tested using a desired assay, such as, for example, gene analysis (for example, RT-PCR, Northern blotting, Western blotting, ELISA, microarray analysis, RNA-Seq, flow cytometry, or proteomic analysis), protein activity analysis (for example, cytochrome P450 activity assays, reporter assays, enzyme-based assays, kinase assays, or phosphatase assays), measurement of biosynthetic product formation or purity, or high-throughput variants of any of the above assays.

Further disclosed is a method of optimizing a combination of nucleic acid elements for the production of an optimum desired phenotype, the method including: retrieving a plurality of sequence-verified nucleic acid elements and/or higher-order nucleic acid constructs; assembling the retrieved sequences to construct a biological pathway assembly; testing each of the assembled biological pathway assemblies for the desired phenotype; determining which characteristic or characteristics of the assembled biological pathway contributes to the desired phenotype by comparing multiple assemblies; based on the determination, plurality of sequence-verified nucleic acid elements and/or higher-order nucleic acid constructs; assembling the retrieved sequences to construct a biological pathway assembly; testing each of the of the assembled biological pathway assemblies for the desired phenotype; and repeating until a of the assembled biological pathway assemblies for the desired phenotype is identified that produces said optimum desired phenotype.

Assemblies that perform strongly in the assay may be useful to retrieve from the pool. Because each assembly is flanked by a pair of unique barcodes, a given assembly may be retrieved by performing PCR using primers targeting the barcodes. Additional methods for tag-directed retrieval of sequence-verified assemblies include gene synthesis from pooled oligos (FIG. 15A; Kosuri et al., Nat. Biotechnol. 28(12): 1295-1299, 2010; US Patent Publication No. US 20140045728 A1) and dial-out PCR (FIG. 15B; Schwartz et al., Nat. Meth. 9: 913-915, 2012; US Patent Publication No. US 20120283110 A1).

Figure 17:
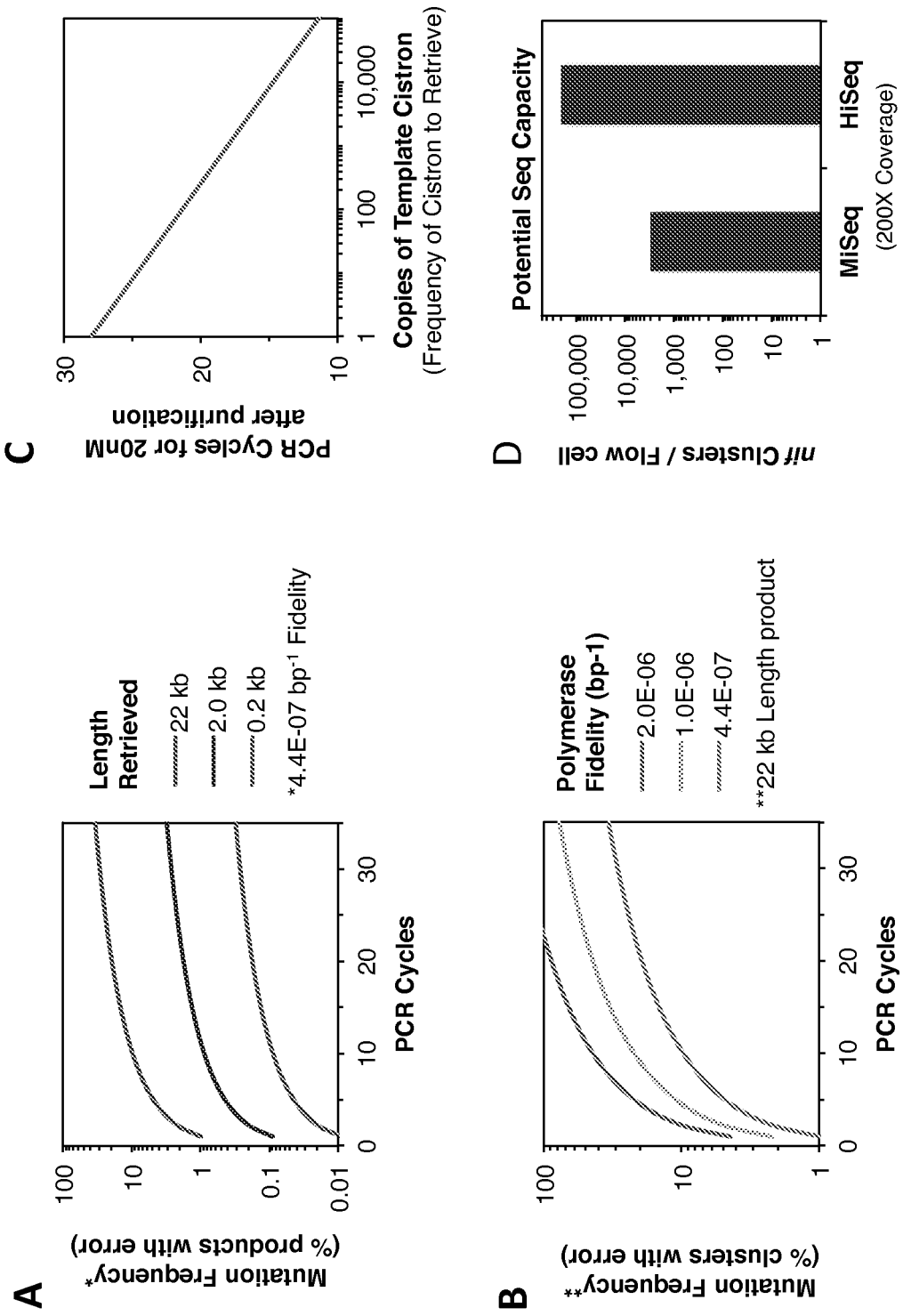
FIG. 17A-17D.

For longer assemblies, there are several possible sequencing strategies. In certain embodiments, one or more "common" parts are identical in all assemblies, such as that schematized in FIG. 10. In such cases, the assembly fragment can be self-circularized and then PCR amplified using primers directed at the ends of the common part. The primers can be designed so that the PCR reaction goes outward, away from the center of the common part, such that the resultant PCR product includes the two barcodes at the center, flanked by the parts of the assembly, with the common part removed (except the portions complementary to the PCR primers). This smaller fragment can then be ligated to sequencing adaptors and NGS sequencing can be performed. These strategies should be ideal for sequence verification of cistron-sized assemblies. In other embodiments, the assemblies can be too large for the strategies described above, or the assembly pool can contain no common parts. Under such circumstances, sequencing can be performed, for example, using multiplex "jumping" libraries, primer walking amplification, or Single-Molecule Long Reads (SMRT) approaches (FIG. 17).

Exemplary NGS platforms suitable for use with the present disclosure include the MiSeq and HiSeq platforms (Illumina), the SOliD platform (Applied Biosystems), Roche 454 pyrosequencing, Ion Torren, Ion Proton (Life Technologies), PacBio RS, Oxford Nanopore, and other NGS platforms known in the art.

Aspects of the method further include hashing the nucleic acid parts, nucleic acid elements and/or higher-order nucleic acid constructs, for example as described below and in the Figures. Thus in certain embodiments, the method further includes attaching a DNA hash, that include a unique nucleic acid barcode, to each of the nucleic acid parts, nucleic acid elements and/or higher-order nucleic acid constructs at the 5' and/or 3' end of the nucleic acid parts, nucleic acid elements and/or higher-order nucleic acid constructs and assigning the individual DNA hashes to the individual nucleic acid sequences in the plurality of nucleic acid parts, nucleic acid elements and/or higher-order nucleic acid constructs, thereby creating a hash table, wherein the sequence of the individual unique nucleic acid barcode in the hash table represents the sequence of the nucleic acid parts, nucleic acid elements and/or higher-order nucleic acid constructs. In some embodiments, the DNA hash includes nucleic acid primer sites 5' and 3' of a unique molecular identifier. In certain embodiments, the method further includes amplifying the unique molecular identification sequence using primers that specifically hybridize to the nucleic acid primer sites. In some examples the primers further include a nucleic acid sequence that specifically hybridizes to the sequence of one of the nucleic acid parts, nucleic acid elements and/or higher-order nucleic acid constructs. In some embodiments, a concatemer of amplified unique molecular identification sequences is assembled, and optionally the sequence of the assembled concatemer is determined, thereby determining the sequence of the nucleic acid parts, nucleic acid elements and/or higher-order nucleic acid constructs and/or the order of assembly of the nucleic acid parts, nucleic acid elements and/or higher-order nucleic acid constructs.

B. Nucleic Acid Elements

Disclosed is a set of sequence-verified nucleic acid elements, or amplification products thereof, for the combinatorial construction of genetic elements including one or more nucleic acid elements assembled from: a set of nucleic acid sequences comprising different promoters; a set of nucleic acid sequences comprising a set of different ribosomal binding sites; a set of nucleic acid sequences encoding a polypeptide; and/or a set of nucleic acid sequences comprising a set of different transcription terminators, wherein sequence of the nucleic acid element is determined after assembly. The nucleic acid parts can include any sequence of DNA, ranging in size and scale from individual components of a cistron to clusters of cistrons. Parts can range in size from less than 50 bp to greater than 8 kilobases (kb). Exemplary nucleic acid parts may have a length of about 10 bp, 20 bp, 30 bp, 40 bp, 50 bp, 60 bp, 70 bp, 80 bp, 90 bp, 100 bp, 200 20 bp, 300 bp, 400 bp, 500 bp, 600 bp, 700 bp, 800 bp, 900 bp, 1 kb, 2 kb, 3 kb, 4 kb, 5 kb, 6 kb, 7 kb, 8 kb, 9 kb, or 10 kb, or a length in a range specified by any combination of the prior-listed lengths (for example, ranges between adjacent listed lengths). Additional nucleic acid parts that can be components of nucleic acid elements include one or more of any combination of the following: barcodes, restriction sites (for example, Type IIs restriction enzyme sites), scars/cohesive ends, promoters, spacers, ribosomal binding sites (RBS), and/or sequences encoding a polypeptide of interest (coding region or CDS), for example, an entire polypeptide of interest or a subset (for example, a domain). FIG. 11 depicts an exemplary cistron containing, in order from 5' to 3' end: a 5' barcode sequence, a BbsI recognition site, a scar sequence, a promoter/spacer, an RBS, a CDS, a terminator/spacer, a second scar sequence, a second BbsI recognition site, and a 3' barcode sequence. Such nucleic acid parts may be initially designed by, for example, mining a database such as NCBI to identify known parts for each desired category of nucleic acid parts, such as those listed above. In some embodiments, the nucleic acid parts further comprise one or more nucleic acid assembly sequences that order assembly. In some embodiments, the nucleic acid assembly sequence comprises one or more restriction sites and, prior to assembly, they are cleaved restriction site to produce sticky ends to facilitate assembly.

In some embodiments, the nucleic acid elements include at least three sequences selected from the set of a promoters, ribosomal binding sites, coding sequences, and transcription terminators. In some embodiments, the nucleic acid elements include at least four sequences selected from the set of promoters, ribosomal binding sites, coding sequences and transcription terminators. In some embodiments, two or more of the assembled nucleic acid parts in the nucleic acid element are not from the same set. In some embodiments, two or more of the assembled nucleic acid parts in the nucleic acid element are from the same set. In some embodiments, the nucleic acid element includes a functional cistron or a subunit thereof. In some embodiments, the nucleic acid element includes a nucleic acid encoding a protein. In some embodiment the nucleic acid elements or parts include a 3' and/or a 5' flanking nucleic acid sequence that orders assembly of higher-order nucleic acid constructs, facilities retrieval and/or identification of the nucleic acid element. In some embodiments, the sequence-verified nucleic acid elements further include a nucleic acid barcode to the 5' and/or 3' end of the nucleic acid element. In some embodiments, the 3' and/or 5' flanking sequences comprise one or more restriction sites and, prior to assembly, they are cleaved restriction site to produce sticky ends to facilitate assembly. In some embodiments, the one or more restriction sites comprises at least one Type IIs restriction site. In some embodiments, cleavage of the Type IIs restriction site results in cohesive end overhangs at the 5' and 3' ends of the nucleic acid sequences such that the sequences are assembled into a continuous DNA fragment with the designed order and orientation of its components. In some embodiments, the nucleic acid parts further comprise one or more nucleic acid barcodes. In some embodiments, the 3' and/or 5' flanking sequences comprise one or more nucleic acid barcodes.

In some embodiments, assembling includes ligation of the nucleic acid sequences. In some embodiments, one or more of the set of nucleic acid sequences comprising the set of different promoters; the set of nucleic acid sequences comprising the set of different ribosomal binding sites; the set of nucleic acid sequences encoding the set of different gene products, such as polypeptides, for example proteins or fragments thereof; and the set of nucleic acid sequences comprising the set of different transcription terminators are sequence variants, for example homologs, orthologs and/or sequence variants by virtue of the redundancy of the genetic code. By way of example, in the construction of a metabolic pathway (or other pathway) one may want to vary the sequences of the component, such as promoter sequences, coding sequences etc., to tune the and or tune the final product. In some embodiments, the protein includes an antibody or an antibody fragment. In some embodiments, the antibody or antibody fragment includes a humanized antibody or antibody fragment. In some embodiments, the antibody or antibody fragment is of isotype IgG, IgA, IgM, IgE, or IgD, and/or the fragment selected includes a Fab, Fab', F(ab')2, Fd, Fv, scFv, or SMIP. In some embodiments, at least one of the nucleic acid parts encodes an antibody variable domain. In some embodiments, at least one of the nucleic acid parts encodes an antibody constant domain. In some embodiments, at least one of the nucleic acid parts encodes a protein from a biological pathway. In some embodiments, the set of parts encodes multiple proteins from a biological pathway. In some embodiments, the set of parts encodes all of the proteins from a biological pathway. In some embodiments, the biological pathway includes a metabolic pathway. In some embodiments, the metabolic pathway includes a synthetic pathway or a catabolic pathway. In some embodiments, the biological pathway includes a genetic pathway. In some embodiments, the biological pathway includes a signal transduction pathway.

Also disclosed is a pool of higher-order nucleic acid constructs or amplification products thereof, including one or more nucleic acid elements assembled from the sequence-verified nucleic acid elements. In some embodiments, the higher-order nucleic acid constructs further include a nucleic acid barcode to the 5' and/or 3' end. Disclosed is set of plasmids including the pool of higher-order nucleic acid constructs and/or the set of sequence-verified nucleic acid elements.

C. Kits

In certain embodiments, the disclosure features a kit providing a pool of sequence-verified nucleic acid elements and/or the pool of higher-order nucleic acid constructs, and a plurality of primers for retrieving one or more sequence-verified nucleic acid elements and/or higher-order nucleic acid constructs. The pool can be assembled, for example, by the methods of the present disclosure. The kit can also include instructions describing which barcodes within the pool are associated with particular constructs. The kit can further include materials for retrieving certain constructs from the pool (for example, oligonucleotide primers for PCR retrieval, a polymerase, and a PCR buffer).

D. Applications

The present disclosure provides means for assembling complex genetic designs from component parts, and can thus be useful for genetic engineering and synthetic biology applications. Exemplary applications include construction and/or optimization of any of the following: gene clusters, proteins (for example, antibodies; see above), multi-gene networks, genetic circuits, biosynthetic pathways, signal transduction pathways, metabolic pathways, and gene expression regulatory pathways. For example, the genes required for biosynthesis of a useful compound (for example, a drug) can be assembled into a cluster and permutations of each category of parts systematically tested for their effect on attributes of interest (for example, efficiency of drug synthesis, drug potency, drug effectiveness, and level of gene expression in host cells).

The present disclosure also enables rapid and inexpensive construction and optimization of genetic designs, such as a biological pathway or genetic circuit. The components of such genetic designs (for example, parts as described herein) can be permuted iteratively at a massive scale in order to optimize a genetic design by permuting attributes such as gene expression, genetic architecture, operon organization, synthetic regulation, or transcript splicing. Additionally, a CDS can by permuted and optimized by testing varying CDS sequences to examine the effect of mutations or different synthetic CDS (for example, different polypeptides, codon usage, multiple nucleotide polymorphisms, single nucleotide polymorphisms, deletions, duplications, insertions, and frame shifts). The methods described herein further enable rapid and targeted combinatorial permuting of a genetic design to probe high-dimensional and vast genetic search spaces. Thus, the methods herein can be used to engineer and debug larger and more complex genetic designs than existing methods in the art, thus expanding the complexity of biological systems that can be written, engineered, and optimized.

Figure 2:
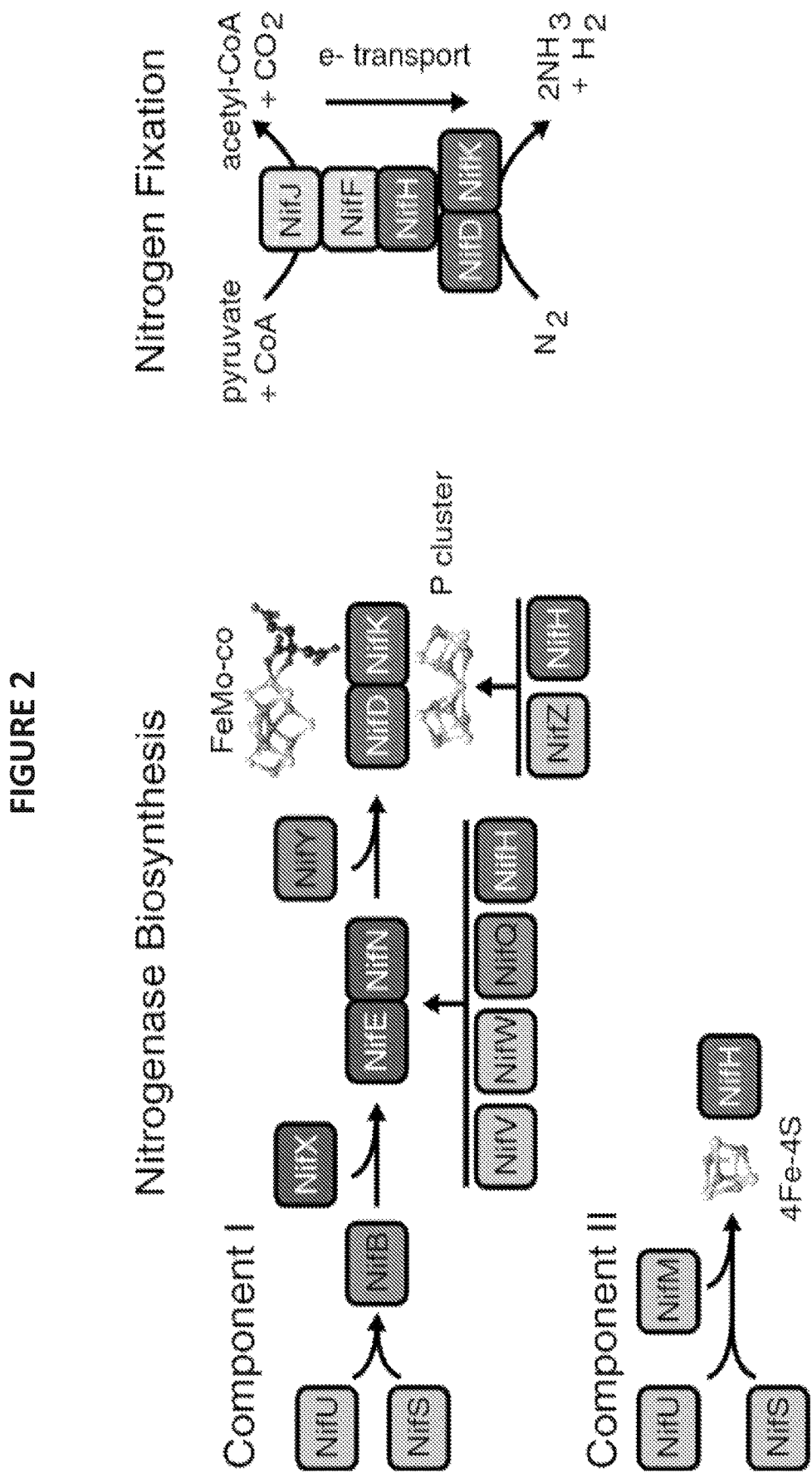
FIG. 2 is a diagram showing components of nitrogenase biosynthesis and nitrogen fixation pathways.
Figure 3:
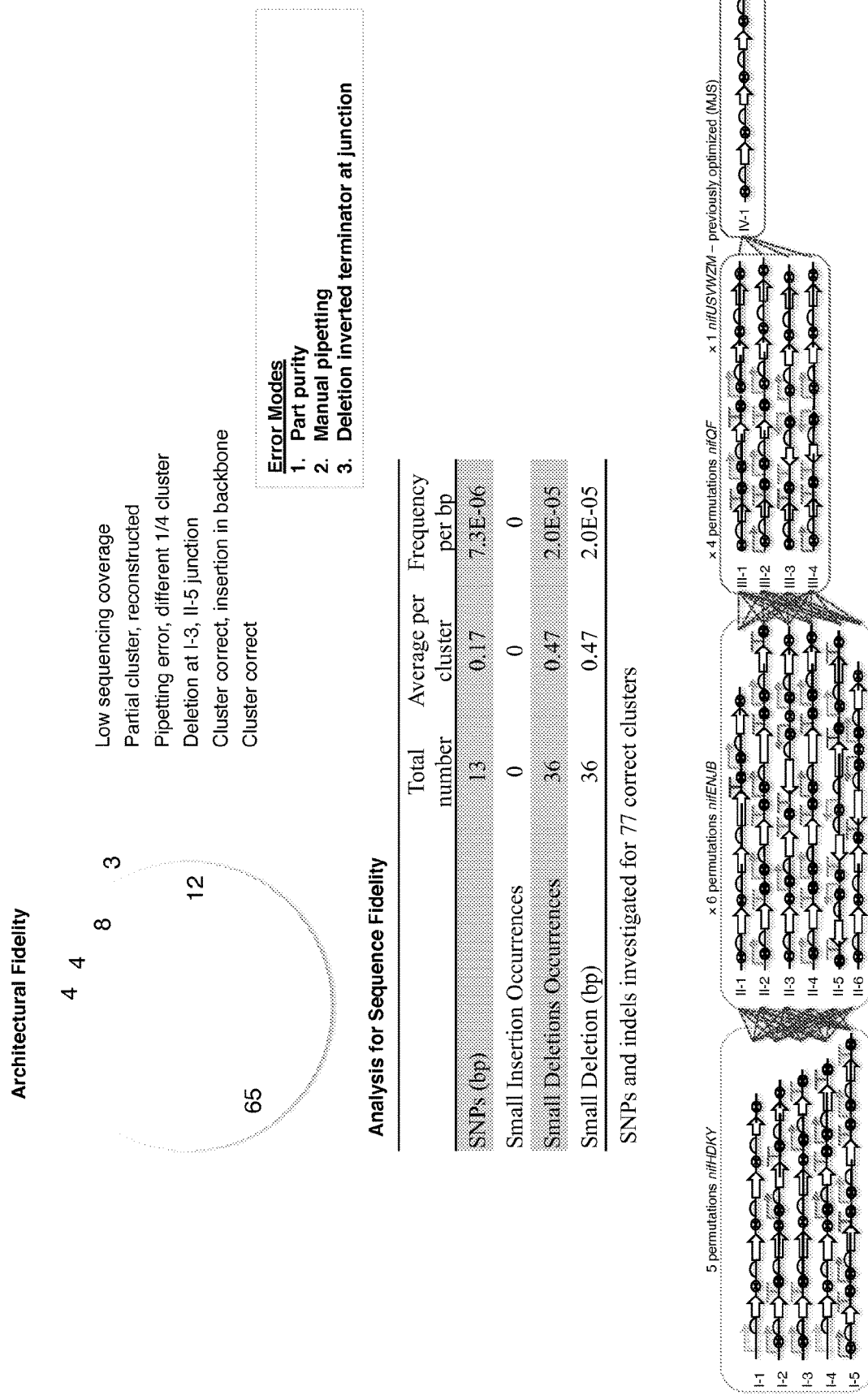
FIG. 3 is a set of diagrams showing the results of 96 whole cluster sequence analysis to identify error modes in existing assembly methodologies.

Existing methods for assembling genetic permutations produce a variety of error modes relating to, for example, part purity, low sequencing coverage, partial clusters, pipetting error, deletions, and insertions. To determine the prevalence of such error modes, the inventors have generated permutations of gene clusters including components of nitrogenase biosynthesis and nitrogen fixation pathways (FIG. 2). Golden Gate hierarchical cloning according to the MoClo system described by Weber et al. (PLoS ONE 6(2): e16765, 2011; incorporated herein by reference in its entirety) was used to generate a library of nif clusters featuring 5 permutations of nifHDKY, 6 permutations of nifENJB, 4 permutations of nifQF, and 1 permutation of nifUSVWZM (FIG. 3). We found that only 65% of assembled sequences showed fully correct clusters, with backbone insertions as the most prevalent error mode, followed by error due to manual pipetting. Further examination of a set of 77 correct clusters revealed an average of 0.17 single nucleotide polymorphisms (SNPs) and 0.47 small deletions within each cluster.

Figure 4:
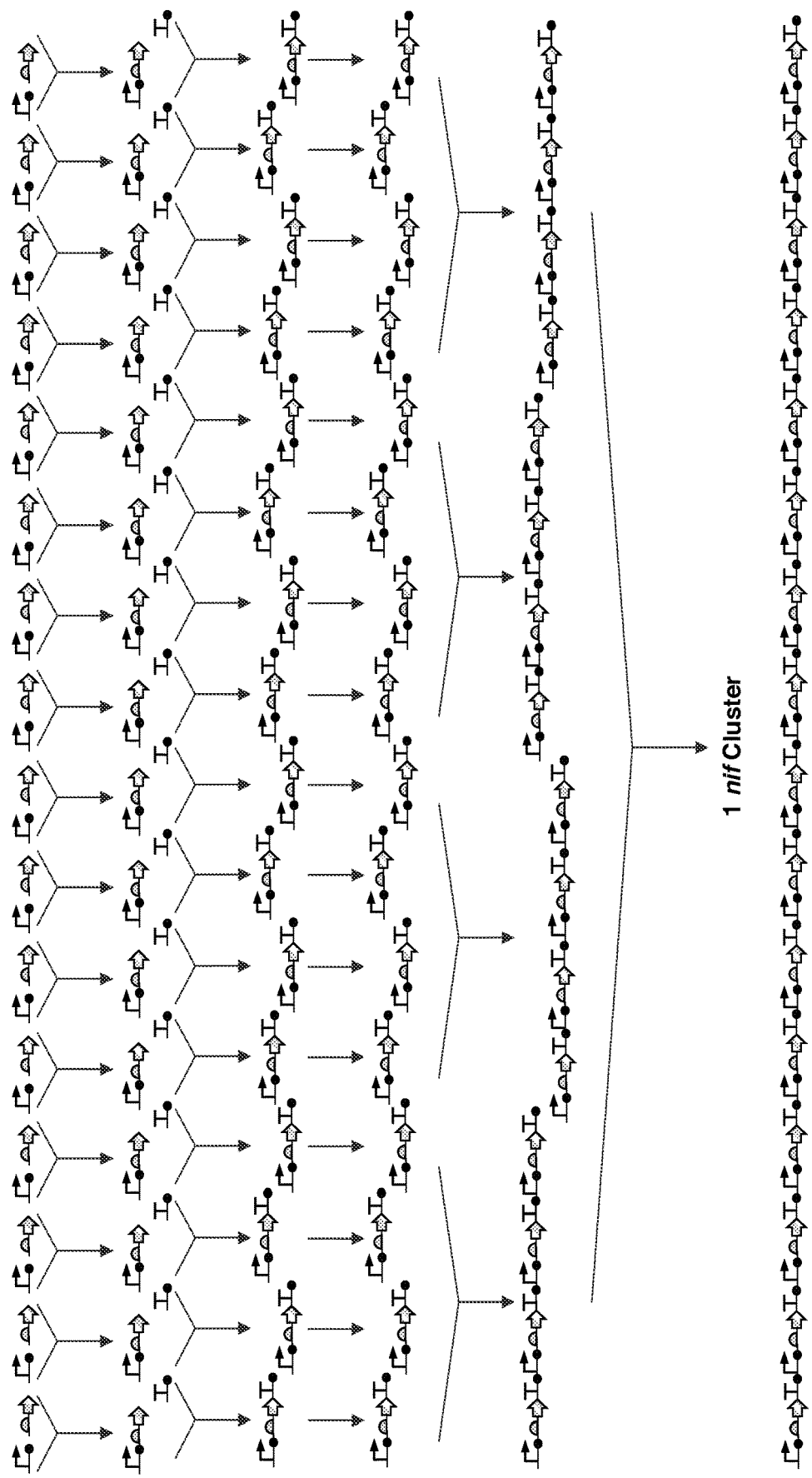
FIG. 4 is a diagram showing the assembly of a verified nif cluster using 53 iterations of assembly reactions, transformations, colony selection, purification, and normalization; and 64 Sanger sequencing reactions.

In addition to a high error rate, these existing methods for DNA assembly are notably costly and slow. As shown in FIG. 4, producing each unique nif cluster required 53 iterations of the following procedure: (1) assembly reaction, (2) bacterial transformation, (3) colony selection, (4) plasmid purification, and (5) concentration normalization. Each arrow represents a single iteration of the procedure. In addition, 64 Sanger sequencing reactions were required to obtain the complete sequence of each cluster. Thus, there is a need for high-throughput DNA assembly allowing for rapid and inexpensive production, sequence verification, testing, and retrieval of genetic permutations.

E. DNA Hashing

Aspects of the current disclosure relate to DNA hashing, either in the contact of the other embodiments, or as stand-alone technology. By way of example and with reference to the methods disclosed herein, the size and scale of multi-part designs that can be built in synthetic biology has been rapidly increasing, yet massively parallel testing of combinatorial designs has remained challenged by the ability to track the performance of individual genetic designs in high-throughput (pooled) screens or selections. Previous approaches used have been: individually constructing and assaying genetic designs (low through-put), combinatorial libraries without tracking all or full designs (sequence individual 'winners'), and combinatorial libraries limited to short regions of DNA variation with high-throughput NGS tracking (for example <5 parts as opposed to 100+ parts as disclosed herein). For large multi-part DNA designs, a key bottleneck to applying high-throughput screening or selections has been the need to sequence the entire (10-100,000 kb) design to determine the composition of parts.

To solve this problem, the inventors have developed a DNA hashing technology, similar to hashing in a computer environment, where small data sequences, typically transformed with a hashing function, are used to pinpoint or index larger data elements, such as in a database. With reference to the methods disclosed herein, as an analogy to the computer database if one considers the different nucleic acid parts as values in a database, a unique DNA hash, for example barcode can be assigned to the different nucleic acid parts, strings of genetic parts, or entire cistrons such that the individual nucleic acid part, string of parts, or cistron in a larger construct can be determined, both for order and presence, by determining the sequence of the DNA hashes, for example determining the sequence of a DNA hash concatemer. The sequence information, for example the sequences of the DNA hashes and/or nucleic acid sequence elements, can be stored in a hash table. Nested DNA hashing can also be used. For example an individual genetic part or construct of genetic parts can be uniquely barcoded within a cistron construct and the assembled cistron containing additional parts can be uniquely barcoded to represent all parts within the cistron.

Figure 47:
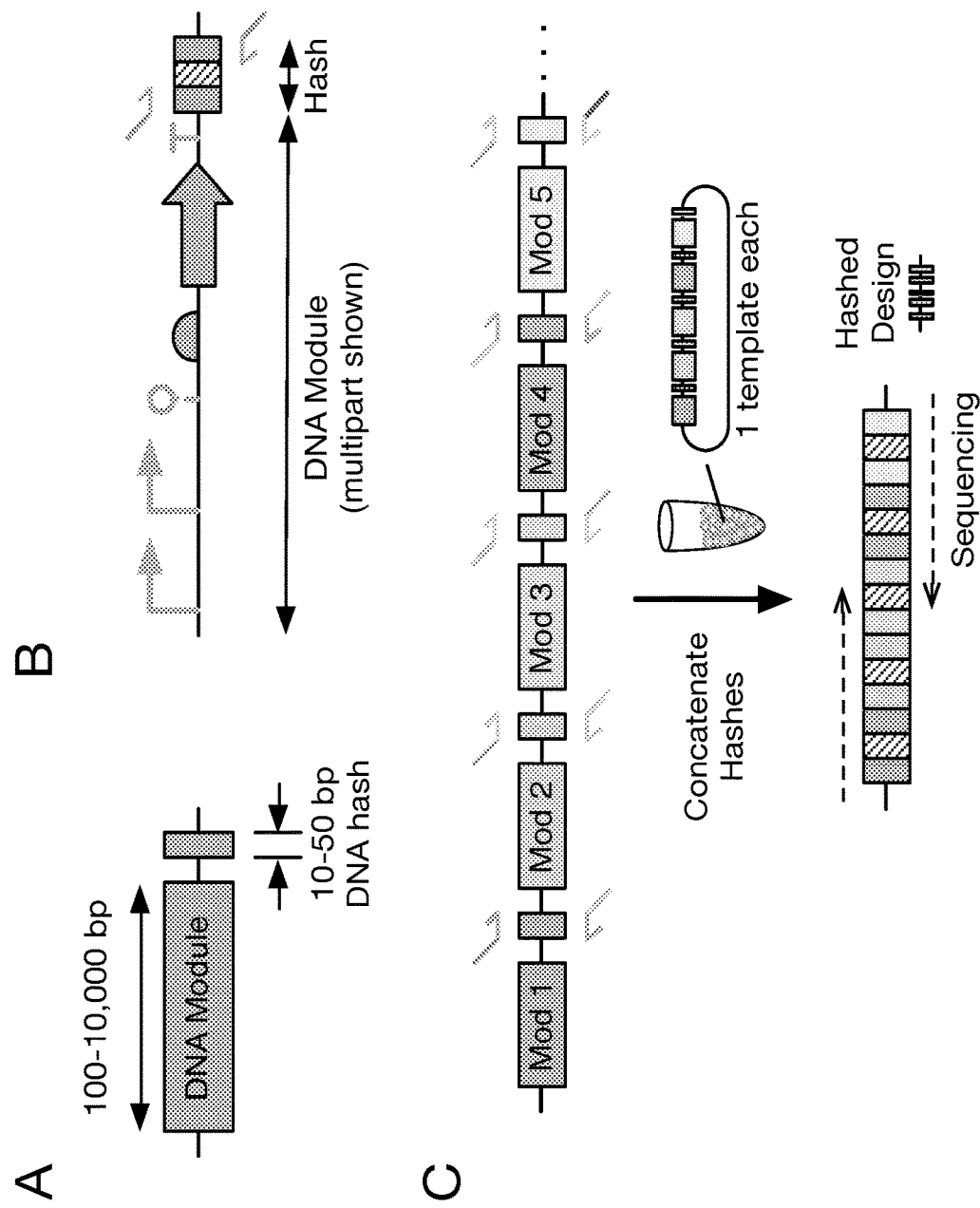
FIG. 47A-47C is a schematic showing a DNA hashing method for multi-module genetic constructs.
Figure 48:
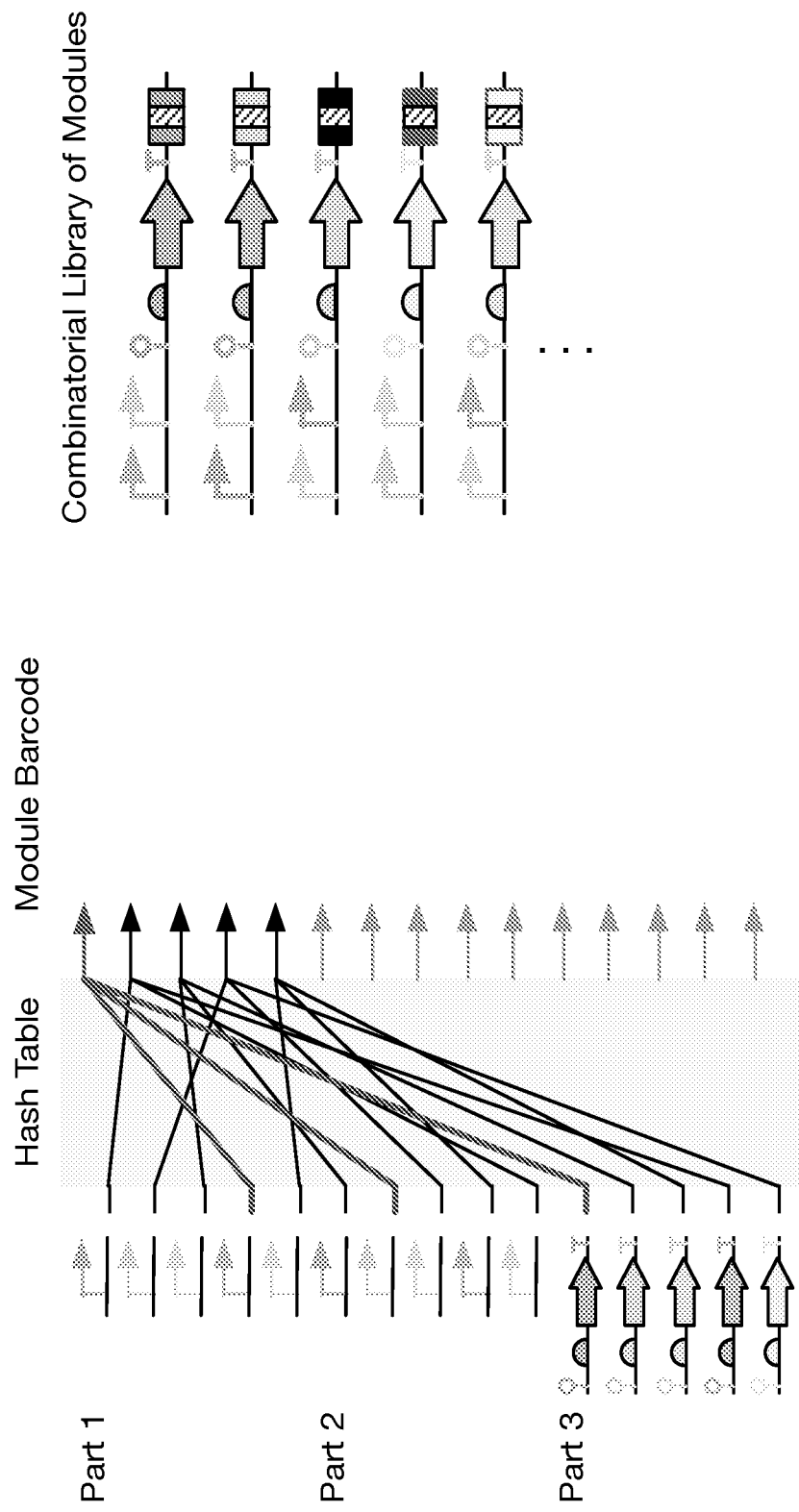
FIG. 48 is a schematic showing the generation of hash tables for synthetic DNA modules. Each hashed module can be a combination of parts, such as a combinatorial library of transcriptional units (as shown). Each unique module or combination of smaller DNA parts is assigned a unique 'hash' DNA barcode, which can be a specified sequence or random DNA sequence determined by sequencing a pool of modules. There can be 10,000's through millions of modules in a library.

With reference to FIG. 47 a unique identifying DNA sequence (e.g. hash that includes a unique DNA barcode) is attached to longer modules of DNA (see FIG. 47A) such that only the short barcode 'hash' needs to be sequenced to determine the presence a longer DNA fragment or string of DNA parts (see FIG. 47B). After assaying performance for approximately 100,000 to 1 million design variants (e.g., binning or fitness determination), these short 'hash' barcodes are then concatenated into a single DNA string, for example using emulsion PCR stitching (see FIG. 47C). In this way, the concatenated hashes of the DNA parts or cistrons have been compressed to potentially the length of a single paired-end read, which allows for increased assaying through-put and lower cost sequencing.

Disclosed is a method of nucleic acid hashing, for example of a plurality of nucleic acid sequence elements. The method includes attaching a DNA hash, that has a unique nucleic acid barcode to each of the plurality of nucleic acid sequence elements at the 5' and/or 3' end of the nucleic acid sequence; assigning the individual DNA hashes to the individual nucleic acid sequences in the plurality of nucleic acid sequence elements, thereby creating a hash table wherein the sequence of the individual unique nucleic acid barcode in the hash table represents the sequence of the nucleic acid sequence elements. In certain embodiments, the unique DNA hash is assigned randomly, and the unique DNA hash sequence, and/or the individual nucleic acid with which it is associated, and which the DNA hash sequence thereby denotes, is determined by sequencing. In certain embodiments the unique nucleic acid barcode includes flanking nucleic acid primer sites 5' and 3' of a unique molecular identifier, such as a unique 12 bp DNA sequence. In certain embodiments, the method further includes assembling two or more of the plurality of nucleic acid sequences. In certain embodiments, the method further includes amplifying the unique molecular identification sequence using primers that specifically hybridize to the nucleic acid primer sites. In certain embodiments, the primers further comprise a nucleic acid sequence that specifically hybridizes to the sequence of one of the nucleic acid sequence elements. In certain embodiments the method further includes assembling a concatemer of amplified unique molecular identification sequences. In certain embodiments, the method further includes determining the sequence of the assembled concatemer, thereby determining the sequence of the nucleic acid sequence elements and/or the order of assembly of the nucleic acid sequence elements.

In computing, a hash table (hash map) is a data structure used to implement an associative array, a structure that can map keys to values. A hash table uses a hash function to compute an index into an array of buckets or slots, from which the correct value can be found.

F. Other Embodiments

Embodiments of the disclosed methods may be implemented in a computer program that embodies the functions described and illustrated herein, wherein the computer program is implemented in a computer system that comprises instructions stored in a machine-readable medium and a processor that executes the instructions. However, it should be apparent that there could be many different ways of implementing embodiments in computer programming, and the embodiments should not be construed as limited to any one set of computer program instructions. Further, a skilled programmer would be able to write such a computer program to implement an embodiment of the disclosed embodiments based on the figures and associated description in the application text. Therefore, disclosure of a particular set of program code instructions is not considered necessary for an adequate understanding of how to make and use embodiments. Further, those skilled in the art will appreciate that one or more aspects of embodiments described herein may be performed by hardware, software, or a combination thereof, as may be embodied in one or more computing systems. Moreover, any reference to an act being performed by a computer should not be construed as being performed by a single computer as more than one computer may perform the act. Further disclosed are one or more electronic files including sequence information for to pool of sequence-verified nucleic acid elements and/or a pool of higher-order nucleic acid constructs; and a plurality of primers for retrieving one or more sequence-verified nucleic acid elements and/or higher-order nucleic acid constructs.

The example embodiments described herein can be used with computer hardware and software that perform the methods and processing functions described previously. The systems, methods, and procedures described herein can be embodied in a programmable computer, computer-executable software, or digital circuitry. The software can be stored on computer-readable media. For example, computer-readable media can include a floppy disk, RAM, ROM, hard disk, removable media, flash memory, memory stick, optical media, magneto-optical media, CD-ROM, etc. Digital circuitry can include integrated circuits, gate arrays, building block logic, field programmable gate arrays (FPGA), etc.

The example systems, methods, and acts described in the embodiments presented previously are illustrative, and, in alternative embodiments, certain acts can be performed in a different order, in parallel with one another, omitted entirely, and/or combined between different example embodiments, and/or certain additional acts can be performed, without departing from the scope and spirit of various embodiments. Accordingly, such alternative embodiments are included in the examples described herein.

Figure 49:
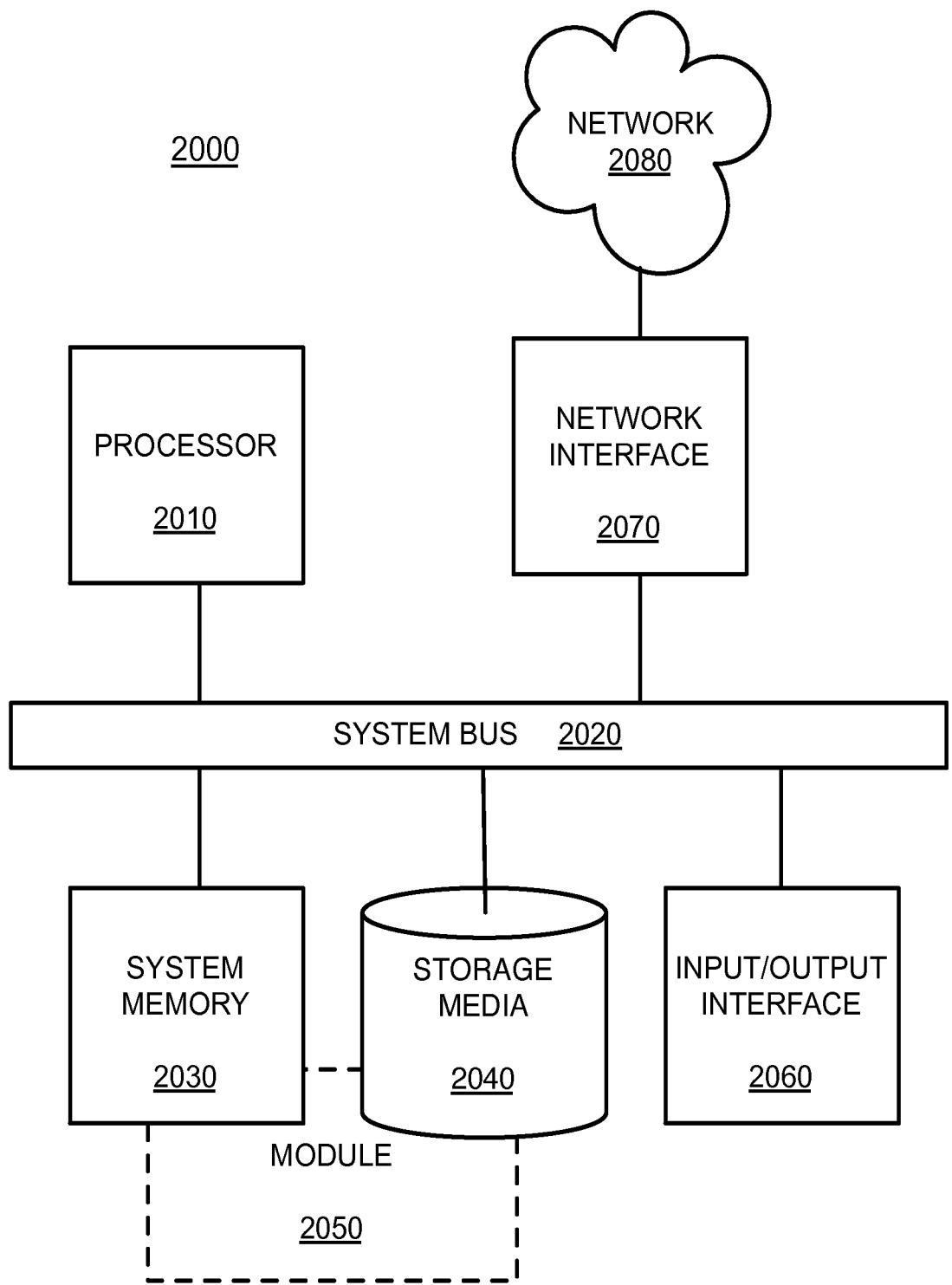
FIG. 49 is a block diagram depicting a computing machine and a module, in accordance with certain example embodiments.

FIG. 49 depicts a computing machine 2000 and a module 2050 in accordance with certain example embodiments. The computing machine 2000 may correspond to any of the various computers, servers, mobile devices, embedded systems, or computing systems presented herein. The module 2050 may comprise one or more hardware or software elements configured to facilitate the computing machine 2000 in performing the various methods and processing functions presented herein. The computing machine 2000 may include various internal or attached components such as a processor 2010, system bus 2020, system memory 2030, storage media 2040, input/output interface 2060, and a network interface 2070 for communicating with a network 2080.

The computing machine 2000 may be implemented as a conventional computer system, an embedded controller, a laptop, a server, a mobile device, a smartphone, a set-top box, a kiosk, a vehicular information system, one more processors associated with a television, a customized machine, any other hardware platform, or any combination or multiplicity thereof. The computing machine 2000 may be a distributed system configured to function using multiple computing machines interconnected via a data network or bus system.

The processor 2010 may be configured to execute code or instructions to perform the operations and functionality described herein, manage request flow and address mappings, and to perform calculations and generate commands. The processor 2010 may be configured to monitor and control the operation of the components in the computing machine 2000. The processor 2010 may be a general purpose processor, a processor core, a multiprocessor, a reconfigurable processor, a microcontroller, a digital signal processor ("DSP"), an application specific integrated circuit ("ASIC"), a graphics processing unit ("GPU"), a field programmable gate array ("FPGA"), a programmable logic device ("PLD"), a controller, a state machine, gated logic, discrete hardware components, any other processing unit, or any combination or multiplicity thereof. The processor 2010 may be a single processing unit, multiple processing units, a single processing core, multiple processing cores, special purpose processing cores, co-processors, or any combination thereof. According to certain example embodiments, the processor 2010 along with other components of the computing machine 2000 may be a virtualized computing machine executing within one or more other computing machines.

The system memory 2030 may include non-volatile memories such as read-only memory ("ROM"), programmable read-only memory ("PROM"), erasable programmable read-only memory ("EPROM"), flash memory, or any other device capable of storing program instructions or data with or without applied power. The system memory 2030 may also include volatile memories such as random access memory ("RAM"), static random access memory ("SRAM"), dynamic random access memory ("DRAM"), and synchronous dynamic random access memory ("SDRAM"). Other types of RAM also may be used to implement the system memory 2030. The system memory 2030 may be implemented using a single memory module or multiple memory modules. While the system memory 2030 is depicted as being part of the computing machine 2000, one skilled in the art will recognize that the system memory 2030 may be separate from the computing machine 2000 without departing from the scope of the subject technology. It should also be appreciated that the system memory 2030 may include, or operate in conjunction with, a non-volatile storage device such as the storage media 2040.

The storage media 2040 may include a hard disk, a floppy disk, a compact disc read only memory ("CD-ROM"), a digital versatile disc ("DVD"), a Blu-ray disc, a magnetic tape, a flash memory, any other non-volatile memory device, a solid state drive ("SSD"), any magnetic storage device, any optical storage device, any electrical storage device, any semiconductor storage device, any physical-based storage device, any other data storage device, or any combination or multiplicity thereof. The storage media 2040 may store one or more operating systems, application programs and program modules such as module 2050, data, or any other information. The storage media 2040 may be part of, or connected to, the computing machine 2000. The storage media 2040 may also be part of one or more other computing machines that are in communication with the computing machine 2000 such as servers, database servers, cloud storage, network attached storage, and so forth.

The module 2050 may comprise one or more hardware or software elements configured to facilitate the computing machine 2000 with performing the various methods and processing functions presented herein. The module 2050 may include one or more sequences of instructions stored as software or firmware in association with the system memory 2030, the storage media 2040, or both. The storage media 2040 may therefore represent examples of machine or computer readable media on which instructions or code may be stored for execution by the processor 2010. Machine or computer readable media may generally refer to any medium or media used to provide instructions to the processor 2010. Such machine or computer readable media associated with the module 2050 may comprise a computer software product. It should be appreciated that a computer software product comprising the module 2050 may also be associated with one or more processes or methods for delivering the module 2050 to the computing machine 2000 via the network 2080, any signal-bearing medium, or any other communication or delivery technology. The module 2050 may also comprise hardware circuits or information for configuring hardware circuits such as microcode or configuration information for an FPGA or other PLD.

The input/output ("I/O") interface 2060 may be configured to couple to one or more external devices, to receive data from the one or more external devices, and to send data to the one or more external devices. Such external devices along with the various internal devices may also be known as peripheral devices. The I/O interface 2060 may include both electrical and physical connections for operably coupling the various peripheral devices to the computing machine 2000 or the processor 2010. The I/O interface 2060 may be configured to communicate data, addresses, and control signals between the peripheral devices, the computing machine 2000, or the processor 2010. The I/O interface 2060 may be configured to implement any standard interface, such as small computer system interface ("SCSI"), serial-attached SCSI ("SAS"), fiber channel, peripheral component interconnect ("PCI"), PCI express ("PCIe"), serial bus, parallel bus, advanced technology attached ("ATA"), serial ATA ("SATA"), universal serial bus ("USB"), Thunderbolt, FireWire, various video buses, and the like. The I/O interface 2060 may be configured to implement only one interface or bus technology. Alternatively, the I/O interface 2060 may be configured to implement multiple interfaces or bus technologies. The I/O interface 2060 may be configured as part of, all of, or to operate in conjunction with, the system bus 2020. The I/O interface 2060 may include one or more buffers for buffering transmissions between one or more external devices, internal devices, the computing machine 2000, or the processor 2010.

The I/O interface 2060 may couple the computing machine 2000 to various input devices including mice, touch-screens, scanners, electronic digitizers, sensors, receivers, touchpads, trackballs, cameras, microphones, keyboards, any other pointing devices, or any combinations thereof. The I/O interface 2060 may couple the computing machine 2000 to various output devices including video displays, speakers, printers, projectors, tactile feedback devices, automation control, robotic components, actuators, motors, fans, solenoids, valves, pumps, transmitters, signal emitters, lights, and so forth.

The computing machine 2000 may operate in a networked environment using logical connections through the network interface 2070 to one or more other systems or computing machines across the network 2080. The network 2080 may include wide area networks (WAN), local area networks (LAN), intranets, the Internet, wireless access networks, wired networks, mobile networks, telephone networks, optical networks, or combinations thereof. The network 2080 may be packet switched, circuit switched, of any topology, and may use any communication protocol. Communication links within the network 2080 may involve various digital or an analog communication media such as fiber optic cables, free-space optics, waveguides, electrical conductors, wireless links, antennas, radio-frequency communications, and so forth.

The processor 2010 may be connected to the other elements of the computing machine 2000 or the various peripherals discussed herein through the system bus 2020. It should be appreciated that the system bus 2020 may be within the processor 2010, outside the processor 2010, or both. According to some embodiments, any of the processor 2010, the other elements of the computing machine 2000, or the various peripherals discussed herein may be integrated into a single device such as a system on chip ("SOC"), system on package ("SOP"), or ASIC device.

Although specific embodiments have been described above in detail, the description is merely for purposes of illustration. It should be appreciated, therefore, that many aspects described above are not intended as required or essential elements unless explicitly stated otherwise. Modifications of, and equivalent components or acts corresponding to, the disclosed aspects of the example embodiments, in addition to those described above, can be made by a person of ordinary skill in the art, having the benefit of the present disclosure, without departing from the spirit and scope of embodiments defined in the following claims, the scope of which is to be accorded the broadest interpretation so as to encompass such modifications and equivalent structures.

EXAMPLES

The following examples are provided by way of illustration only and not by way of limitation. Those of skill in the art will readily recognize a variety of non-critical parameters that could be changed or modified to yield essentially the same or similar results.

Example 1

Multiplex Scarless Cistron Assembly and Sequencing Followed by Tag-Directed Retrieval High-throughput DNA assembly and genetic design strategies were used to optimize a pathway of 16 genes. This 16-gene nitrogen fixation (nif gene cluster is entirely modular and synthetic ("refactored") with ~100 parts. The synthetic nif pathway encodes 16 essential genes that have tightly coordinated action to convert atmospheric nitrogen into ammonia, a critical process for global agriculture productivity. Using our novel assembly strategy, we constructed and sequenced a library of >55,000 unique nif transcriptional units (TUs). This is a 100 fold to 1,000-fold improvement in library size over previous studies. Each TU is composed of characterized genetic parts (5-7 each), including one refactored nif gene. These nif TU modules can be directly assembled into whole 16-gene, 100-part permuted cluster designs (~1045 unique cluster designs possible from this library). Additionally, approximately 7.5 million nif cistrons were sequenced to characterize DNA assembly error modes and quantify their frequencies. Next, from the library of nif modules systematically permuted refactored clusters were built and tested to investigate optimizing nitrogen fixation activity by tuning expression within the factored cluster using characterized biological parts. Combinatorial design and statistical design of experiments were applied to constrain the part substitutions integrated into the cluster designs fabricated and tested in each round. Since the total number of possible combinations was in the 1040 range, random sampling of the pool was unlikely to produce an optimal design. By determining which parameters have the greatest effect on system performance, we could thus traverse the genetic design space more efficiently. Together, these methods enable model-guided redesign and optimization of genetic system performance with minimized DNA assembly required (~10-fold reduction in cloning).

Figure 5:
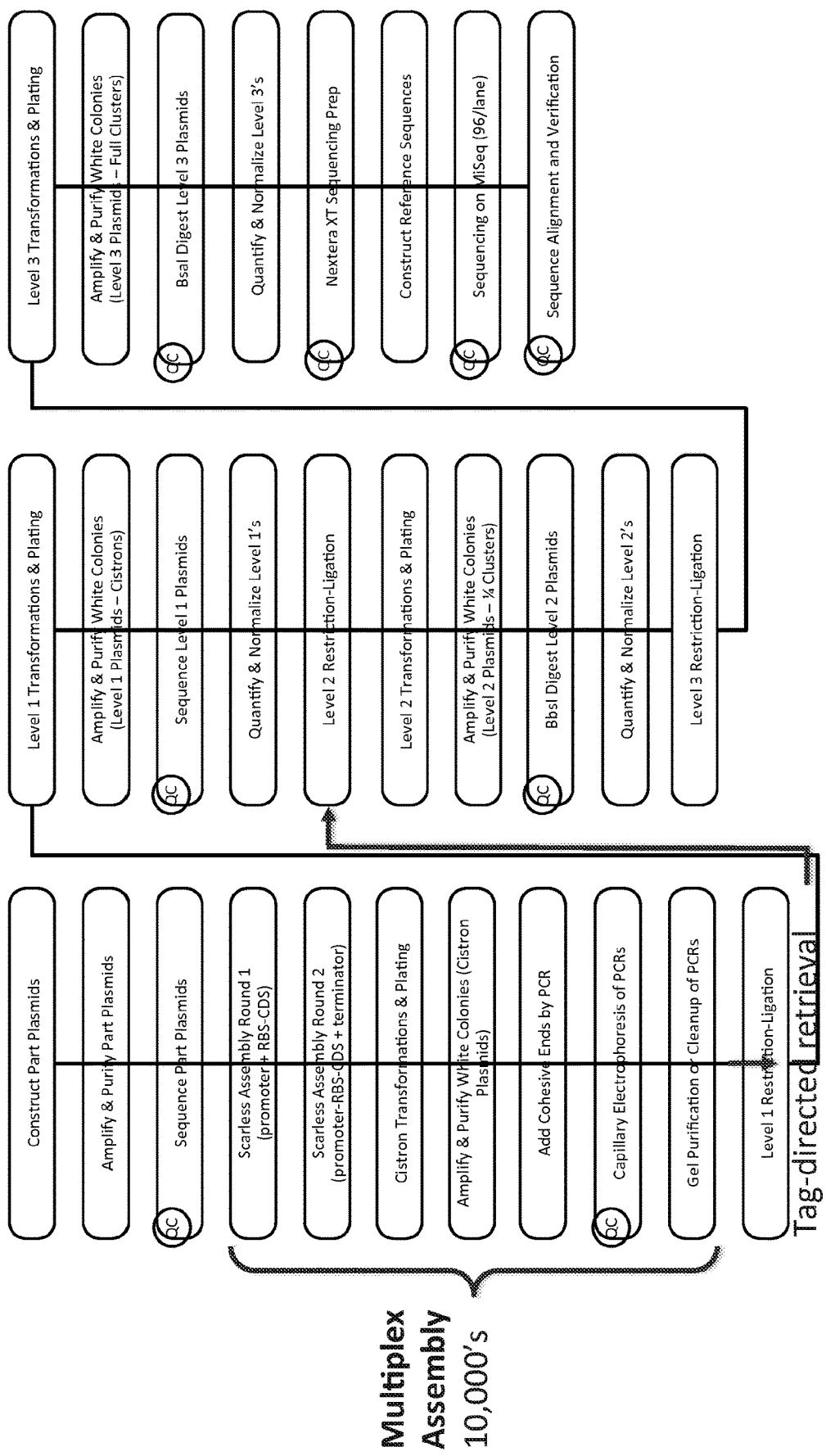
FIG. 5 is a flowchart illustrating a method of multiplex scarless DNA assembly and sequencing followed by tag-directed retrieval.
Figure 6:
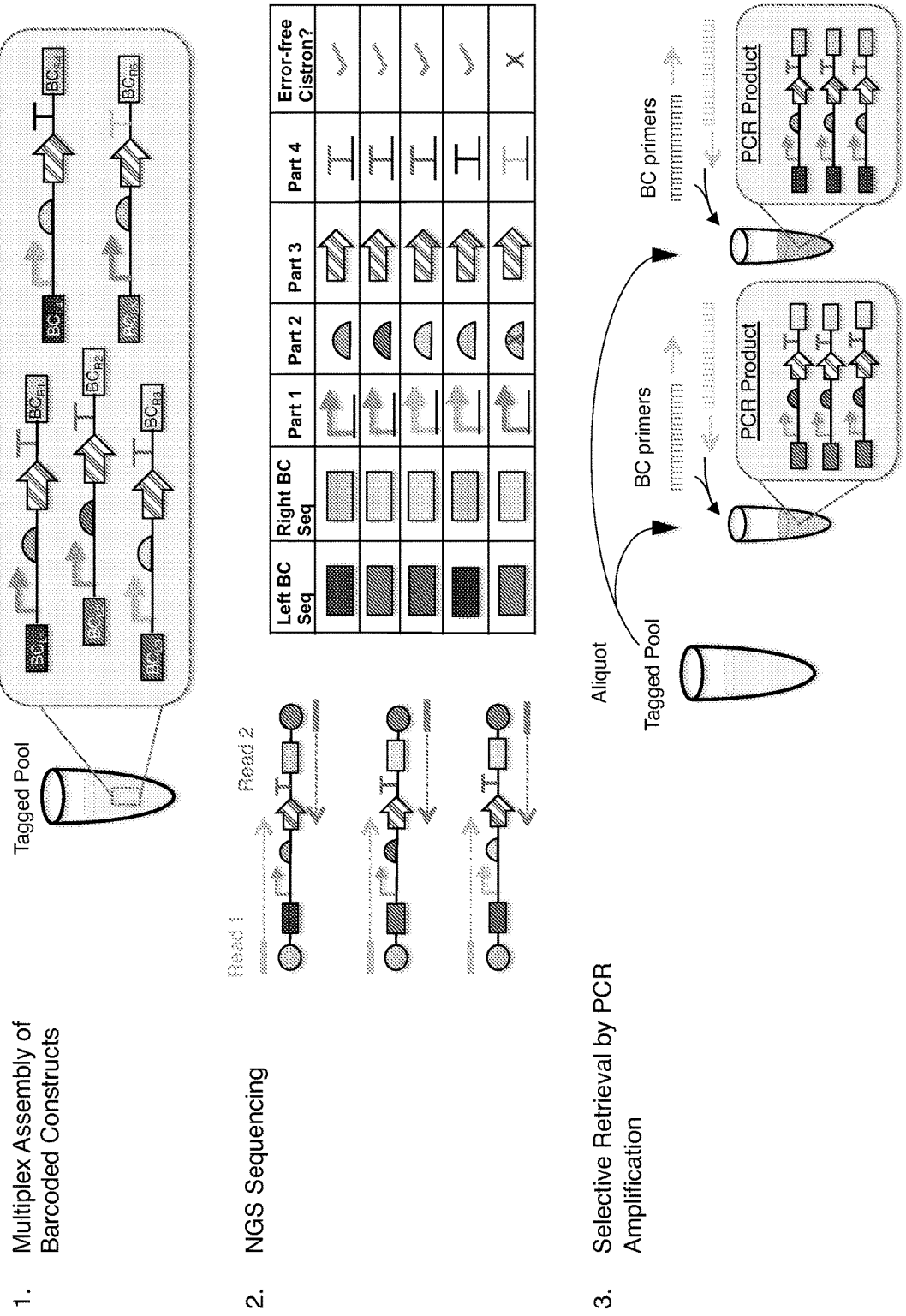
FIG. 6 is a diagram showing the steps of a method for barcoded multiplex assembly and tag-directed retrieval, involving (1) multiplex assembly of barcode-tagged constructs, (2) next-generation sequencing (NGS), and (3) selective retrieval of desired constructs by PCR amplification.
Figure 7:
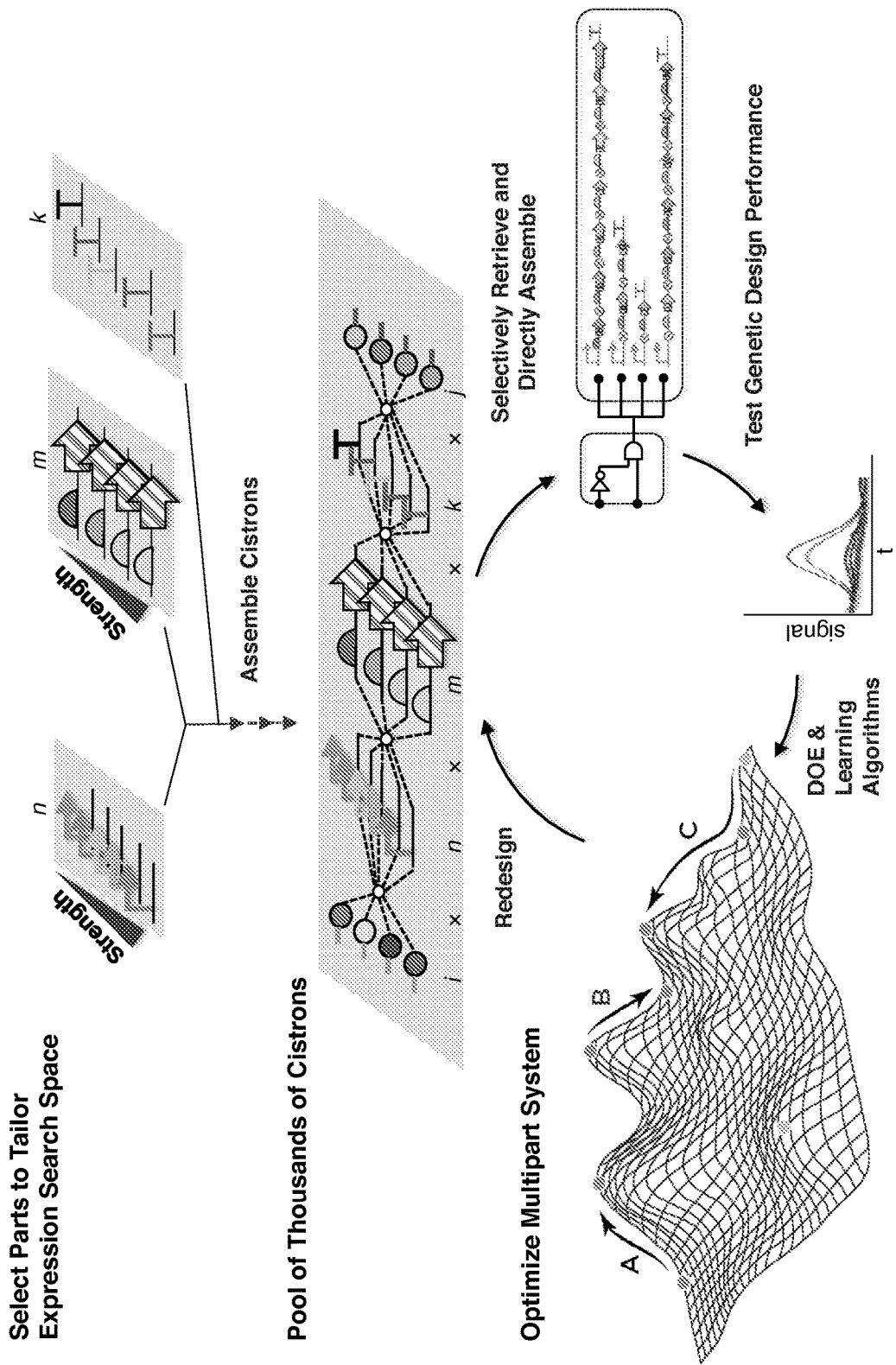
FIG. 7 is a flowchart illustrating rapid iterative permuting of massively multipart systems using the method of the present disclosure.

FIG. 5 illustrates the workflow used for one embodiment of the present disclosure, in which a pool of barcode-tagged constructs was assembled in multiplex. As shown in FIG. 6, each construct included a complete nif cistron, including four parts that could be added in order: a promoter, RBS, CDS, and terminator. In the present experiment, all cistrons featured the same nif CDS, which was included in a part featuring the varying RBS (FIG. 7). A unique pair of DNA barcodes flanked each cistron constructed, and next-generation sequencing was used to determine the sequence of each cistron and its associated barcodes. Cistrons were then assembled into clusters and experimentally tested. Desired cistrons and/or clusters were then retrieved by designing barcode-specific primers and performing polymerase chain reaction (PCR). After each round of assembly and testing, design of experiments methodology and learning algorithms were used to traverse the design space for optimal redesign of the next round of cistrons and/or clusters.

Figure 8:
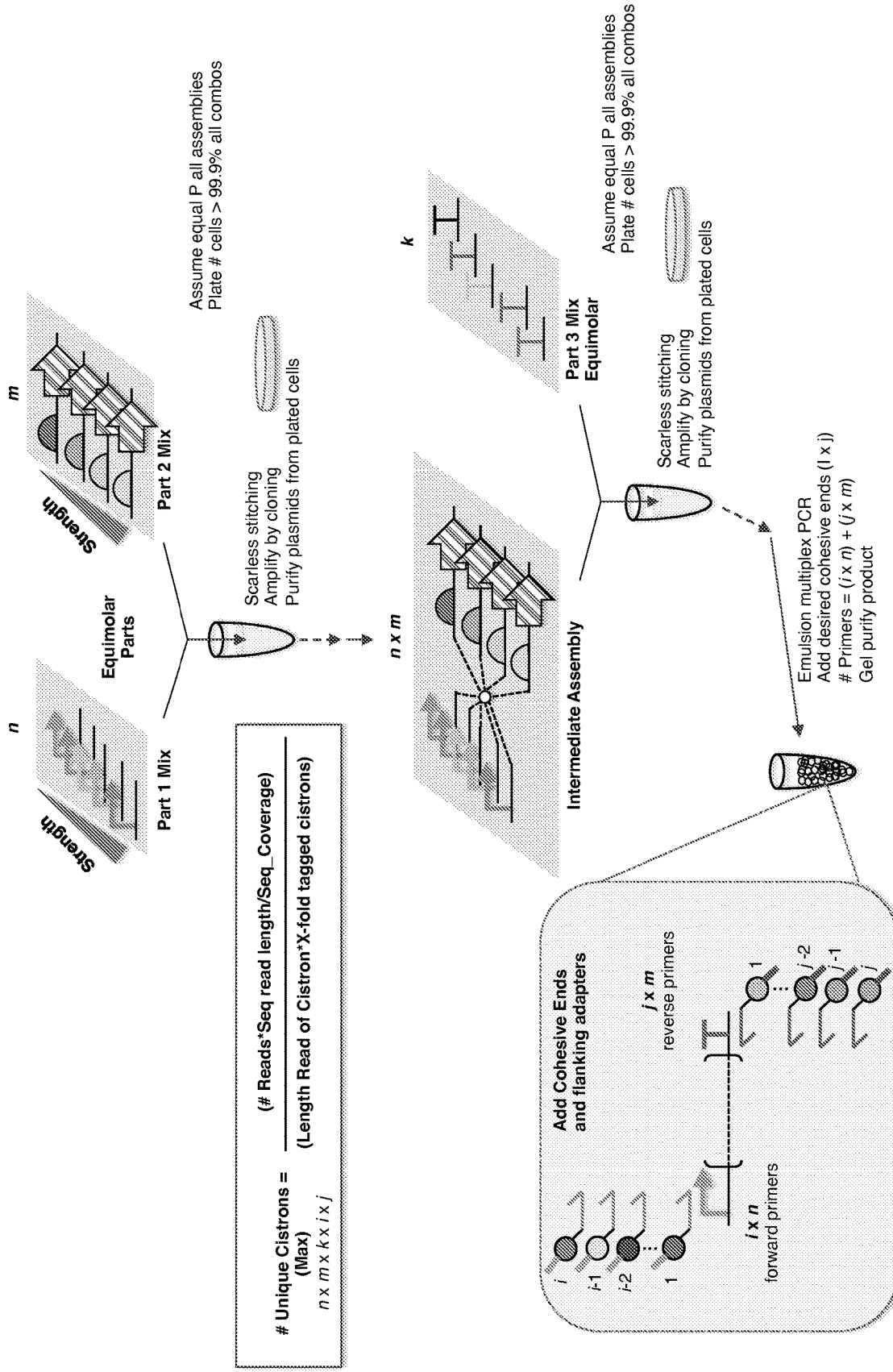
FIG. 8 is a flowchart illustrating the assembly of cistrons from mixtures of parts (for example, promoters, ribosomal binding sites/coding regions, and terminators). Here, multiplex scarless stitching is used, but other assembly methods are also compatible with this approach.

By selecting which parts to include in the assembly reactions, we could restrict the expression search space from the outset (FIG. 7). The promoter and RBS/CDS parts were assembled first, followed by addition of terminators, thus producing a pool of thousands of cistrons, which could be tested for genetic design performance. The assembly procedure is illustrated in FIG. 8. In brief, equimolar amounts of a "Part 1 Mix" containing promoters and a "Part 2 Mix" containing the variable RBS and constant CDS parts were attached by scarless stitching into intermediate assembly plasmids, which were then amplified by cloning and purified from plated bacterial cells. Scarless stitching was performed by Golden Gate cloning (Engler et al., PLoS ONE 3(11): e3647, 2008). The intermediate assemblies were then mixed with an equimolar amount of a "Part 3 Mix" containing terminator parts to assemble complete cistrons, again by Golden Gate cloning-based scarless stitching. After additional amplification and purification steps, cohesive ends and flanking adapters were added to each cistron to produce a cistron pool. Assuming equal probability of all parts and assemblies, we would expect that approximately ten times the number of unique combinations would be required for a 99.99% probability of sampling all possible permutations.

Figure 9:
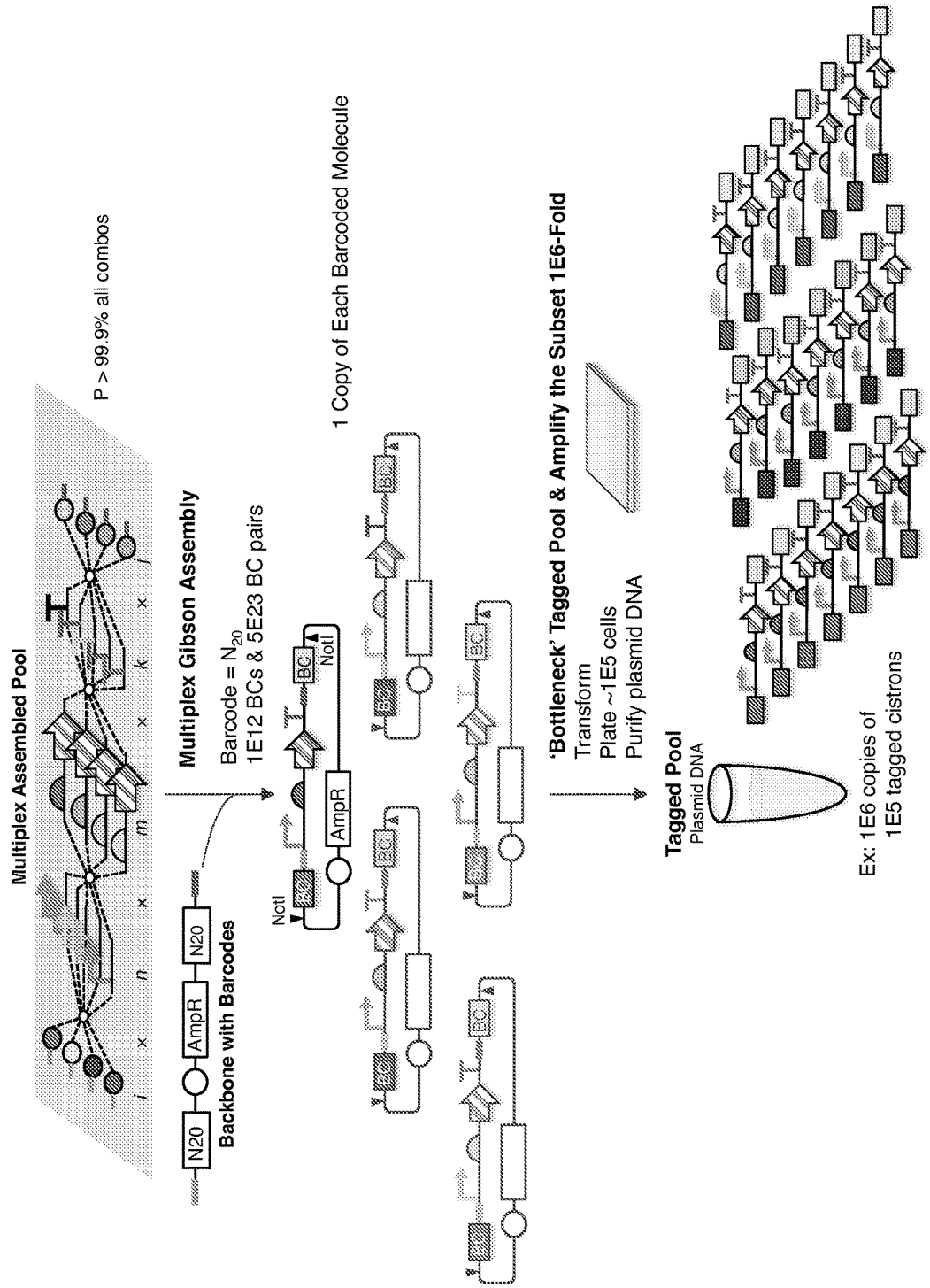
FIG. 9 is a flowchart illustrating the tagging of a multiplex assembled pool with barcodes and the amplification of the resultant tagged pool.

Once the pool was assembled, each cistron was uniquely tagged with a pair of barcodes (FIG. 9). Each cistron was inserted into a backbone containing an ampicillin resistance cassette and N20 barcodes (including 1E12 and 5E23 barcode pairs) by multiplex Gibson assembly, thus producing circularized plasmid constructs each containing a single cistron flanked by a unique pair of barcodes and NotI restriction sites. Bacterial cells were transformed with the tagged plasmid pool, plated, and grown according to routine microbial culture techniques, thus clonally amplifying individual plasmid constructs.

By plating a certain number of cells per transformation, this randomly bottlenecked the tagged pool, limiting the diversity of molecules to sequence. Amplified constructs were then recovered by plasmid isolation techniques routine in the art.

Figure 10:
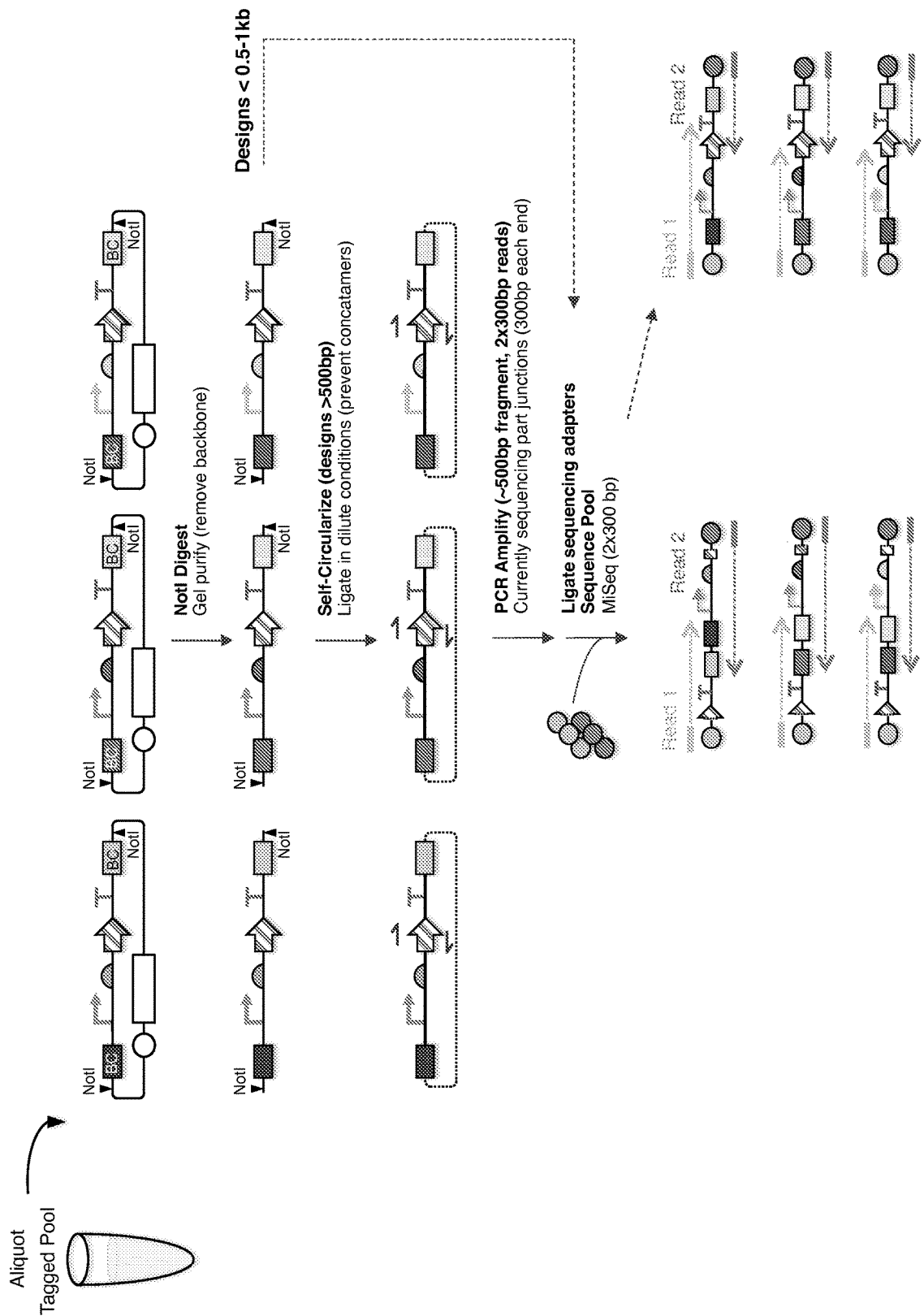
FIG. 10 is a flowchart illustrating the preparation of a tagged pool for sequencing by NGS.

As shown in FIG. 10, plasmid DNA containing multiple copies of each tagged cistron was then isolated and digested with NotI. Designs smaller than 500-1000 bp could progress immediately to sequencing adaptor ligation. For designs greater in size than about 500 bp, NotI-digested cistrons were self-circularized using standard ligation protocols performed at dilute concentrations, and then PCR amplified using primers directed at the ends of the common CDS sequence to produce ~500 bp PCR products that include, in order: the terminator, 3' barcode, 5' barcode, promoter, and RBS. Sequencing adaptors were subsequently ligated to both ends of each fragment. The pool was then sequenced using the MiSeq next-generation sequencing platform (Illumina), producing two reads per fragment or cistron, each read starting from one end of the polynucleotide and progressing inward. For short designs for which self-circularization and PCR amplification were skipped, the resultant contigs include the entirety of the cistron assembly. For longer designs, the contigs reveal the sequence of the 500 bp PCR product. In other case, the two barcode sequences and the sequences of all variable parts (for example, all parts other than the CDS) can be determined, thus allowing for comparison of a particular assembly's performance with its unique structure.

The structure of an exemplary nif cistron is shown in FIG. 11. From 5' to 3' end, each cistron included: a 5' barcode sequence, a BbsI recognition site, a 4-bp scar (selected from 10 possible scars), a promoter/spacer (selected from 5 possible promoter/spacer combinations), an RBS (selected from two possible RBSs), a nif CDS (selected from 16 possible refactored nif CDSs), a terminator/spacer (selected from 5 possible terminator/spacer combinations), a second 4-bp scar (selected from the same set of 10 possible scars as the first scar), a second BbsI recognition site, and a 3' barcode sequence. Using the set of parts described here, 80,000 unique nif cistrons can be produced 5,000 cistrons per nif CDS. Each 4-bp scar is located within the overhang region of the adjacent BbsI recognition site to form a complete BbsI restriction site. Thus, BbsI digestion produces overhangs on each end of the cistron that can be used for ordered assembly with other cistrons based on scar sequence complementarity to generate clusters of cistrons.

Figure 12:
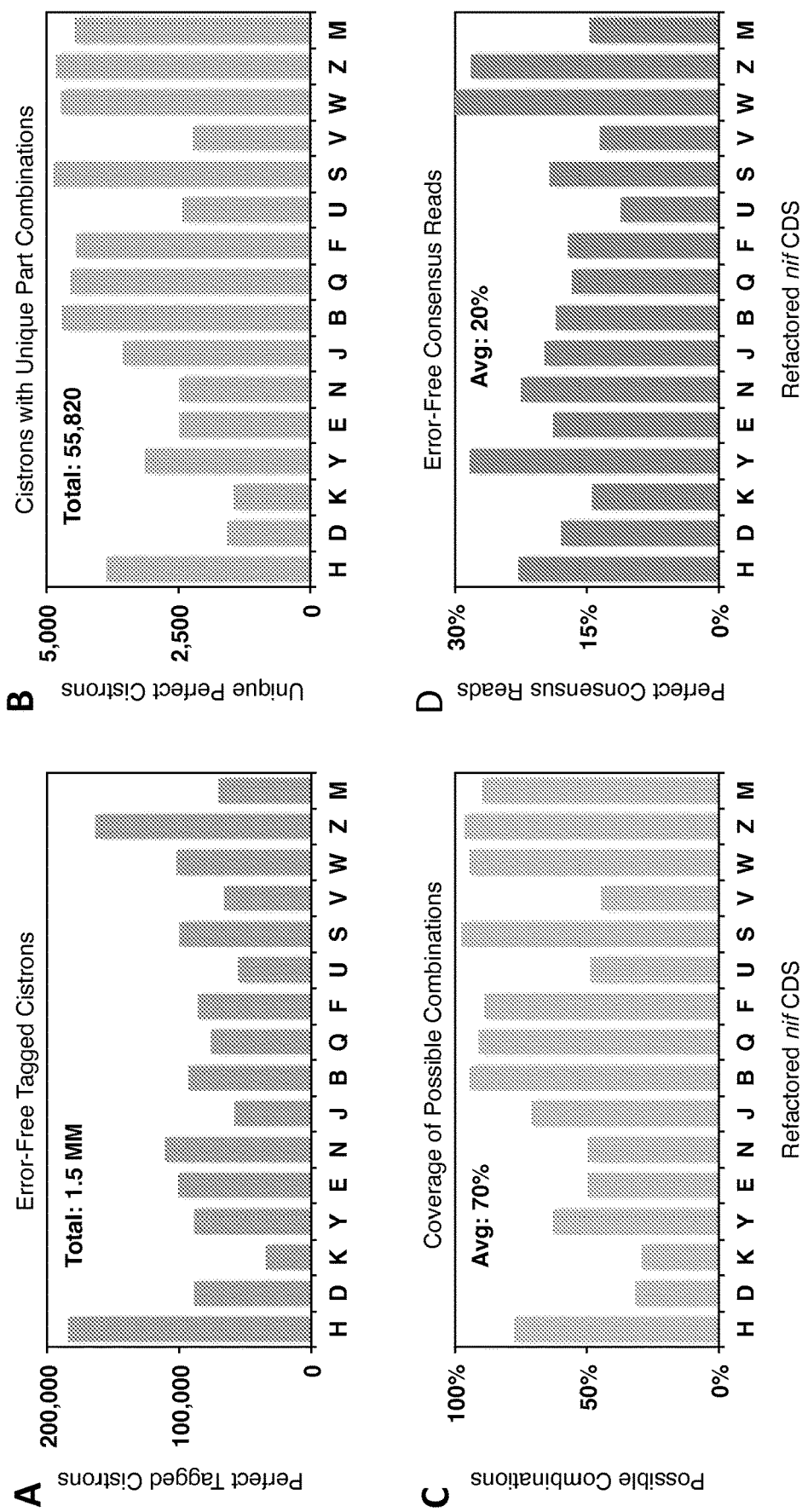
FIGS. 12A-12D are a series of histograms showing the results of sequencing a library of nif cistrons assembled using presently disclosed methods, including 1.5 million error-free tagged cistrons (FIG. 12A) and 55,820 cistrons with unique part combinations (FIG. 12B). For each refactor nif CDS, an average of 70% of possible combinations (FIG. 12C) and 20% error-free consensus reads (FIG. 12D) were found.
Figure 13:
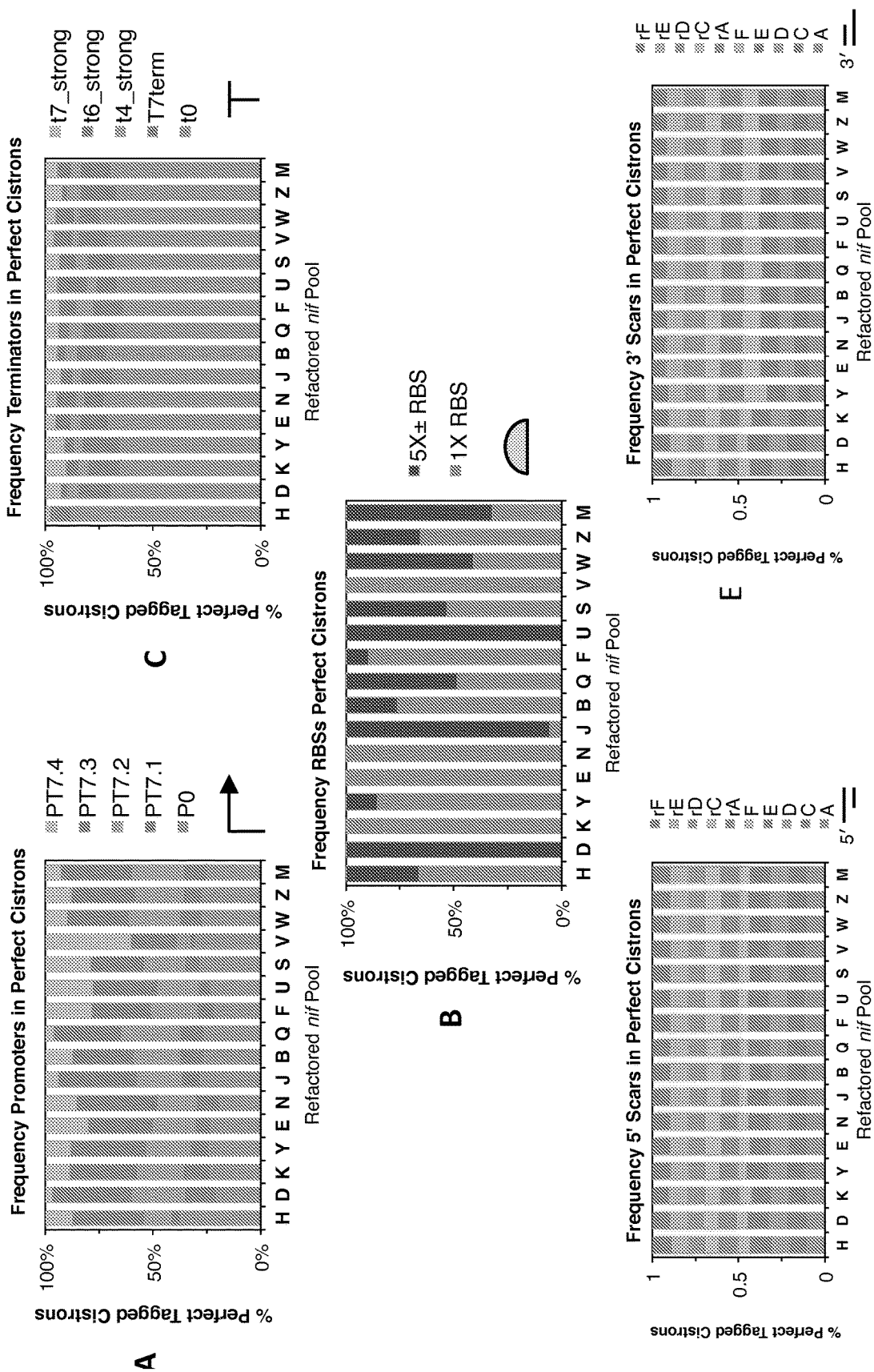
FIGS. 13A-13E are a series of graphs showing that the lower coverage of some pools is largely due to uneven representation of parts, including (A) promoters, (B) ribosomal binding sites (RBS), (C) terminators, (D) 5' scars, and (E) 3' scars.
Figure 14:
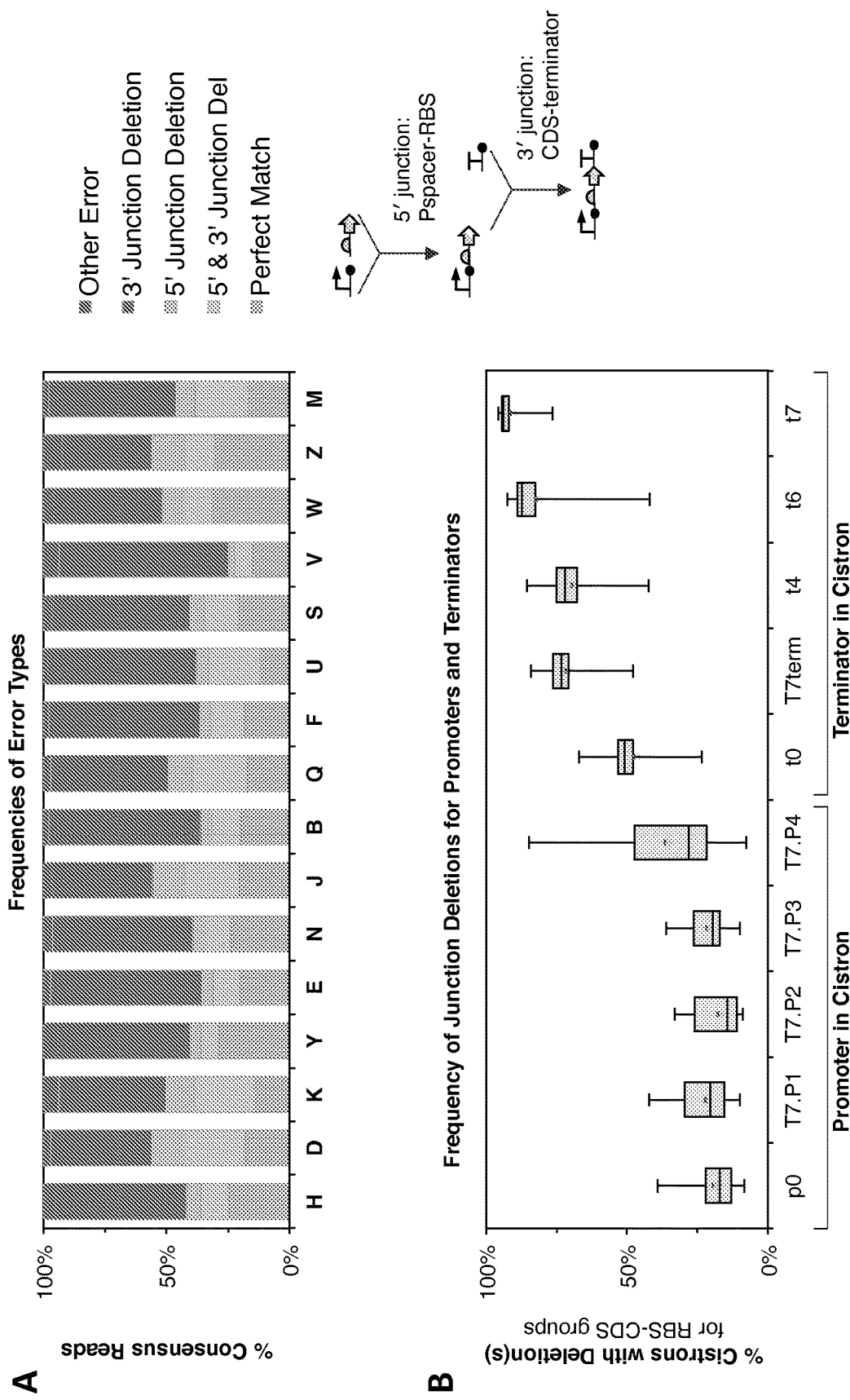
FIGS. 14A and 14B are a series of graphs showing (A) frequencies of error types and (B) junction deletions for promoters and terminators in 7.5 million tagged and sequenced cistrons.

Using this method, a library of error-free, unique, sequence-verified nif cistrons was constructed, including 2 gigabases (Gb) of error-free cistrons and 72 megabases (Mb) of cistrons having unique part combinations (FIG. 12). In total, 1.5 million error-free, tagged cistrons were produced (FIG. 12A), of which 55,820 featured unique part combinations (FIG. 12B). An average of 70% of all possible combinations was recovered for each of the 16 refactored nif CDS pools (FIG. 12C). An average of 20% of cistron consensus reads were error-free per refactored nif CDS (FIG. 13D). The lower coverage observed in some pools was largely due to an uneven representation of parts (FIG. 13A-13E). For example, the t0 terminator sequence predominated in each of the refactored nif pools (FIG. 13C). 7.5 million tagged cistrons were sequenced to identify scarless stitching error modes and frequencies (FIG. 14). We found that 3' junction deletion was the most prevalent error mode (FIG. 14A), which was corroborated by data showing that the frequency of junction deletions was higher in terminators than in promoters (FIG. 14B).

Figure 16:
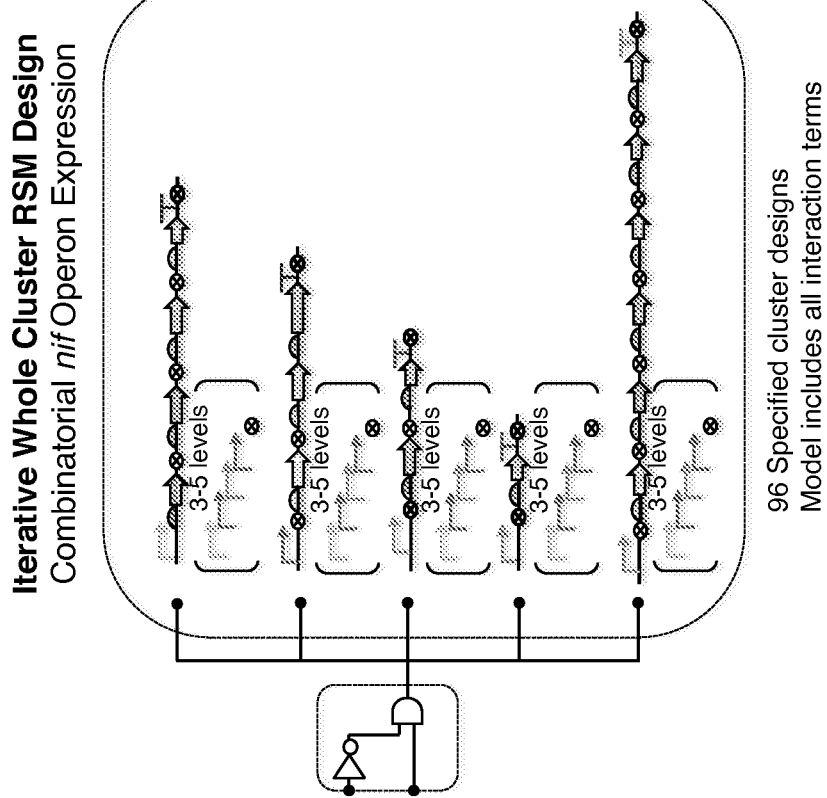
FIG. 16 is a diagram showing iterative whole cluster response surface methodology (RSM) design for combinatorial nif operon expression.

Next tag-directed retrieval of sequence-verified DNA molecules was performed using two different methods: gene synthesis from pooled oligos (FIG. 15A; Kosuri et al., Nat. Biotechnol. 28(12): 12951299, 2010) and dial-out PCR (FIG. 15B; Schwartz et al., Nat. Meth. 9: 913-915, 2012). Each of the above-listed references is incorporated herein in its entirety. Cistrons from all 167 pools were successfully retrieved, cloned, and sequenced, yielding a 93% error-free sequence rate. This confirms that this approach can be successfully utilized for iterative whole cluster response surface methodology (RSM) design (FIG. 16). Of the 44 cistrons sequenced, three contained one to two single nucleotide polymorphisms (SNPs), of which at least one was generated during retrieval. The impact of mutation frequency for PCR retrieval was subsequently found to increase with length of cistron retrieved (FIG. 17A) and decrease with improved polymerase fidelity (FIG. 17B). The frequency of a template cistron to retrieve is inversely proportional to the number of PCR cycles necessary to yield 20 nM product concentration (FIG. 17C). In addition, we found that the Illumina HiSeq platform offers significantly improved potential sequencing capacity over the MiSeq platform (FIG. 17D). Alternative approaches for fully sequencing cistrons and larger genetic designs include multiplex "jumping" libraries, primer walking amplification, and Single Molecule Long Reads (FIG. 18).

Figure 19:
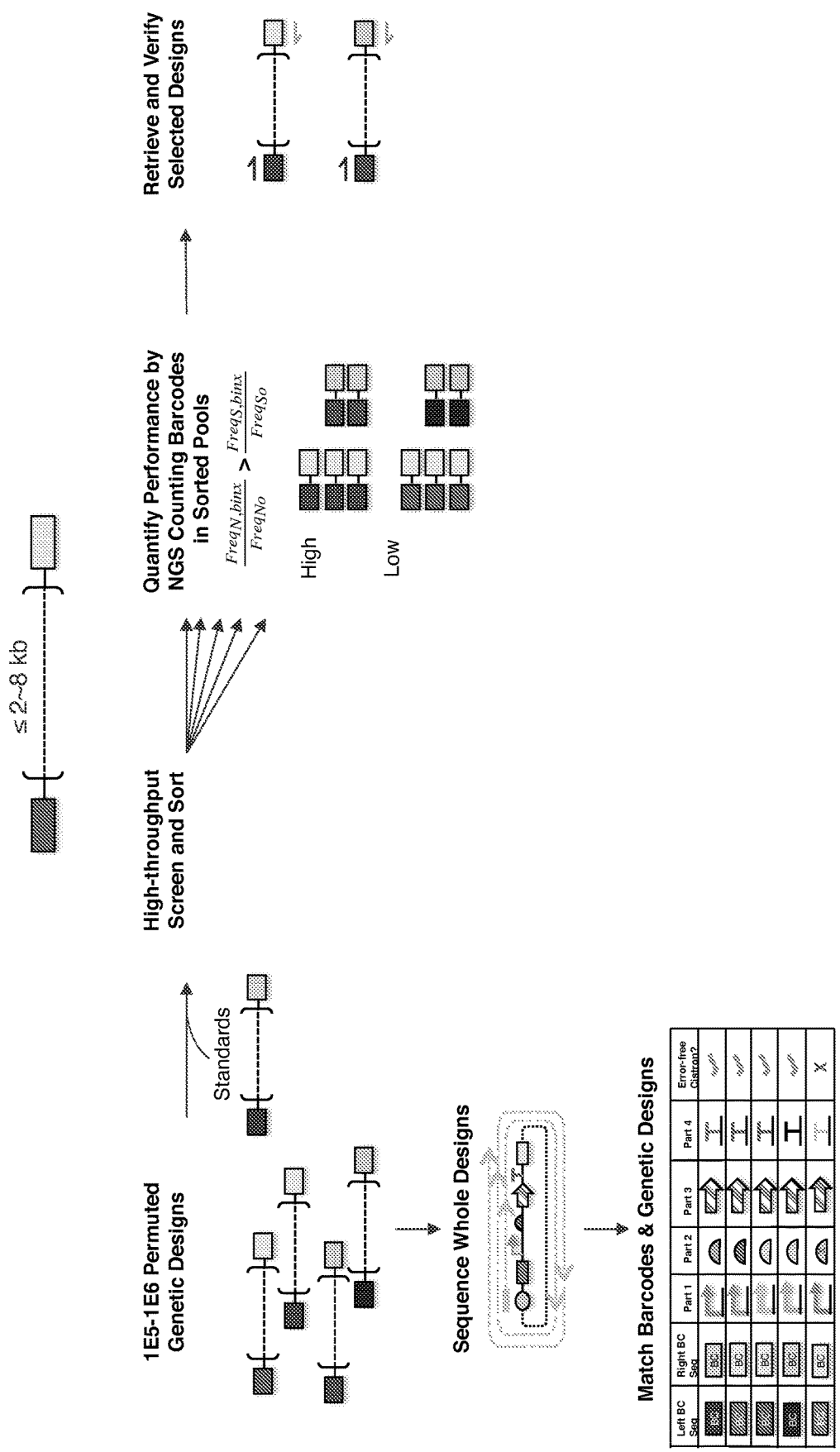
FIG. 19 is a flowchart illustrating how a barcode-tagged genetic design approach can be used with a high-throughput screen to quantitatively track performance of a large number of permuted designs.

In summary, the barcoded genetic design approach disclosed herein can be used in combination with a high-throughput screen to quantitatively track the performance of millions of permuted designs more quickly and inexpensively than existing methods in the art (FIG. 19). This method is ideal for assembling designs of anywhere from less than 2 kb up to 8 kb, on the order of 1E5 to 1E6 permutations at a time. Assembled genetic permutations can then be tested via high-throughput screening, indeed, the constructs of the disclosure can be used to directly quantify performance by next-generation sequencing to identify and count the number of barcodes present in, for example, high-performing pools versus low-performing pools. High-performing designs can then be selectively retrieved and verified.

Example 2

Streamlining DNA Assembly Using Massively One-Pot Assembly

Figure 20:
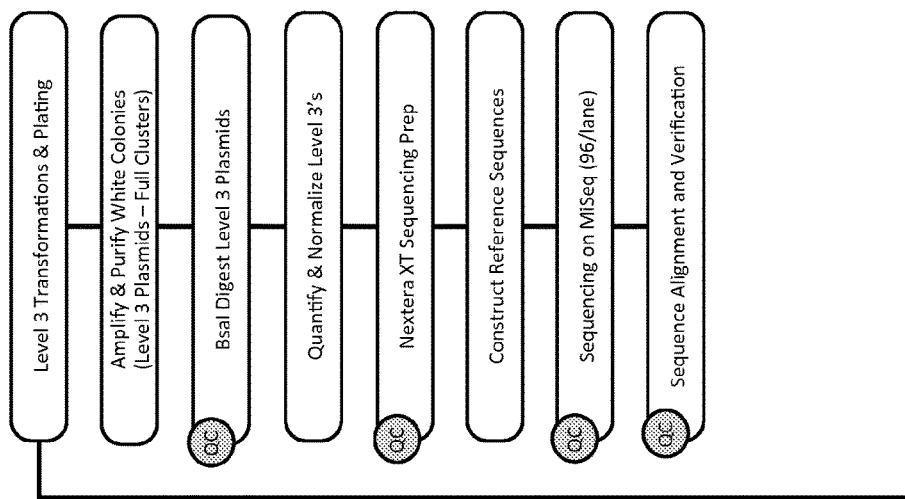
FIG. 20 is a flowchart illustrating a streamlined DNA assembly workflow featuring massively one-pot assembly.

Assembly of designs can be further optimized by minimizing the number of steps required to created ordered concatemers of parts (for example, barcodes, scars, promoters, spacers, RBSs, CDSs, terminators, restriction sites, cistrons, or concatemers of any of the above). A one-pot assembly method was developed for creating ordered cistron concatemers (FIG. 20), involving restriction digest and ligation of parts within the same reaction. This method takes advantage of the fact that the 4-bp cleavage sites present in the restriction sites for Type IIs restriction enzymes (for example, BsaI, BbsI, and MlyI) may include any combination of four nucleotides, as the enzyme recognition site is separated from the cleavage site. Thus, we can use the cleavage site as a means for storing information about the identity of the part or cistron as well as establish an ordering system, by using predefined 4-bp sequences for each junction between parts or cistrons to be ordered. This approach allowed for the hierarchical assembly of entire cistron clusters based on sequence complementarity of the overhangs produced after enzymatic cleavage (FIG. 21). For example, cistrons 1,2, and 3 can be assembled in that order if: cistron 1 is flanked by scars "a" and "b," cistron 2 is flanked by scars "b" and "c," and cistron 1 is flanked by scars "c" and "d." This can be used to produce "first-order" concatemers in plasmids, which can in turn be assembled with, for example, other first-order concatemers, clusters, or scarless cistrons, to form larger assemblies (for example, a quarter cluster in a second-order plasmid). This process can be repeated multiple times to produce complete refactored clusters.

Figure 22:
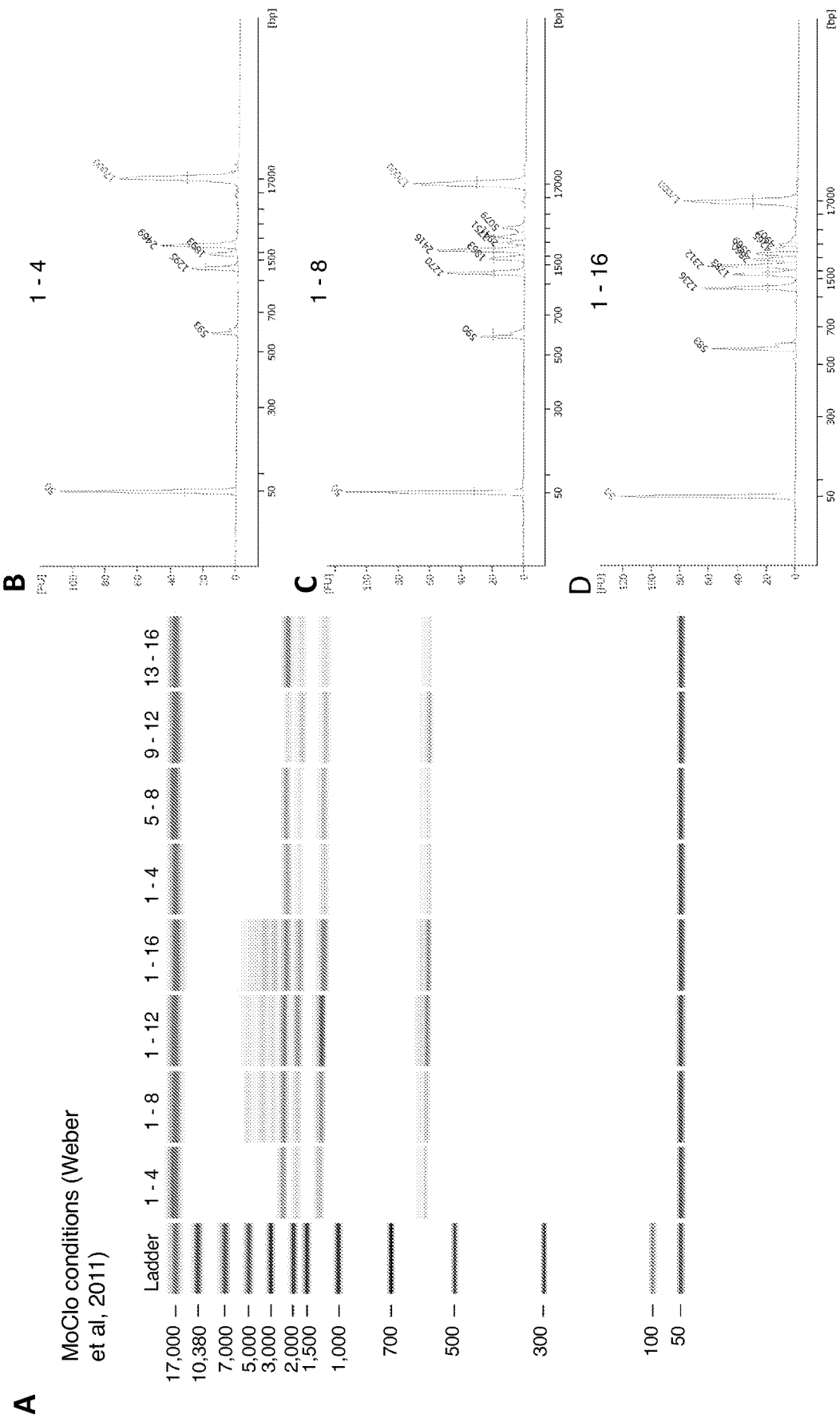
FIGS. 22A-22D are an electrophoresis gel and a series of graphs showing size distribution and extent of reaction (~) for a series of assembly reactions performed as described in FIG. 21.
Figure 24:
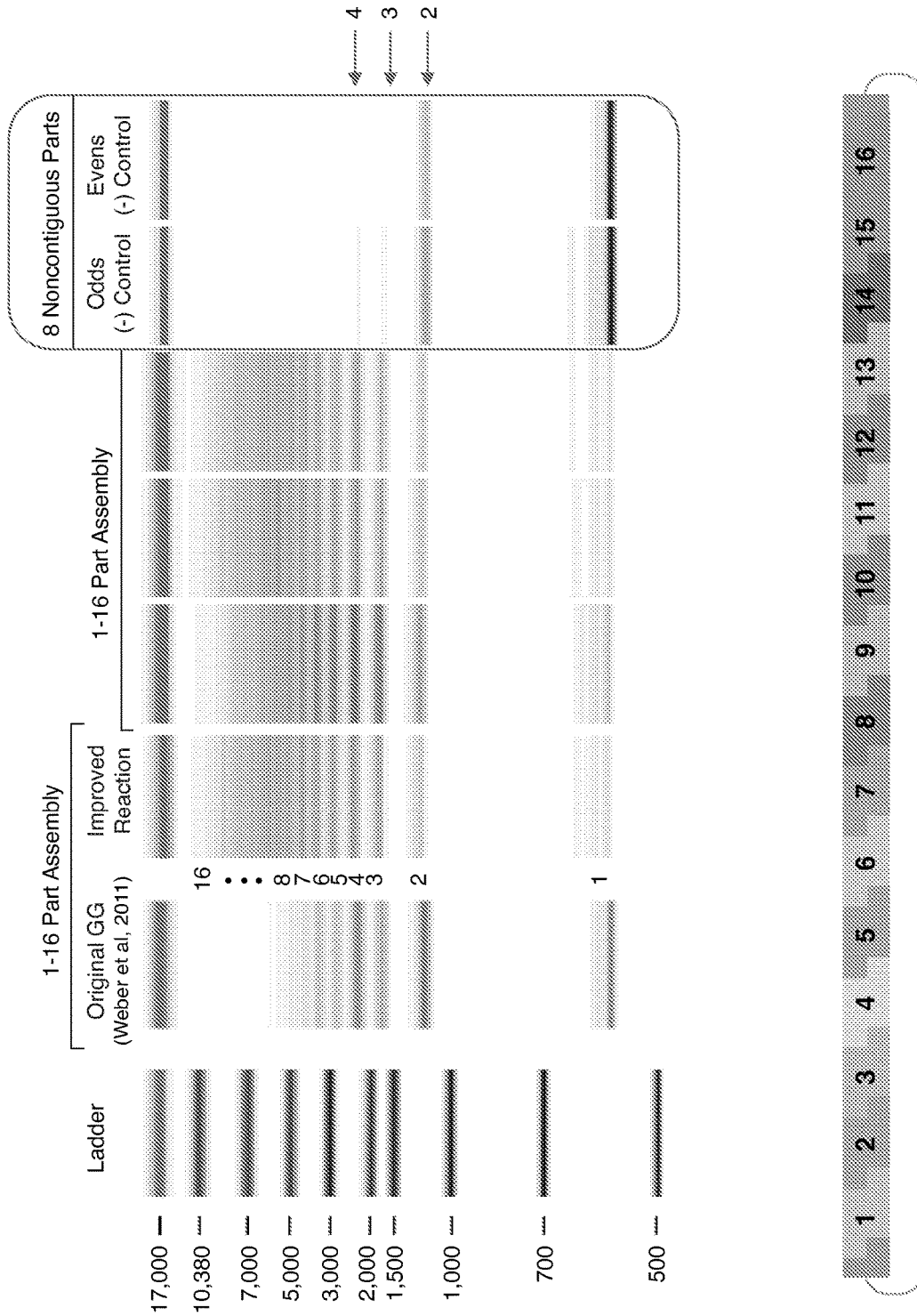
FIG. 24 is an electrophoresis gel showing that the engineered reaction conditions produce full-length product but nonspecific assembly.
Figure 25:
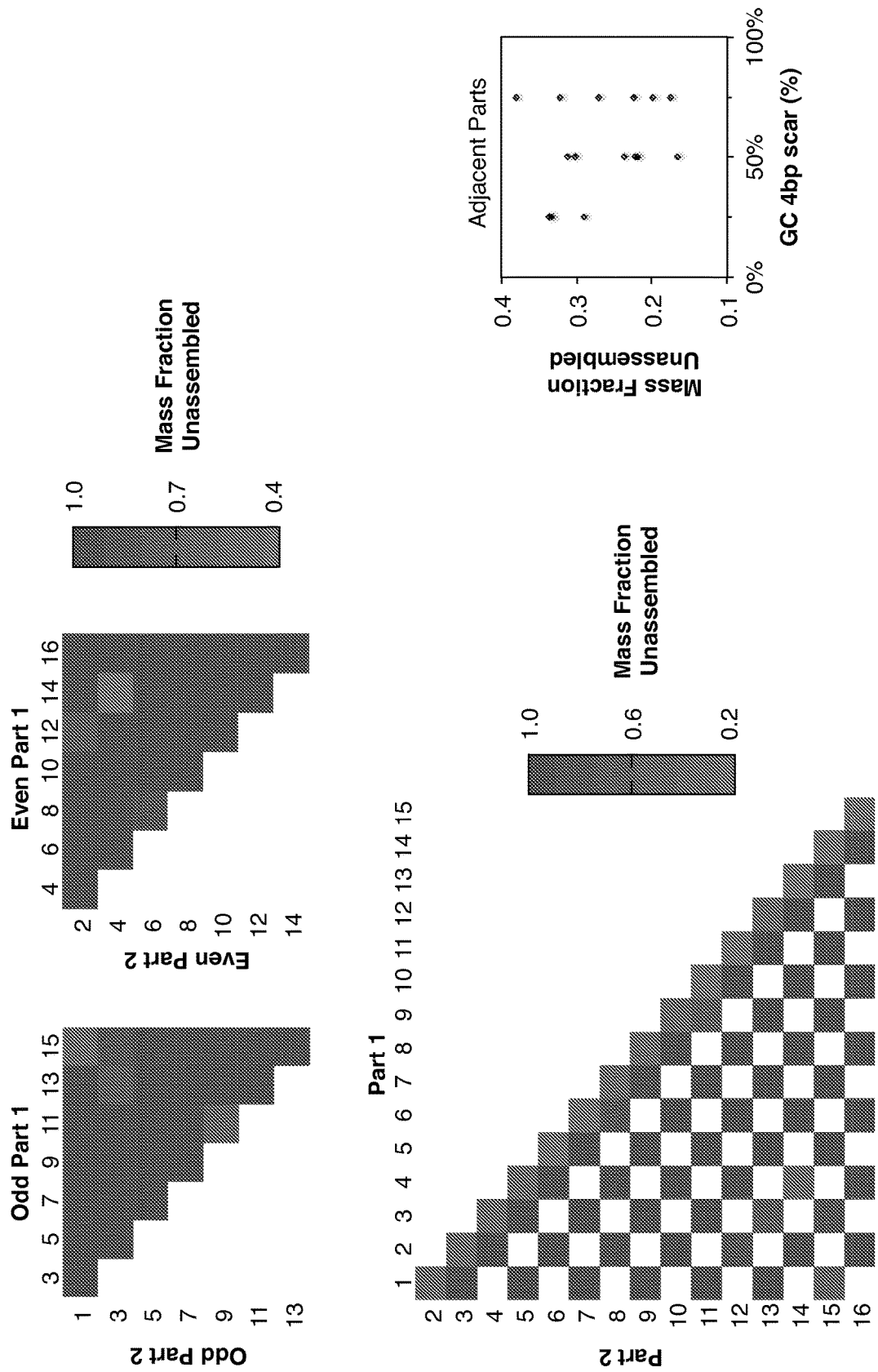
FIG. 25 is a series of diagrams illustrating the testing of pairwise assembly to identify design rules for cohesive end specificity.
Figure 26:
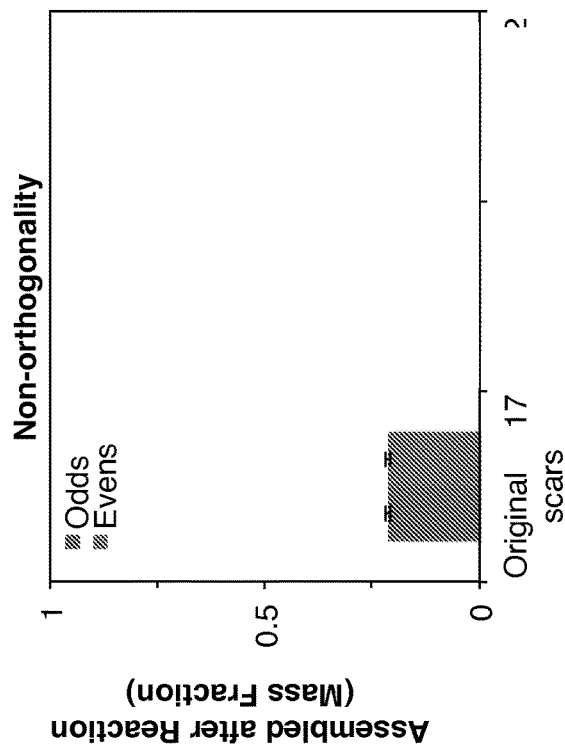
FIG. 26 is a diagram showing refined design rules for cohesive ends and illustrating how the refined design rules were used to computationally redesign sets of orthogonal cohesive ends to improve specificity of assembly 15-fold.
Figure 27:
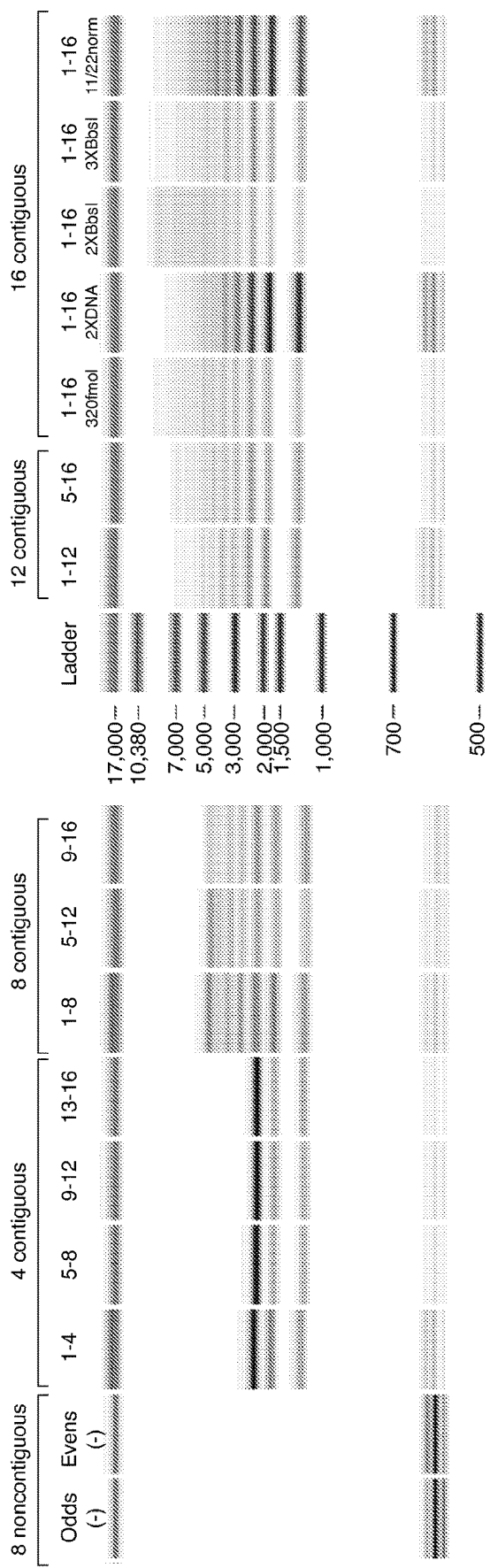
FIG. 27 is a pair of electrophoresis gels showing assembly reactions of 16 parts using redesigned scars.
Figure 28:
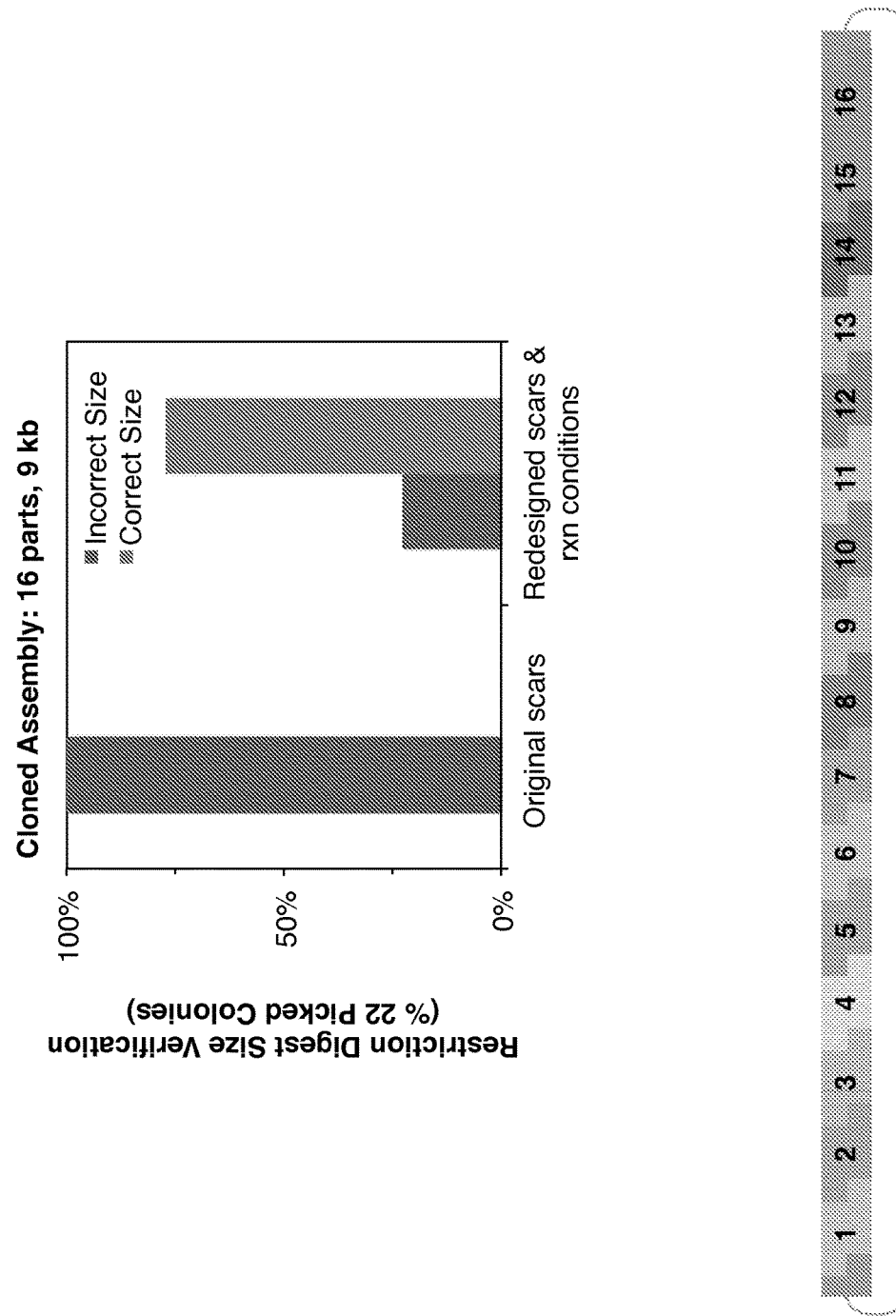
FIG. 28 is a graph showing that using the redesigned scars and new reaction conditions resulted in a dramatic increase in the number of colonies containing the correctly sized, full-length insert, from 0% to 77%.
Figure 30:
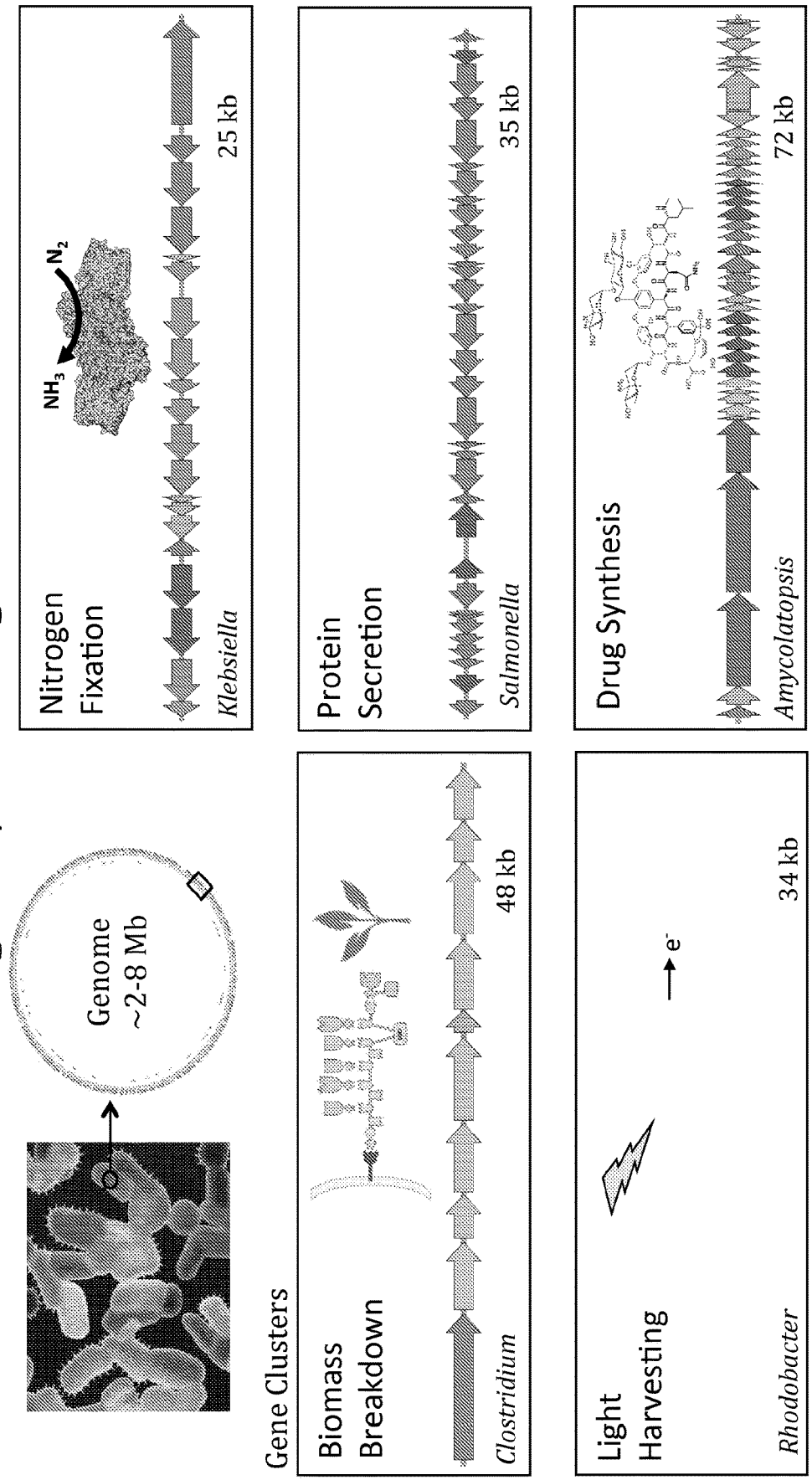
FIG. 30 is a set of schematics showing the potential biosynthetic pathways that can be permuted with the disclosed methods.
Figure 32:
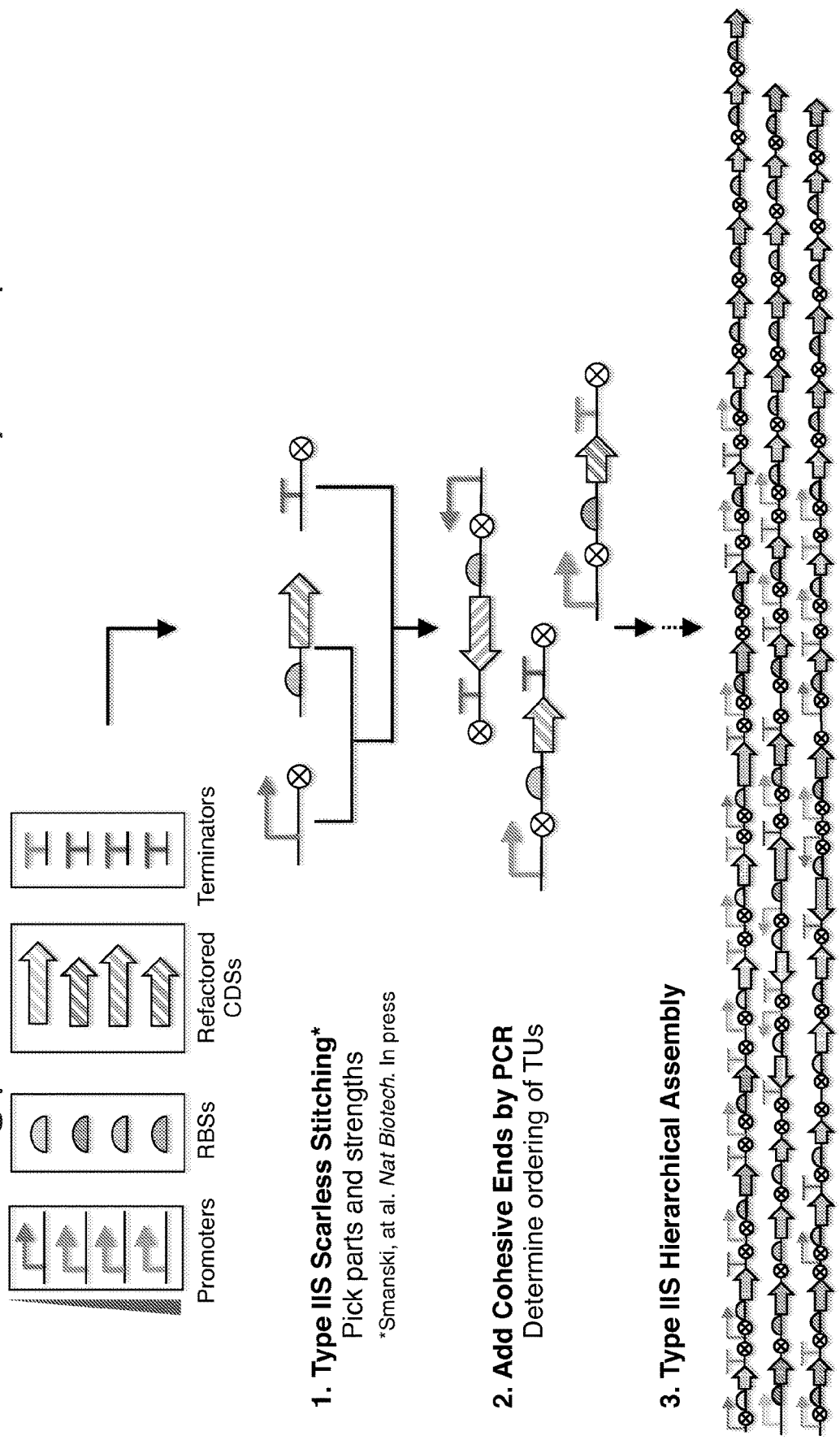
FIG. 32 is a schematic showing how permuted gene clusters can be built from parts making up gene expression elements.
Figure 34:
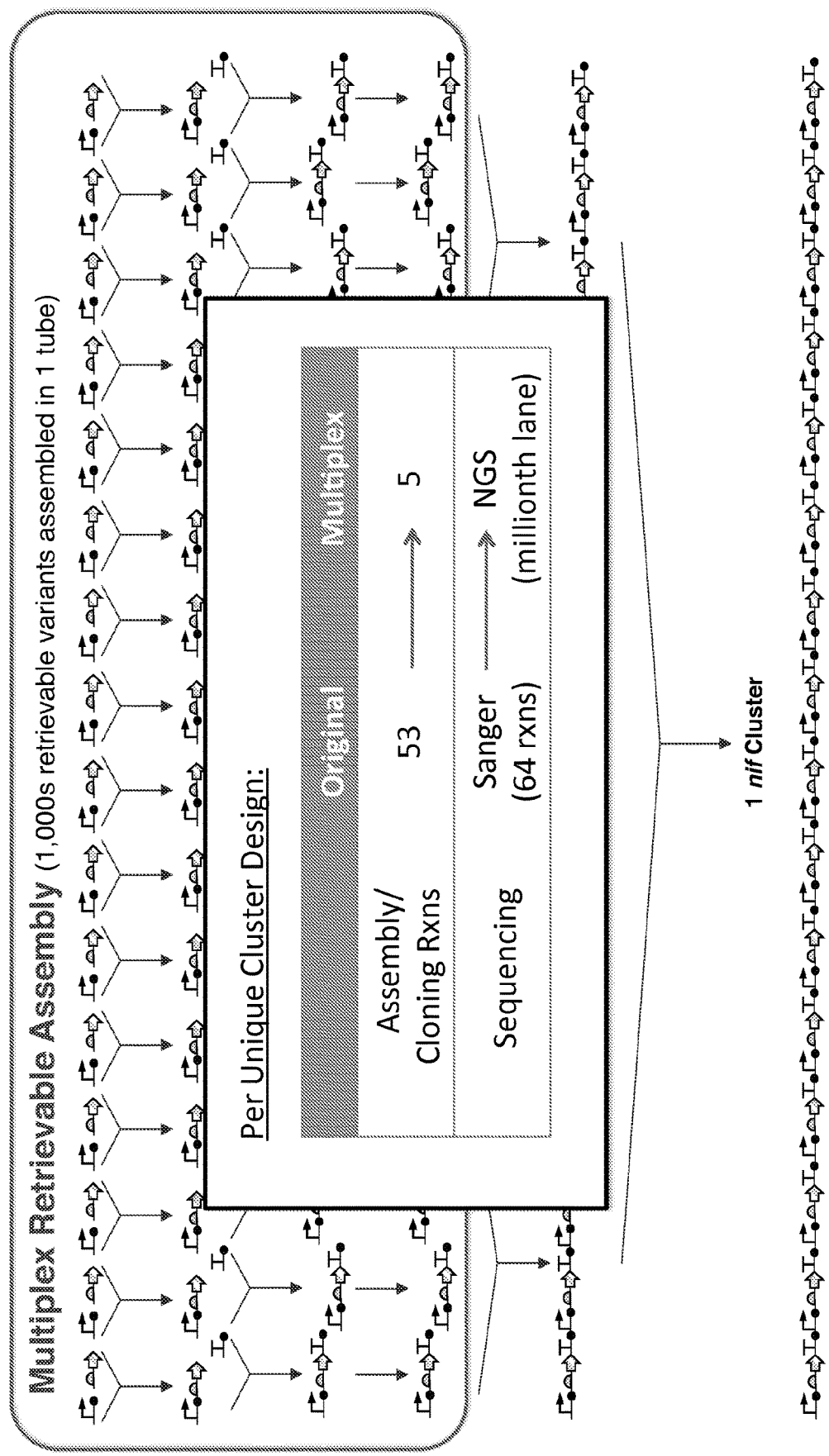
FIG. 34 is a schematic showing the construction of gene expression libraries using retrievable gene expression elements.
Figure 35:
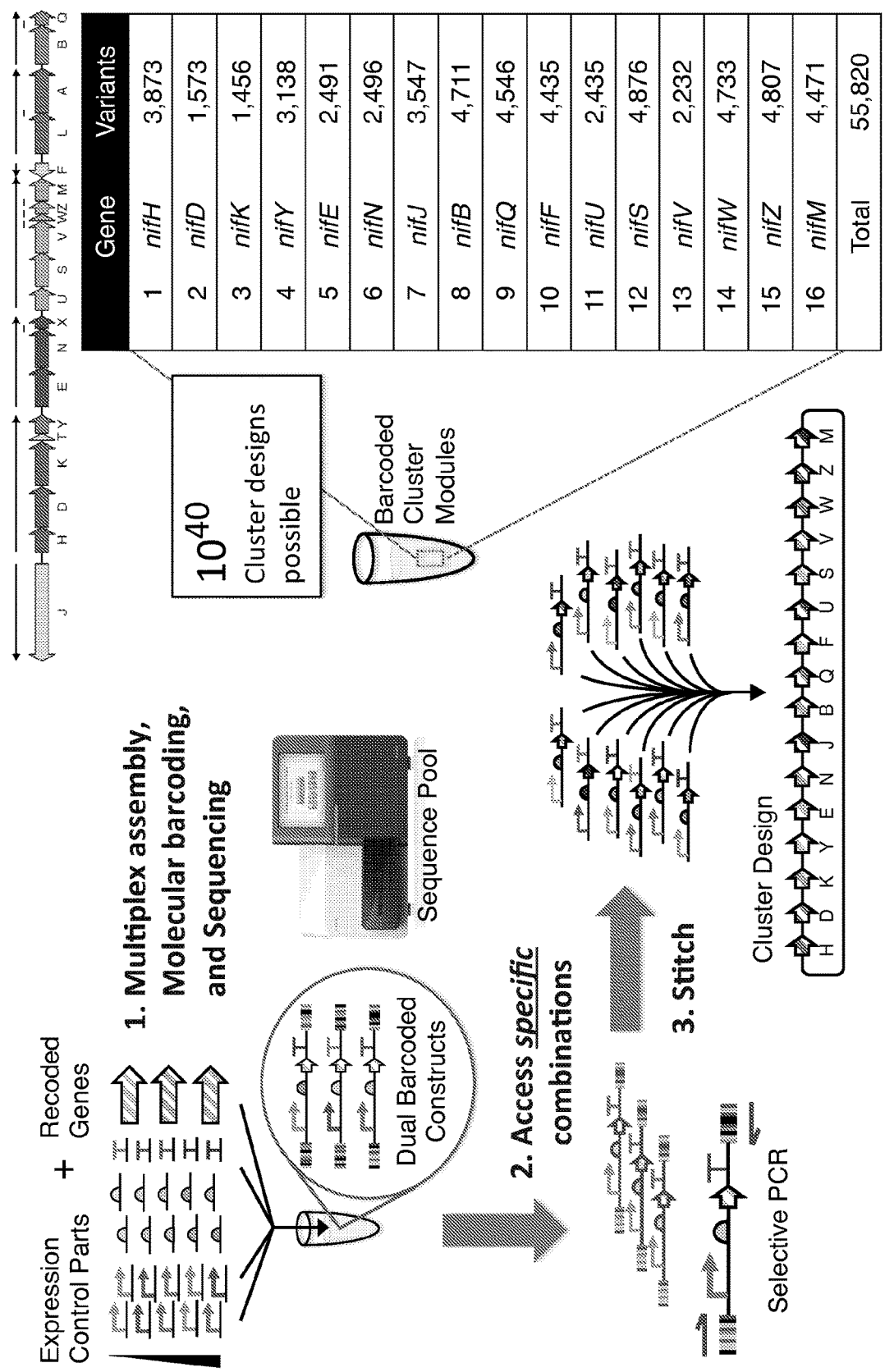
FIG. 35 is a schematic showing the exemplary design of a library of nitrogen fixation gene clusters using the disclosed combinatorial approach.
Figure 36:
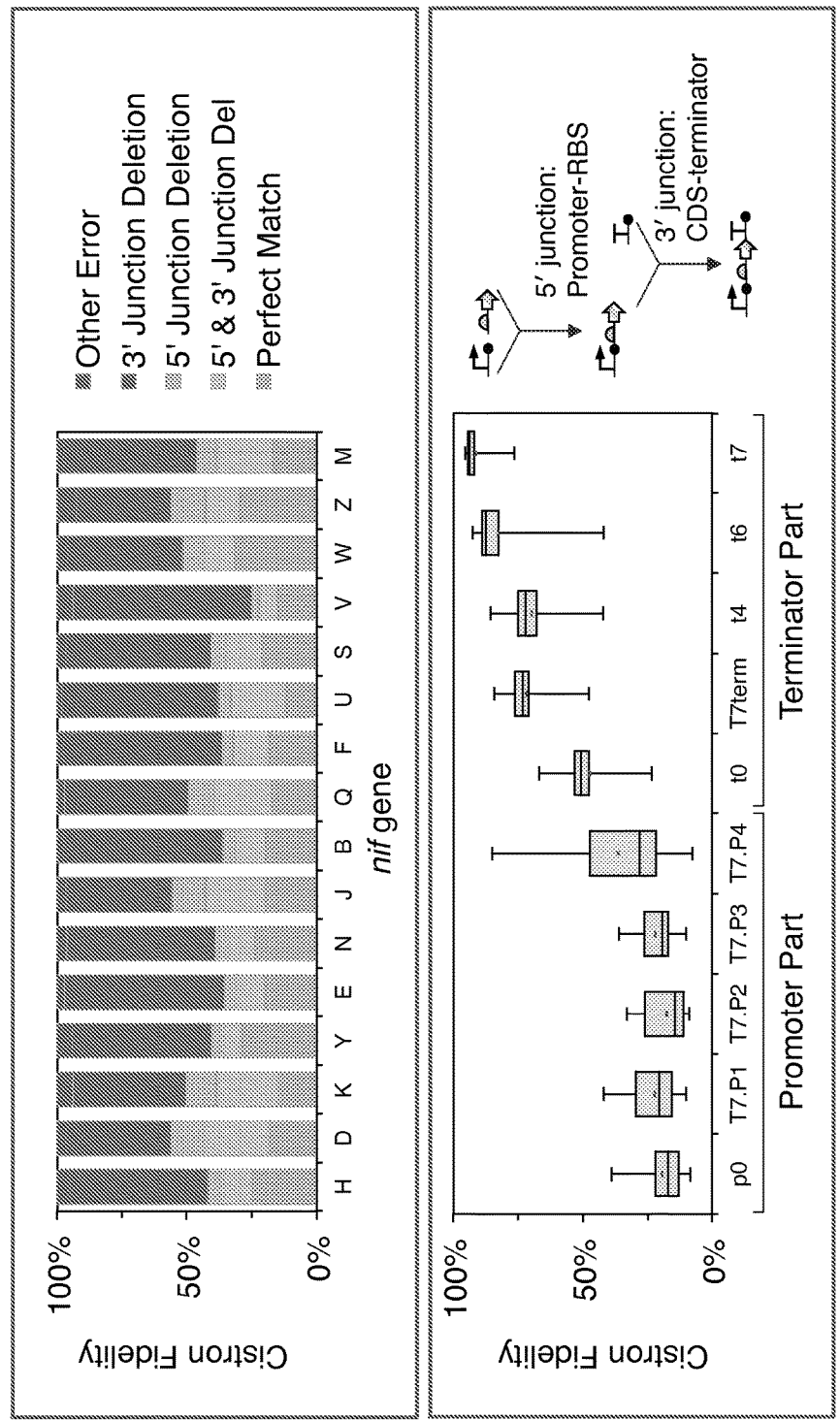
FIG. 36 is a set of graphs and schematics showing the fidelity and errors encountered during assembly of cistrons.
Figure 37:
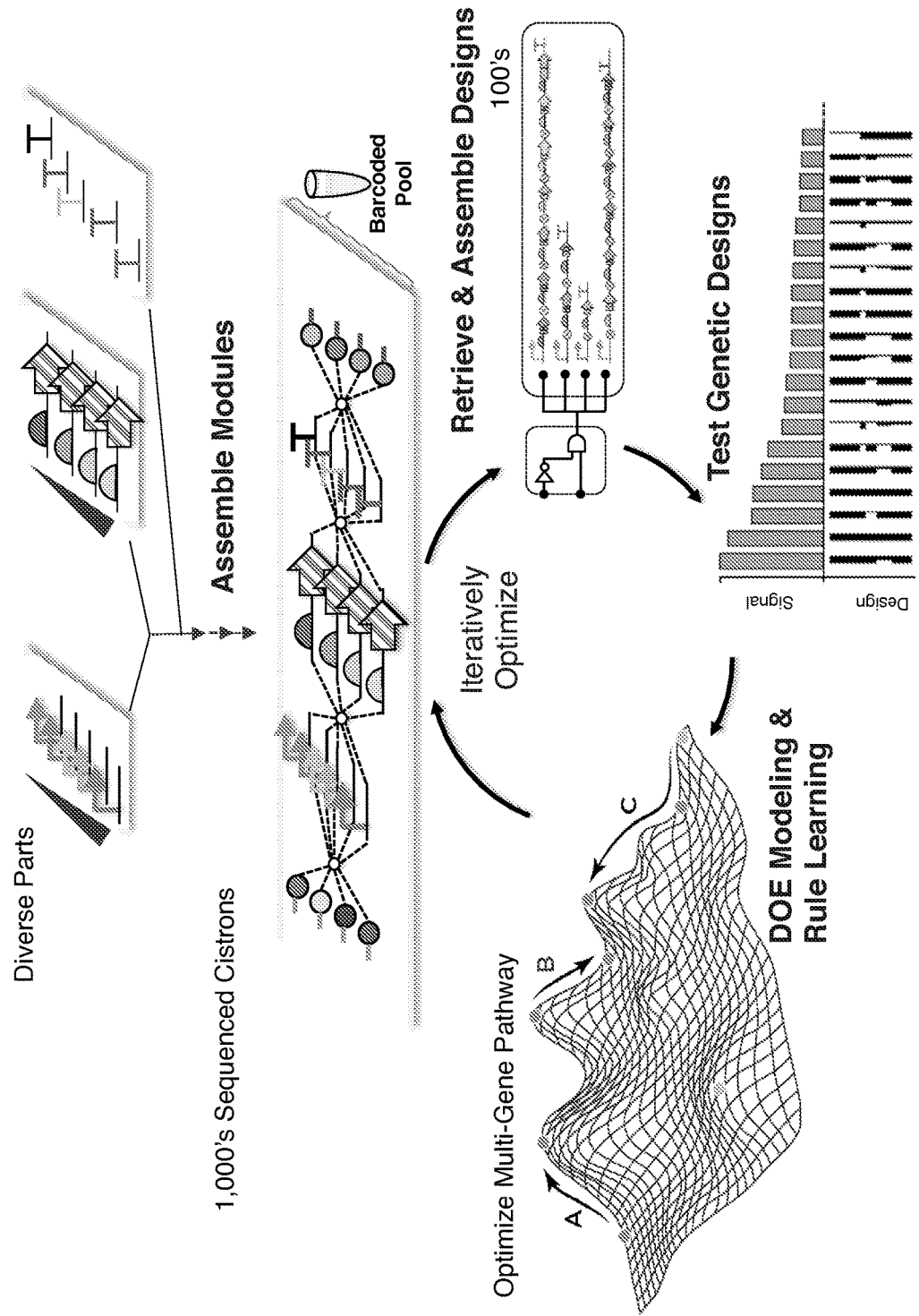
FIG. 37 is a schematic showing the iterative process of permuting a multi-gene pathway using the disclosed methods.
Figure 38:
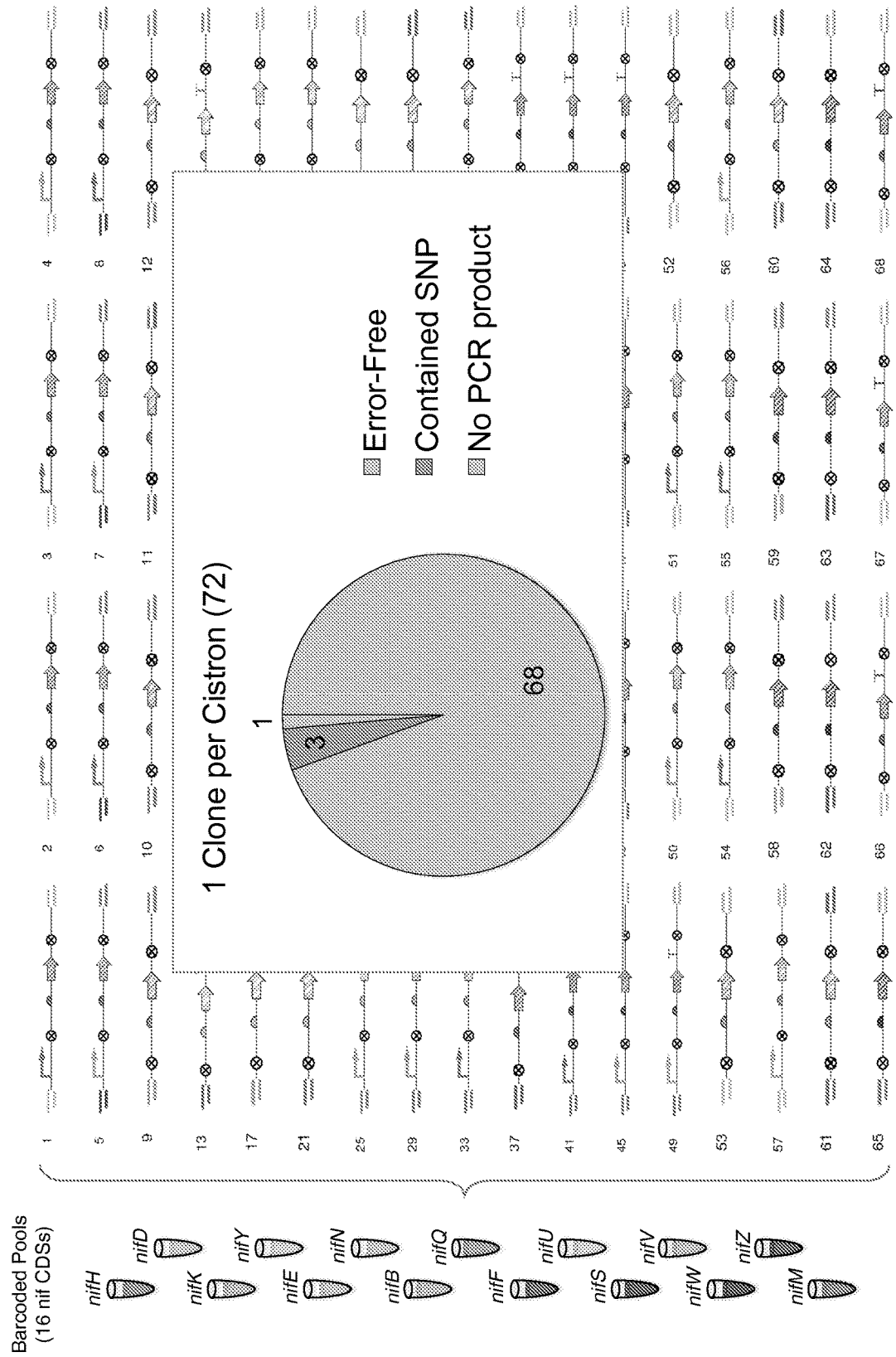
FIG. 38 is a schematic showing that cistrons retrieved from a pool show very little error in sequence, demonstrating the robust nature of the disclosed methods.
Figure 39:
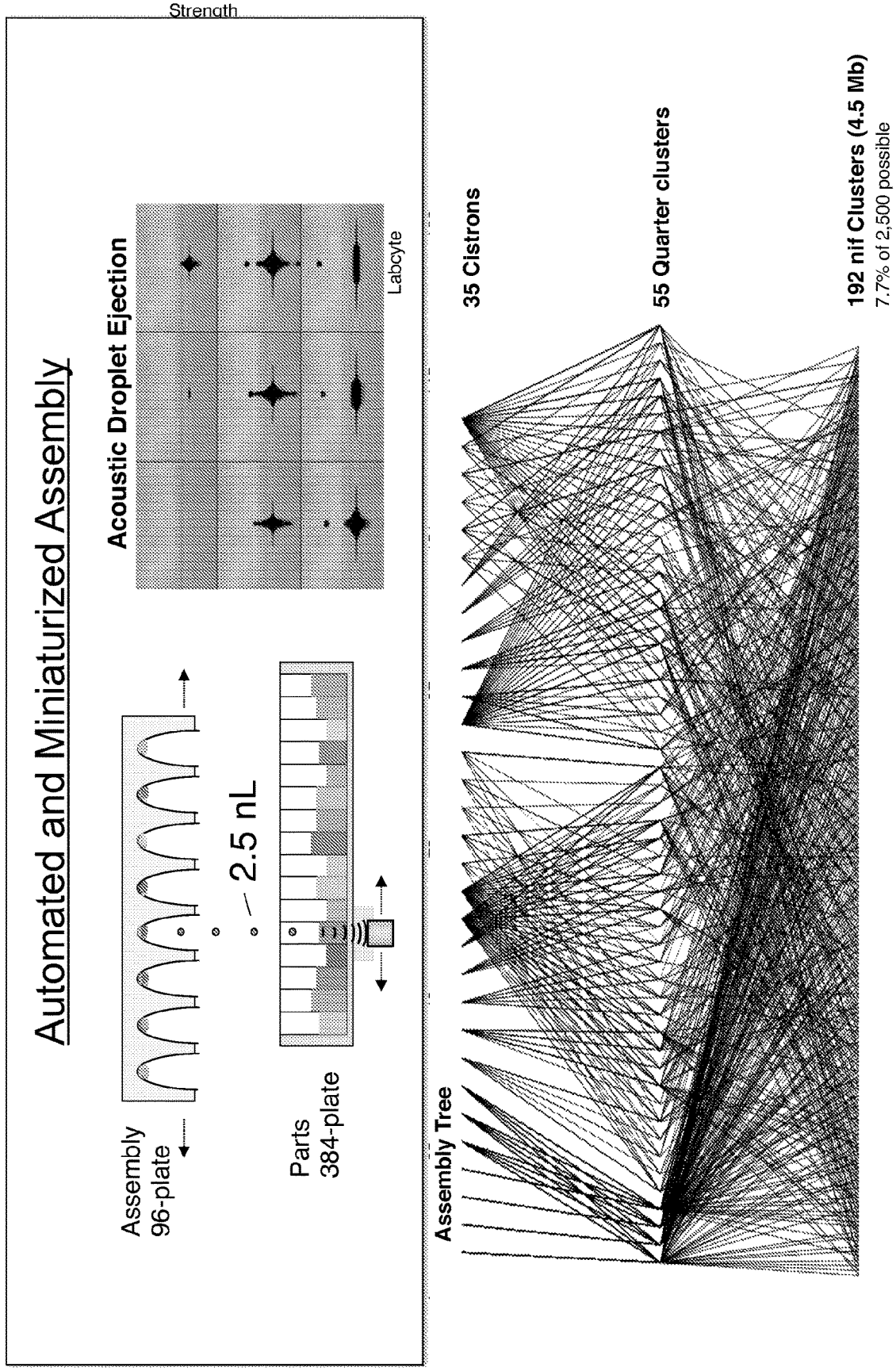
FIG. 39 is a schematic showing the assembly of gene expression elements using microfluidics to position the pieces of the assembly in individual wells of a microtiter plate.
Figure 40:
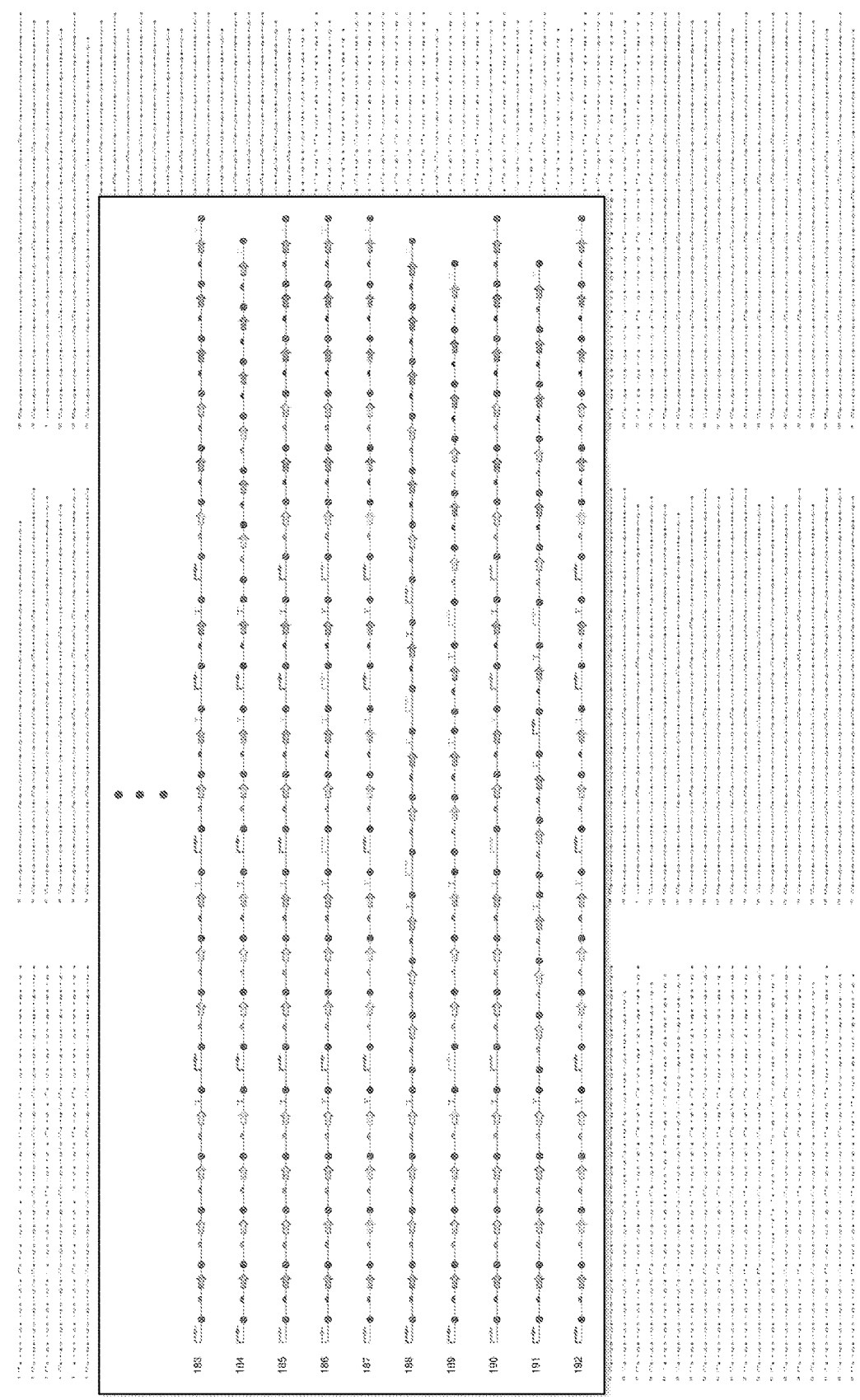
FIG. 40 is a schematic showing the assembly of a diverse library of nitrogen fixation gene clusters.
Figure 41:
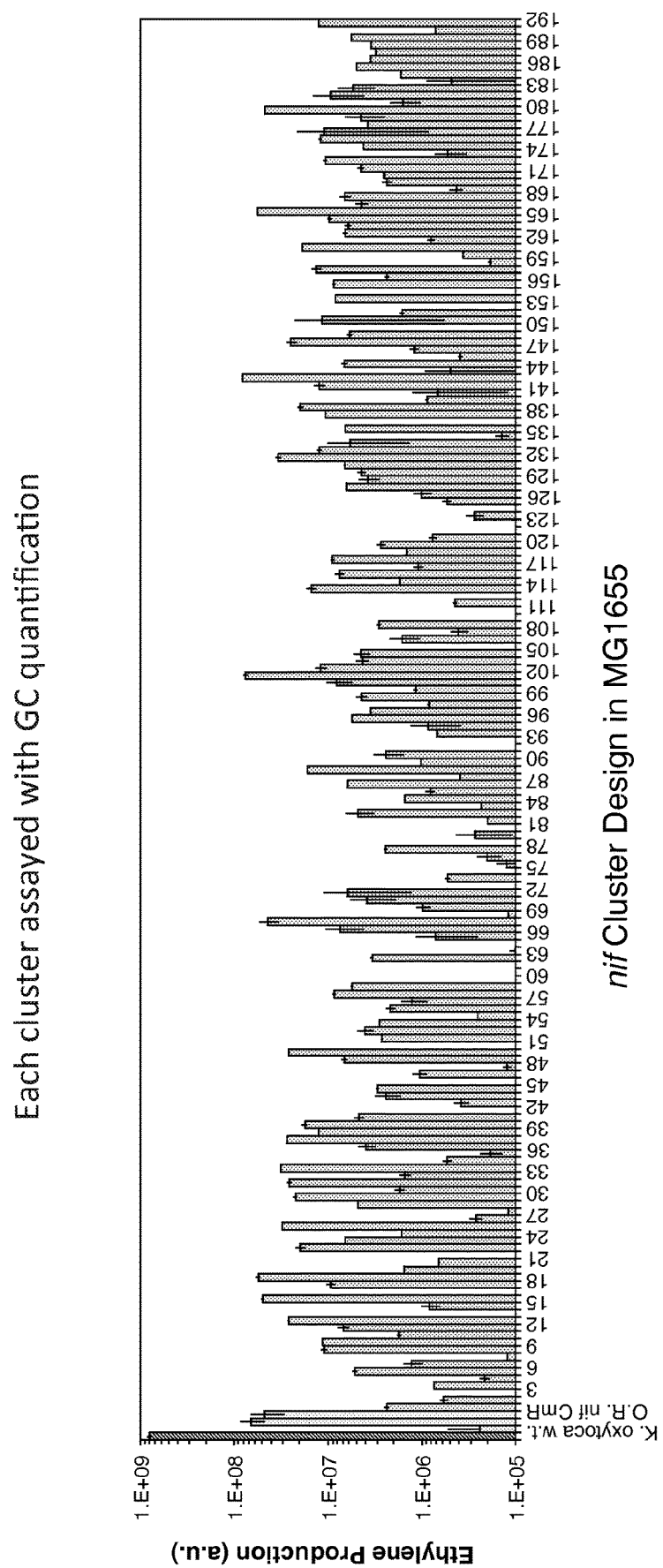
FIG. 41 is a graph showing the readout, as exemplified by ethylene product of the different nitrogen fixation gene clusters.
Figure 42:
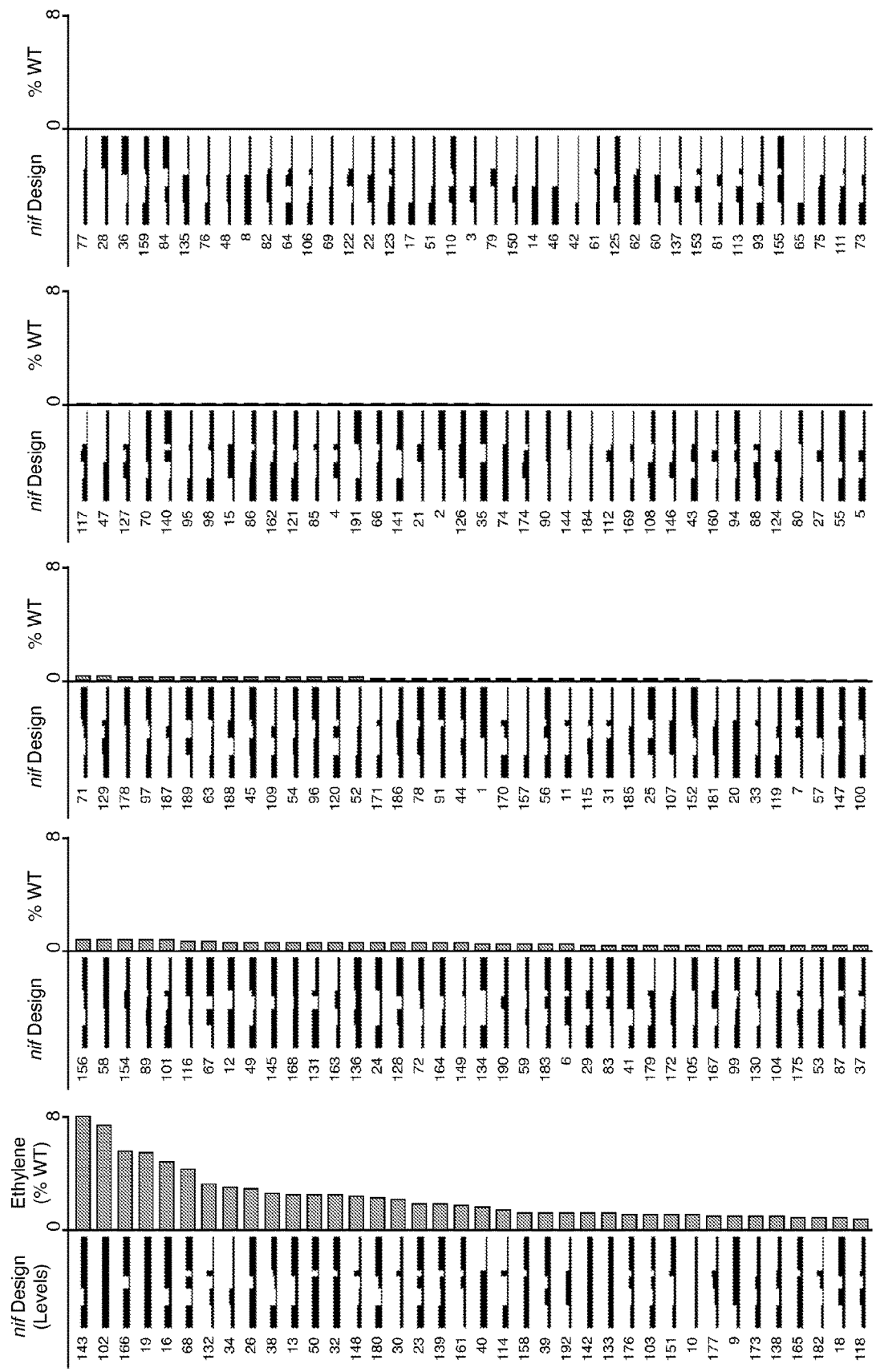
FIG. 42 is a schematic showing activity as mapped to the cluster designs.
Figure 44:
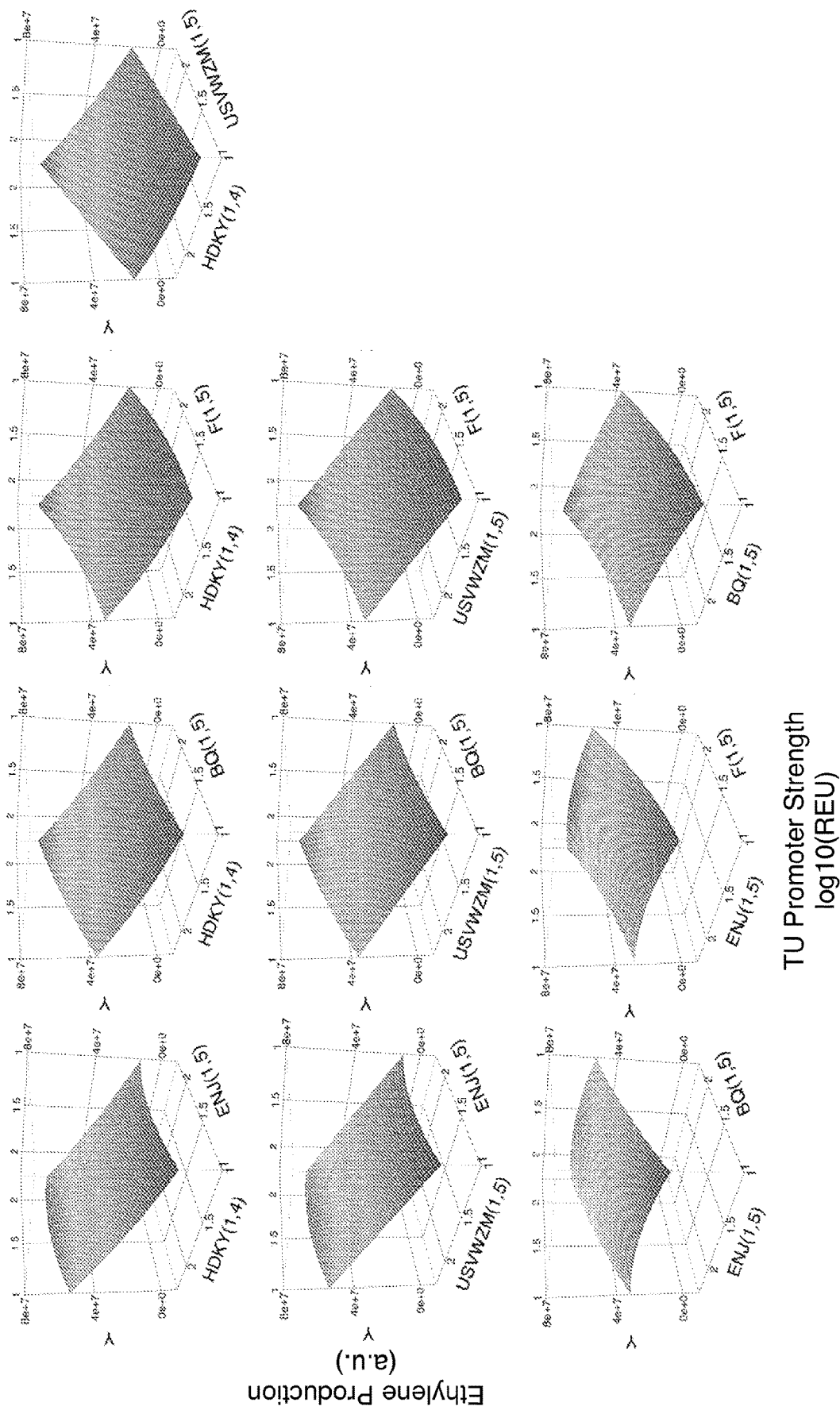
FIG. 44 is a set of graphs showing multidimensional response surface resolved by DOE.
Figure 45:
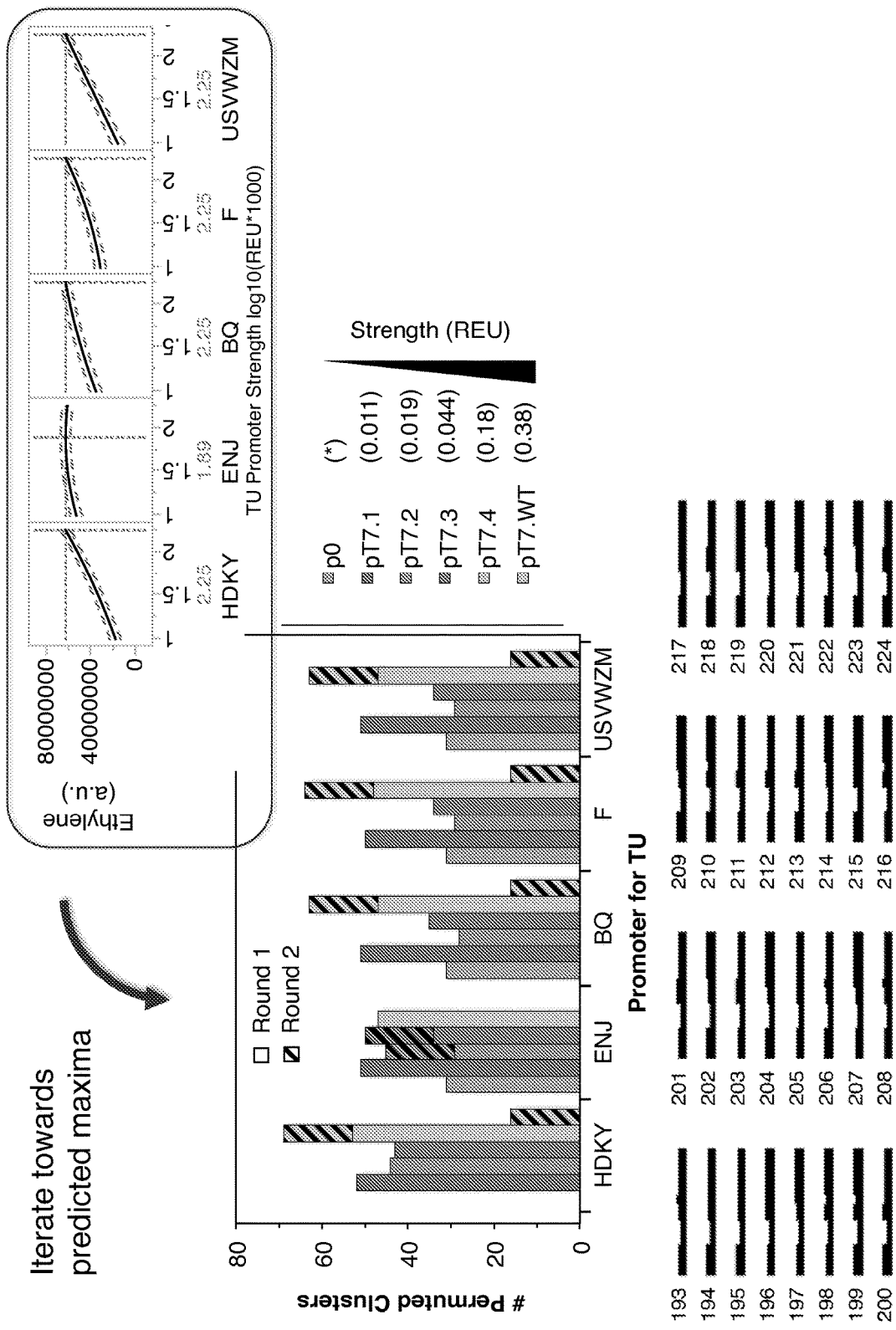
FIG. 45 is a schematic showing how the model based design can be used to predict the response of a refactored gene cluster in an iterative fashion.
Figure 46:
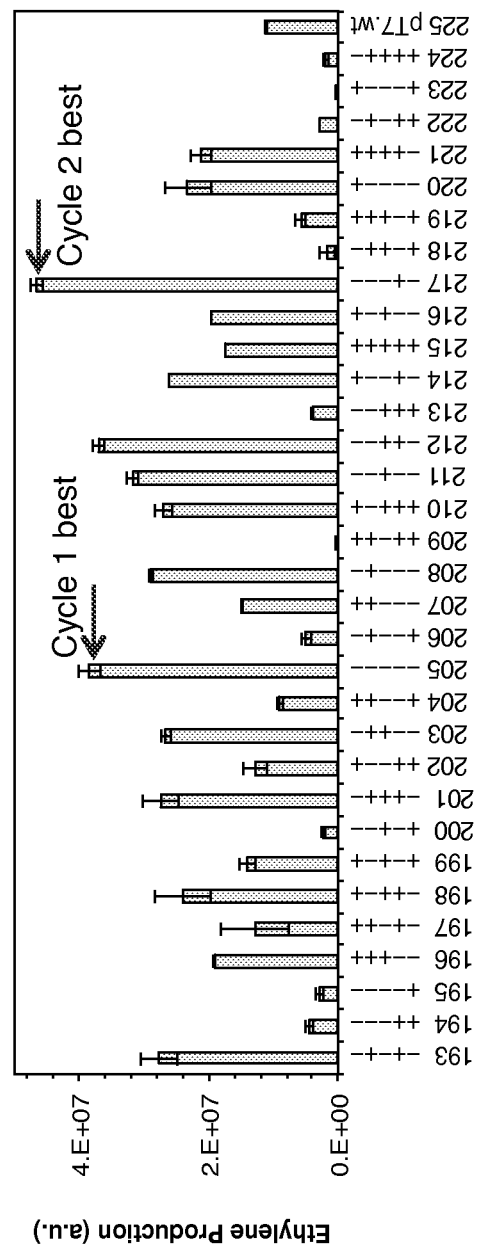
FIG. 46 is a graph showing the increased activity of the model driven iteratively design optimization of the nitrogen fixation gene cluster.

We used two different assembly methods to attempt to construct 16-cistron nif clusters: (1) MoClo, an assembly technique described by Weber et al. (PLoS ONE 6(2): e16765, 2011; incorporated herein by reference in its entirety), and (2) the one-pot hierarchical assembly method (schematized in FIG. 23). As shown in FIG. 23, many reactions occur simultaneously in each massively one-pot restriction-ligation reaction, including restriction digest of parts (in this case, pre-assembled cistrons) from their cohesive ends, step-growth polymerization of digested parts, and competing cohesive ends ligating to growing chains. Crucially, only polymerization of parts is irreversible, as this reaction results in removal of the restriction enzyme recognition sites from the junction. Upon completion of assembly, residual cohesive ends can be removed by a cleanup step. The resultant clusters produced by each method were quantified for size distribution and the extent of the reaction ($\xi$) by capillary electrophoresis. An Agilent Bioanalyzer was used to quantify dilute assembly reactions and resolve peaks. Under MoClo conditions, only assembly of up to eight parts was detected (FIG. 22A). No 16-part cistron clusters were produced by the MoClo method. In contrast, our one-pot hierarchical assembly method successfully produced full-length 16-cistron nif clusters. Analysis of the assemblies produced by one-pot hierarchical assembly showed that full-length product was consistently produced, but that the assembly was often not specific (FIG. 24). We thus endeavored to identify design rules for cohesive end specificity that would permit efficient and consistent ordered assembly. We tested pairwise assembly of parts to determine their assembly specificity (FIG. 25), and used the results to develop refined design rules for cohesive ends. In particular, we found that preferred cohesive ends (1) cannot share greater than 2 nucleotides (nt) with any scar, (2) cannot share greater than 2 nt with the reverse complement of any scar or with the cohesive end itself, (3) must contain at least 1 guanine (G) or cytosine (C), (4) cannot contain more than 3 Gs or Cs, and (5) must be exactly four nucleotides in length (FIG. 26). We built random sets of cohesive ends that satisfy the refined rules, including up to 24 scars using the original set of 10 scar sequences (and a maximum set size of 32 scars), and performed triplicate runs of 1 million steps (1 day each). As a result, we found a significant reduction in non-orthogonality (FIG. 26) compared to cohesive ends produced using the original design rules. We then performed assembly reactions of 16 parts with the redesigned scars and new reaction conditions (FIG. 27). 77% of the resultant colonies contained the full-length insert, compared to 0% from assemblies built using the original scars (FIG. 28). In summary, disclosed herein a method for using massively one-pot Golden Gate cloning for streamlined DNA assembly. We have engineered conditions to increase extent of reaction and yield, and have tested specificity with 70 pairwise assemblies, which we used to computationally design scar sets following refined design rules. As a result, we have improved scar specificity 15-fold, such that for 16-part assemblies, 77% of colonies contain full-length clusters. Implementation of unique parts in the one-pot assembly method described herein us being used to determine failure modes by sequencing, and for possible future RSM reaction optimization (FIG. 29). In particular, whole nif clusters are being assembled containing 16 unique cistrons (21 kb length) and a maximal scar set with short parts containing 31 unique parts (1 kb length). Combinatorial optimization of the reaction conditions is also being performed to further improve yields and extent of reaction. Lastly, we are testing differentiable parts for assembly of larger parts and parts in greater numbers.

Example 3

Engineered One-Pot Golden Gate Conditions

I. Assemble Full-Length Insert (Tested for 16 Parts, 9 kb Total)

| | |
|---|---|
| 1.75 µl | NF H$_2$0 |
| 4 µl | 80 nM total equimolar mixed parts (320 fmol) |
| 1 µl | 10× 2.1 buffer NEB (10× CutSmart for BsaI) |
| 1 µl | 1 mM rATP |
| 2 µl | BbsI NEB (10 U) (or 1 µl BsaI, 10 U) |
| 0.25 µl | T4 DNA ligase HC Promega (5 U) |
| 10 µl | total |

1. In thermal cycler: 2 min at 37° C., 5 min at 16° C. for 20-24 hr (180 cycles in fast reaction module).
2. Inactivate at 50° C. for 15 min, at 80° C. for 10 min, and freeze at −20° C. (ligation will continue if held at 0-4° C.).
3. (Optional) Check assembly on a gel or capillary electrophoresis instrument.

II. Assemble Insert into Linear Backbone (Instead of Destination Vector with LacZα to Reduce Background)

To prep linear backbone, inverse PCR is used to amplify the linear backbone from plasmid with flanking scars and Type IIs sites (should be the same Type IIs enzyme as in Part I above). Thoroughly digest with DpnI and gel purify the linear backbone before use to remove circular plasmid background.

| | |
|---|---|
| 8 µl | 16-part assembly reaction above |
| 0.5 µl | 20 nM linear backbone with outer scars and Type IIs sites |
| 0.25 µl | 1 mM rATP |
| 1 µl | NEB BbsI (or 0.25 µl BsaI) |
| 0.25 µl | Promega T4 DNA ligase HC (5 U) |
| 10 µl | Total |

4. Set up backbone assembly. Include negative control with only the linear backbone for counting background CFU.
5. In thermal cycler: 4.5 hr at 37° C., then 15 min at 50° C., then 10 min at 80° C., and then transform or freeze when done.
6. Transform 5 µl of reaction into 50 µl chemically competent cell aliquots. Transform negative control backbone only reaction. Add 100 µl SOC and recover 1 hr. Plate entire recovery (optionally spin down cells to concentrate) on petri dish with appropriate antibiotic (optionally also include X-gal on plates as a control to check for the circular template from the backbone iPCR).
7. Ensure that there are more colonies for the part assembly reactions than for the backbone only negative control reaction. If not, the assembly reactions probably did not work and are only the empty vector.
8. Grow up colonies and digest the purified plasmid to check for insert.

Seventeen scars have been used, to date (listed below in order of use). A linear backbone with A, C flanking scars is used in certain embodiments.

| List of Scars | | |
|---|---|---|
| 1 | A | GGAG |
| 2 | D | AGGT |
| 3 | E | GCTT |
| 4 | F | CGCT |
| 5 | B | TACT |
| 6 | G | TGCC |
| 7 | H | GCAA |
| 8 | In | ACAG |
| 9 | Jn | ACGA |
| 10 | Kn | CAAC |
| 11 | L | CAGA |
| 12 | Mn | CCCA |
| 13 | Nn | CTTA |
| 14 | On | GATA |
| 15 | Pn | GTGA |
| 16 | Q | CCAT |
| 17 | C | AATG |

Example 4

Assembly of Genetic Circuits

Figure 50:
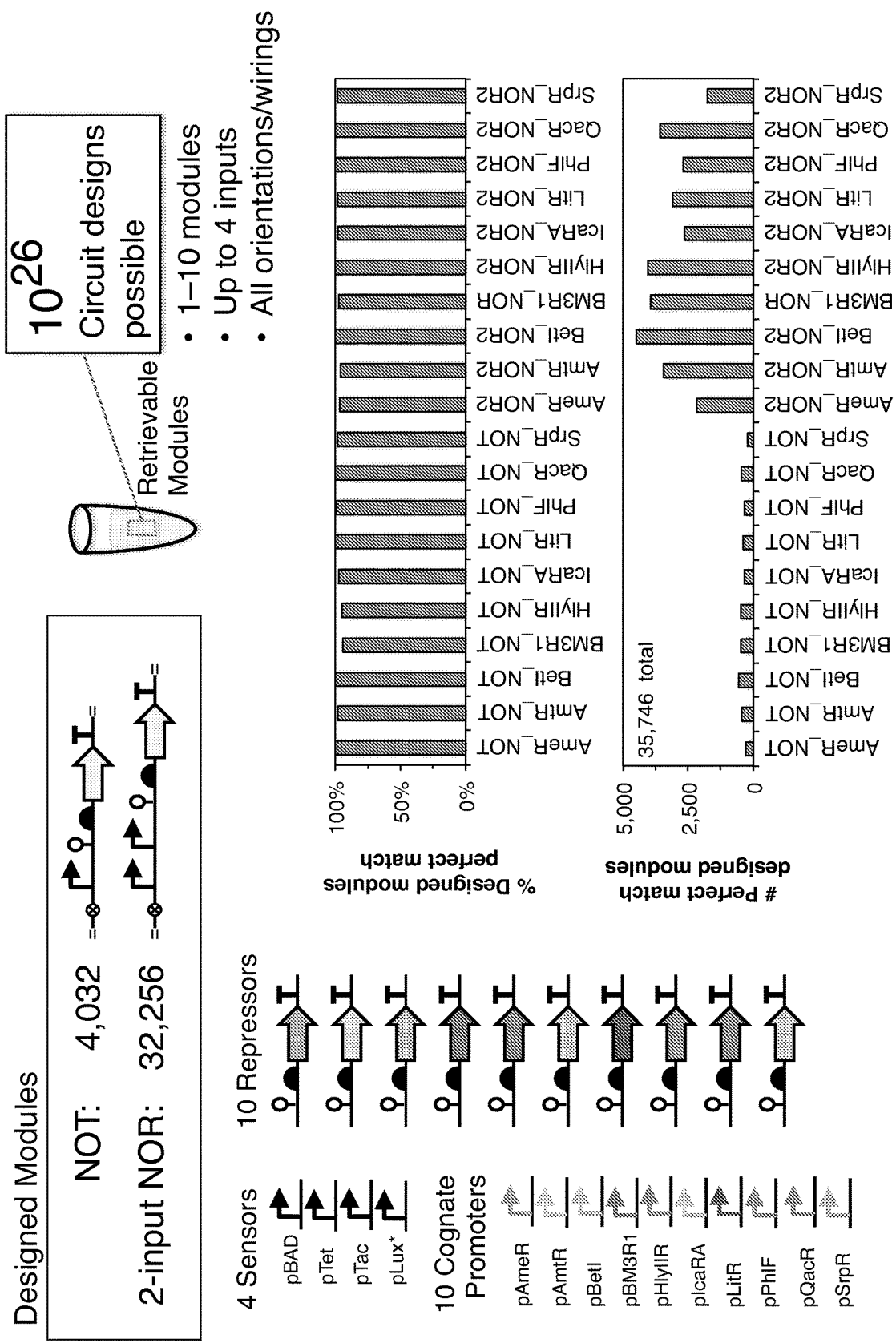
FIG. 50 is schematic showing biological circuit design.

Multiplex pools were constructed containing 3,882,240 perfect match barcoded logic gate modules from a library of 10 repressors with 19 RBS-repressor variants of characterized NOT gate transfer functions. Our multiplex pooled library contains 35,746 unique gate modules, which corresponds to 98.5% of all possible NOT and 2-input NOR logic gates from our library of 10 repressors and 4 input sensors (FIG. 50). From these pools, 10E26 different circuit designs could be constructed containing 1-10 gates with different wiring diagrams (permuted part assignments) and varied orientation (forward and reverse for each gate in any circuit). In total, 45% of sequencing reads were a perfect match to a designed gate module, which was improved from 20% in the about nif pathway multiplex retrievable libraries. It is believed this improvement is due to replacing the sequential type IIS scarless stitching and PCR with a one-pot type assembly and tagging reaction because in general these repressors are more toxic than the nif genes. Each repressor's NOT or NOR2 gate modules were constructed as a separate pool, and all 20 pools were sequenced in multiplex on one MiSeq v3 flow cell. On average there are 108 uniquely barcoded perfect match constructs for each designed gate module of the 35,746 unique gate modules constructed.

Figure 51:
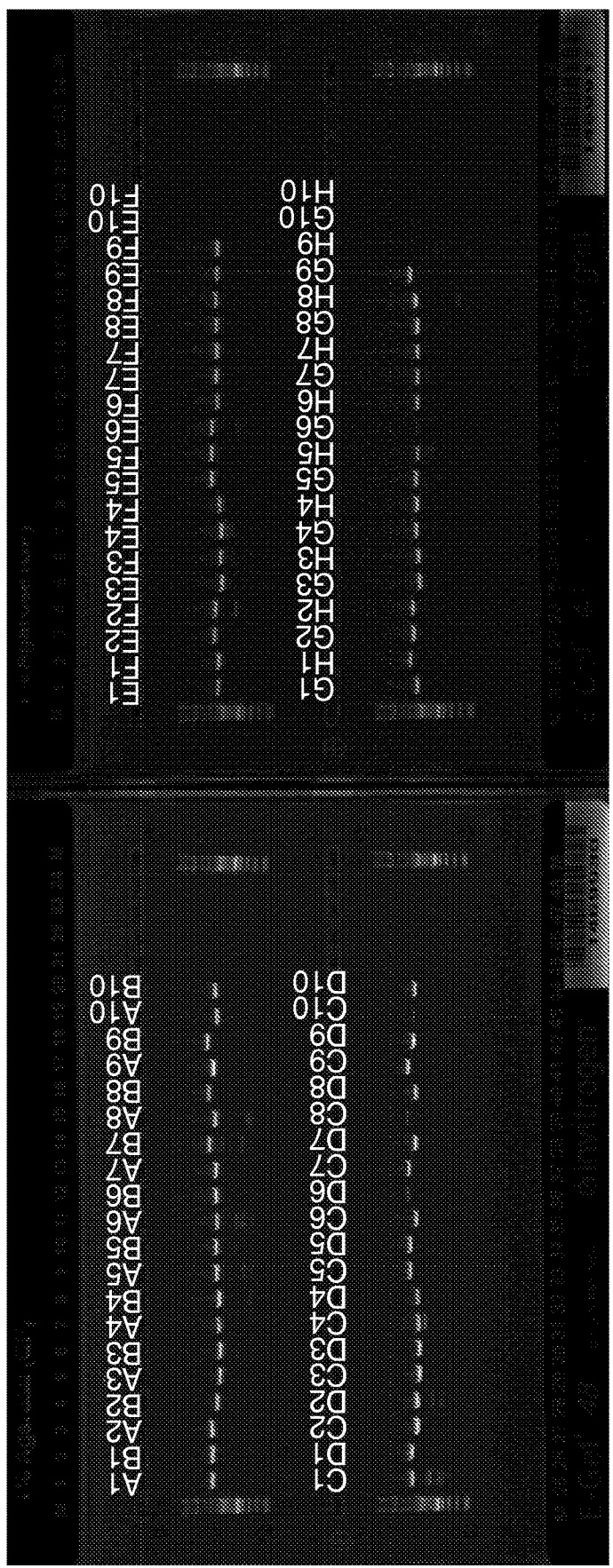
FIG. 51 is an electronic image of nucleic acid gel.
Figure 52:
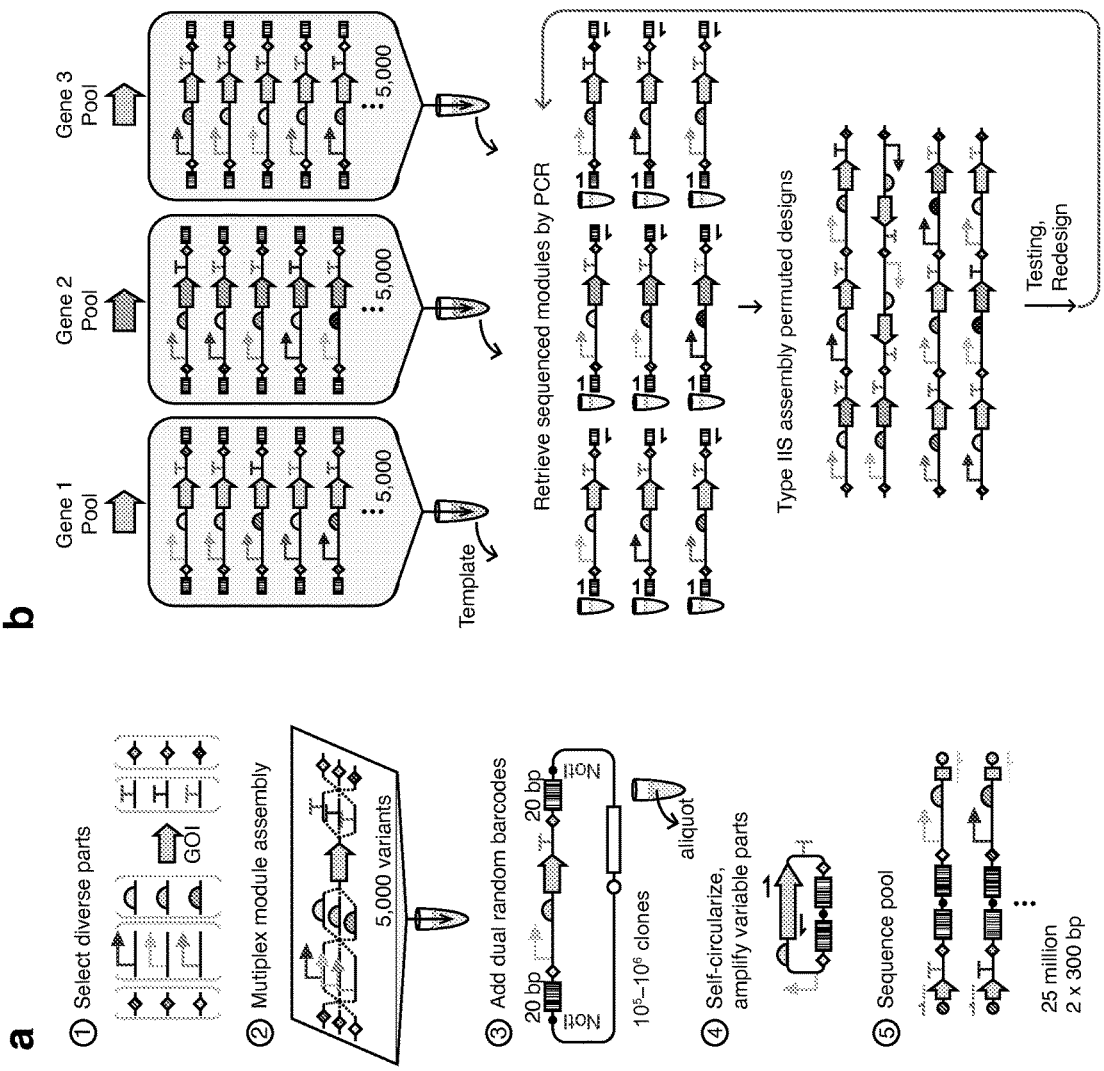
FIGS. 52A-52B are schematics each showing exemplary embodiments of the disclosed method.

To design a set of logic circuit constructs, the Cello software was implemented with an additional clustering algorithm to select diverse part assignments to the abstract wiring diagram of gates. Initially, we choose two 3-input truth tables (0x40 and 0x89 in hexadecimal notation) and designed 10 different assignments for each. In total 77 different transcriptional units including the outputs were needed for these twenty designs. Six of the PBAD-containing transcriptional units were not present in the pooled library and were constructed individually from the parts library. The retrieved of 76 barcoded transcriptional unit modules from the pool were tested after optimizing the primer and template concentrations. Seventy-five of the retrieval PCRs (98.7%) amplified the product of the correct length (FIG. 51), which exceeded our expectations given that 23 of these targets were singletons (identified from a single MiSeq read). Some of the retrieval PCRS showed multiple product lengths with additional undesired short bands. Therefore individual cloning and sequencing of a few of the multiple band retrieval PCRs were tested to confirm that only the full-length transcriptional unit assembles. The library of 20 circuit designs was assembled using a one-pot BbsI assembly, and verified full-length circuits for 15 of these designs on the initial attempt. These constructed logic circuits were tested by flow cytometry (YFP output) in all eight input states. Interestingly, most of these circuit designs result in the correct logic behavior in all 8 states. 24 constructed circuit plasmids (each gate ~1.2 kb) were fully sequenced. It was found one error in 4 of the sequenced plasmids, yet two of these minor error-containing designs were functional.

All publications, patents, and patent applications mentioned herein are incorporated by reference to the same extent as if each individual publication, patent or patent application was specifically and individually indicated to be incorporated by reference in its entirety. In the event of there being a difference between definitions set forth in this application and those in documents incorporated herein by reference, the definitions set forth herein control. Various modifications and variations of the described methods, and s of the disclosure will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

We claim:

1. A set of sequence-verified nucleic acid elements for combinatorial construction of genetic elements, said set comprising two or more nucleic acid elements assembled from a plurality of nucleic acid parts, comprising one or more categories of nucleic acid parts, wherein the nucleic acid elements comprise:
   at least two sequences selected from the plurality of nucleic acid parts;
   (ii) a 3' flanking nucleic acid sequence and a 5' flanking nucleic acid sequence, which together are capable of functioning to order assembly of higher-order nucleic acid constructs, to facilitate retrieval, and to identify the nucleic acid element,
   wherein the 3' and 5' flanking sequences comprise one or more nucleic acid barcodes that are unique to each sequence-verified nucleic acid element, which together are capable of functioning to facilitate retrieval and to identify the nucleic acid element, and
   wherein the 3' and 5' flanking sequences comprise one or more restriction sites that are capable of being cleaved prior to assembly in order to produce sticky ends to facilitate ordered assembly of higher order nucleic acid elements; and
   (iii) at least one DNA hash,
   wherein each DNA hash comprises a unique nucleic acid barcode capable of functioning to identify either the nucleic acid element or a nucleic acid part in the nucleic acid element,
   wherein the barcode of each DNA hash is flanked by primer binding sites capable of being amplified to produce an amplicon capable of forming a concatemer with an amplicon from another DNA hash in another nucleic acid element, wherein the primer binding sites are different for nucleic acid elements in the set of sequence-verified nucleic acid elements that are for each position within a combinatorial construction of genetic elements; and wherein each DNA hash is located internally to the cleavage sites for the one or more restriction sites in (ii), whereby the hash cannot be removed by restriction enzyme digestion at the one or more restriction sites.

2. The set of nucleic acid elements of claim 1, wherein at least one of the barcodes further comprise one or more sequencing adaptors, universal priming sites, sequence specific priming sites to facilitate retrieval, indexes, sequences that enable capture and/or amplification, one or more sequences that enable library construction, or a combination thereof.

3. The set of nucleic acid elements of claim 1, wherein the nucleic acid parts comprise one or more sequence variants, orthologs or homologs; or wherein the plurality of nucleic acid parts comprises one or more of:
a set of nucleic acid sequences comprising different promoters;
a set of nucleic acid sequences comprising a set of different ribosomal binding sites;
a set of nucleic acid sequences encoding a polypeptide;
a set of nucleic acid sequences encoding one or more non-coding RNAs; and/or
a set of nucleic acid sequences comprising a set of different transcription terminators.

4. The set of nucleic acid elements of claim 3, wherein the nucleic acid elements comprise at least three sequences selected from the set of promoters, ribosomal binding sites, sequences encoding a polypeptide, sequences encoding one or more non-coding RNAs, and transcription terminators; or wherein the nucleic acid elements comprise at least four sequences selected from the set of promoters, ribosomal binding sites, sequences encoding a polypeptide, sequences encoding one or more non-coding RNAs, and transcription terminators.

5. A set of plasmids comprising the set of sequence-verified nucleic acid elements of claim 1.

6. A kit comprising:
the set of sequence-verified nucleic acid elements of claim 1; or
(ii) the set of plasmids of claim 5.

7. The kit of claim 6, further comprising a plurality of primers for retrieving one or more of the sequence-verified nucleic acid elements, wherein the primers are specific for the unique nucleic acid barcodes.

8. The set of nucleic acid elements of claim 1, wherein the nucleic acid elements comprise a cistron.

9. The set of nucleic acid elements of claim 1, wherein the one or more restriction sites comprise at least one Type IIs restriction site.

10. A method of optimizing a combination of nucleic acid elements for production of an optimum desired phenotype, the method comprising:
retrieving a plurality of sequences of:
the set of sequence-verified nucleic acid elements of claim 1; and/or
(ii) a pool of higher-order nucleic acid constructs comprising the sequence-verified nucleic acid elements of claim 1;
assembling the plurality of retrieved sequences to construct a biological pathway assembly;
testing each of the assembled biological pathway assemblies fora desired phenotype;
determining which characteristic or characteristics of the assembled biological pathway contributes to the desired phenotype by comparing multiple assemblies; and
repeating the retrieving, assembling, testing, and determining until an assembled biological pathway is identified that produces said optimum desired phenotype.

* * * * *